(12) United States Patent
Ginggen et al.

(10) Patent No.: US 11,464,954 B2
(45) Date of Patent: Oct. 11, 2022

(54) DEVICES AND METHODS FOR COSMETIC SKIN RESURFACING

(71) Applicant: Cytrellis Biosystems, Inc., Woburn, MA (US)

(72) Inventors: Alec Ginggen, Medford, MA (US); Kristian DiMatteo, Waltham, MA (US); Thomas Swyst, Arlington, MA (US)

(73) Assignee: Cytrellis Biosystems, Inc., Woburn, MA (US)

( * ) Notice: Subject to any disclaimer, the term of this patent is extended or adjusted under 35 U.S.C. 154(b) by 739 days.

(21) Appl. No.: 16/335,028

(22) PCT Filed: Sep. 20, 2017

(86) PCT No.: PCT/US2017/052528
§ 371 (c)(1),
(2) Date: Mar. 20, 2019

(87) PCT Pub. No.: WO2018/057630
PCT Pub. Date: Mar. 29, 2018

(65) Prior Publication Data
US 2019/0366067 A1    Dec. 5, 2019

Related U.S. Application Data

(60) Provisional application No. 62/397,869, filed on Sep. 21, 2016.

(51) Int. Cl.
| | | |
|---|---|---|
| *A61M 37/00* | (2006.01) | |
| *A61B 17/068* | (2006.01) | |
| *A61B 90/00* | (2016.01) | |
| *A61B 17/076* | (2006.01) | |
| *A61B 17/20* | (2006.01) | |
| *A61B 17/34* | (2006.01) | |
| *A61B 17/00* | (2006.01) | |

(52) U.S. Cl.
CPC ..... *A61M 37/0015* (2013.01); *A61B 17/0682* (2013.01); *A61B 17/076* (2013.01);
(Continued)

(58) Field of Classification Search
CPC ........ A61M 37/0015; A61M 2037/003; A61M 2037/0061; A61M 5/00; A61B 17/0682;
(Continued)

(56) References Cited

U.S. PATENT DOCUMENTS

| | | |
|---|---|---|
| 2,426,535 A | 8/1947 | Turkel |
| 2,496,111 A | 1/1950 | Turkel |

(Continued)

FOREIGN PATENT DOCUMENTS

| | | |
|---|---|---|
| AU | 2012 211 122 B2 | 7/2016 |
| CA | 1275215 C | 10/1990 |

(Continued)

OTHER PUBLICATIONS

Australian Office Action dated Nov. 12, 2021 issued in corresponding Australian Application No. 2017330298.
(Continued)

*Primary Examiner* — Amber R Stiles
(74) *Attorney, Agent, or Firm* — Onello & Mello, LLP

(57) ABSTRACT

Disclosed herein are devices (e.g., needles (e.g., hollow needles), hollow staples, articles, apparatuses, and systems), kits, and methods for treating skin and skin conditions, for example, by promoting skin tightening, such as by reducing skin laxity and reducing tissue area or volume.

54 Claims, 19 Drawing Sheets

(52) U.S. Cl.
CPC ............ *A61B 17/20* (2013.01); *A61B 17/3403* (2013.01); *A61B 2017/00057* (2013.01); *A61B 2017/00544* (2013.01); *A61B 2017/00761* (2013.01); *A61B 2017/00769* (2013.01); *A61B 2017/00792* (2013.01); *A61B 2017/3411* (2013.01); *A61B 2090/395* (2016.02); *A61M 2037/003* (2013.01); *A61M 2037/0061* (2013.01)

(58) Field of Classification Search
CPC ... A61B 17/076; A61B 17/20; A61B 17/3403; A61B 2017/00057; A61B 2017/00544; A61B 2017/00761; A61B 2017/00769; A61B 2017/00792; A61B 2017/3411; A61B 2090/395; A61B 17/205; A61B 17/32053; A61B 2017/00061
See application file for complete search history.

(56) References Cited

U.S. PATENT DOCUMENTS

| | | |
|---|---|---|
| 2,881,763 A | 4/1959 | Robbins |
| 3,001,522 A | 9/1961 | Silverman |
| 3,086,530 A | 4/1963 | Groom |
| 3,214,869 A | 11/1965 | Stryker |
| 3,598,108 A | 8/1971 | Jamshidi et al. |
| 3,640,279 A | 2/1972 | Brown et al. |
| 3,683,892 A | 8/1972 | Harris |
| 3,788,320 A | 1/1974 | Dye |
| 3,867,942 A | 2/1975 | Bellantoni et al. |
| 3,929,123 A | 12/1975 | Jamshidi |
| 4,108,096 A | 8/1978 | Ciecior |
| 4,159,659 A | 7/1979 | Nightingale |
| 4,167,179 A | 9/1979 | Kirsch |
| 4,403,617 A | 9/1983 | Tretinyak |
| 4,458,678 A | 7/1984 | Yannas et al. |
| 4,476,864 A | 10/1984 | Tezel |
| 4,604,346 A | 8/1986 | Bell et al. |
| 4,640,296 A | 2/1987 | Schnepp-Pesch et al. |
| 4,649,918 A | 3/1987 | Pegg et al. |
| D297,375 S | 8/1988 | Liu |
| 4,815,462 A | 3/1989 | Clark |
| 4,865,026 A | 9/1989 | Barrett |
| 4,903,709 A | 2/1990 | Skinner |
| 4,930,997 A | 6/1990 | Bennett |
| D323,034 S | 1/1992 | Reinstein |
| 5,152,763 A | 10/1992 | Johnson |
| D338,070 S | 8/1993 | Lam |
| 5,242,453 A | 9/1993 | Gubich |
| D342,138 S | 12/1993 | Wollman et al. |
| 5,269,316 A | 12/1993 | Spitalny |
| 5,306,490 A | 4/1994 | Barley, Jr. |
| 5,324,305 A | 6/1994 | Kanner |
| 5,331,972 A | 7/1994 | Wadhwani et al. |
| 5,415,182 A | 5/1995 | Chin et al. |
| 5,417,683 A | 5/1995 | Shiao |
| 5,419,761 A | 5/1995 | Narayanan et al. |
| 5,439,475 A | 8/1995 | Bennett |
| 5,458,112 A | 10/1995 | Weaver |
| D377,404 S | 1/1997 | Izumi |
| 5,593,381 A | 1/1997 | Tannenbaum et al. |
| 5,611,810 A | 3/1997 | Arnold et al. |
| 5,615,690 A | 4/1997 | Giurtino et al. |
| 5,639,654 A | 6/1997 | Bernard et al. |
| 5,643,308 A | 7/1997 | Markman |
| D388,543 S | 12/1997 | Eguchi et al. |
| 5,713,375 A | 2/1998 | McAllister |
| 5,749,895 A | 5/1998 | Sawyer et al. |
| 5,792,169 A * | 8/1998 | Markman ............... A61F 2/10 606/186 |
| 5,810,857 A | 9/1998 | Mackool |
| 5,827,297 A | 10/1998 | Boudjema |
| 5,868,744 A | 2/1999 | Willmen |
| 5,871,495 A | 2/1999 | Mueller |
| 5,879,326 A | 3/1999 | Godshall et al. |
| 5,885,211 A | 3/1999 | Eppstein et al. |
| 5,885,226 A | 3/1999 | Rubinstein et al. |
| 5,902,319 A | 5/1999 | Daley |
| 5,922,000 A | 7/1999 | Chodorow |
| 5,925,002 A | 7/1999 | Wollman |
| 5,928,162 A | 7/1999 | Giurtino et al. |
| 5,931,855 A | 8/1999 | Buncke |
| 5,989,273 A | 11/1999 | Arnold |
| 6,022,324 A | 2/2000 | Skinner |
| 6,027,512 A | 2/2000 | Bridges |
| D425,241 S | 5/2000 | Nishizawa et al. |
| 6,059,807 A | 5/2000 | Boudjema |
| 6,063,094 A | 5/2000 | Rosenberg |
| 6,178,346 B1 | 1/2001 | Amundson et al. |
| 6,197,039 B1 | 3/2001 | Ashraf |
| 6,211,598 B1 | 4/2001 | Dhuler et al. |
| 6,241,687 B1 | 6/2001 | Voegele et al. |
| 6,241,739 B1 | 6/2001 | Waldron |
| 6,251,097 B1 | 6/2001 | Kline et al. |
| 6,264,618 B1 | 7/2001 | Landi et al. |
| 6,342,213 B1 | 1/2002 | Barley et al. |
| D457,265 S | 5/2002 | Gebhard |
| D458,710 S | 6/2002 | Altamore et al. |
| 6,419,641 B1 | 7/2002 | Mark et al. |
| 6,432,098 B1 | 8/2002 | Kline et al. |
| 6,440,086 B1 | 8/2002 | Hohenberg |
| 6,461,369 B1 | 10/2002 | Kim |
| 6,494,844 B1 | 12/2002 | Van Bladel et al. |
| 6,537,242 B1 | 3/2003 | Palmer |
| 6,537,264 B1 | 3/2003 | Cormier et al. |
| 6,562,037 B2 | 5/2003 | Paton et al. |
| 6,592,530 B1 | 7/2003 | Farhadi |
| 6,669,618 B2 | 12/2003 | Reising et al. |
| 6,669,694 B2 | 12/2003 | Shadduck |
| 6,689,072 B2 | 2/2004 | Kaplan et al. |
| 6,730,098 B2 | 5/2004 | Chang |
| 6,733,496 B2 | 5/2004 | Sharkey et al. |
| 6,733,498 B2 | 5/2004 | Paton et al. |
| D500,391 S | 12/2004 | Nielsen et al. |
| 6,881,203 B2 | 4/2005 | Delmore et al. |
| 6,887,250 B1 | 5/2005 | Dority et al. |
| 6,893,388 B2 | 5/2005 | Reising et al. |
| 6,936,039 B2 | 8/2005 | Kline et al. |
| D509,301 S | 9/2005 | Talbot et al. |
| 6,945,952 B2 | 9/2005 | Kwon |
| 6,997,923 B2 | 2/2006 | Anderson et al. |
| 7,073,510 B2 | 7/2006 | Redmond et al. |
| 7,131,951 B2 | 11/2006 | Angel |
| D538,430 S | 3/2007 | Ohta |
| 7,350,983 B2 | 4/2008 | Saitoh et al. |
| 7,364,565 B2 | 4/2008 | Freeman |
| 7,372,608 B2 | 5/2008 | Fujimori |
| 7,618,429 B2 | 11/2009 | Mulholland |
| 7,651,507 B2 | 1/2010 | Mishra et al. |
| 7,658,728 B2 | 2/2010 | Yuzhakov |
| 7,704,274 B2 | 4/2010 | Boyle et al. |
| 7,717,274 B2 | 5/2010 | Kao et al. |
| 7,926,401 B2 | 4/2011 | Mishra et al. |
| 8,128,639 B2 | 3/2012 | Tippett |
| 8,209,006 B2 | 6/2012 | Smith et al. |
| 8,216,224 B2 | 7/2012 | Morris et al. |
| 8,226,664 B2 | 7/2012 | Drews et al. |
| 8,246,611 B2 | 8/2012 | Paithankar et al. |
| 8,328,738 B2 | 12/2012 | Frankhouser et al. |
| 8,353,861 B2 | 1/2013 | Tobinaga et al. |
| 8,388,631 B2 | 3/2013 | Oostman, Jr. et al. |
| 8,435,791 B2 | 5/2013 | Galun et al. |
| 8,480,592 B2 | 7/2013 | Chudzik et al. |
| 8,545,489 B2 | 10/2013 | Giovannoli |
| 8,574,253 B2 | 11/2013 | Gruber et al. |
| 8,597,204 B2 | 12/2013 | Flatland et al. |
| 8,696,686 B2 | 4/2014 | Drews et al. |
| 8,900,181 B2 | 12/2014 | Knowlton |
| 8,951,266 B2 | 2/2015 | Zingaretti et al. |
| 9,017,343 B2 | 4/2015 | Westerling, Jr. et al. |
| 9,060,803 B2 | 6/2015 | Anderson et al. |
| 9,084,465 B2 | 7/2015 | Oostman, Jr. et al. |
| 9,119,945 B2 | 9/2015 | Simons et al. |

(56) References Cited

U.S. PATENT DOCUMENTS

| | | |
|---|---|---|
| 9,198,686 B2 | 12/2015 | Motai et al. |
| 9,301,497 B2 | 4/2016 | Hilpert et al. |
| 9,314,262 B2 | 4/2016 | Harris |
| 9,408,691 B2 | 8/2016 | Oostman et al. |
| 9,414,815 B2 | 8/2016 | Miller et al. |
| 9,439,673 B2 | 9/2016 | Austen |
| 9,480,496 B2 | 11/2016 | Cole et al. |
| 9,561,051 B2 | 2/2017 | Austen et al. |
| D797,286 S | 9/2017 | Ginggen et al. |
| 9,895,162 B2 | 2/2018 | Anderson et al. |
| 10,251,792 B2 | 4/2019 | Levinson et al. |
| 10,543,127 B2 | 1/2020 | Levinson et al. |
| 10,555,754 B2 | 2/2020 | Ginggen et al. |
| 10,687,842 B2 | 6/2020 | Austen et al. |
| 10,716,591 B2 | 7/2020 | Anderson et al. |
| 10,736,654 B2 | 8/2020 | Anderson et al. |
| 10,737,081 B2 | 8/2020 | Jung et al. |
| 10,953,143 B2 | 3/2021 | Ginggen et al. |
| 2001/0018572 A1 | 8/2001 | Kinsey et al. |
| 2002/0022854 A1 | 2/2002 | Irion et al. |
| 2002/0022861 A1 | 2/2002 | Jacobs et al. |
| 2002/0045859 A1 | 4/2002 | Gartstein et al. |
| 2002/0055689 A1 | 5/2002 | Kaplan et al. |
| 2002/0103500 A1 | 8/2002 | Gildenberg |
| 2002/0120260 A1 | 8/2002 | Morris et al. |
| 2002/0169431 A1 | 11/2002 | Kline et al. |
| 2002/0183688 A1 | 12/2002 | Lastovich et al. |
| 2002/0187556 A1 | 12/2002 | Shartle et al. |
| 2002/0188280 A1 | 12/2002 | Nguyen et al. |
| 2003/0023196 A1 | 1/2003 | Liguori |
| 2003/0036770 A1 | 2/2003 | Markman |
| 2003/0083607 A1 | 5/2003 | Bobo, Jr. |
| 2003/0088220 A1 | 5/2003 | Molander et al. |
| 2003/0119641 A1 | 6/2003 | Reising |
| 2003/0135161 A1 | 7/2003 | Fleming et al. |
| 2003/0144656 A1 | 7/2003 | Ocel et al. |
| 2003/0153960 A1 | 8/2003 | Chornenky et al. |
| 2003/0158521 A1 | 8/2003 | Ameri |
| 2003/0158566 A1 | 8/2003 | Brett |
| 2003/0163160 A1 | 8/2003 | O'Malley et al. |
| 2003/0181936 A1 | 9/2003 | Trautman et al. |
| 2003/0187462 A1 | 10/2003 | Chang |
| 2003/0195625 A1 | 10/2003 | Garcia Castro et al. |
| 2003/0199811 A1 | 10/2003 | Sage et al. |
| 2003/0212415 A1 | 11/2003 | Karasiuk |
| 2003/0233082 A1 | 12/2003 | Kline et al. |
| 2004/0002723 A1 | 1/2004 | Ball |
| 2004/0010268 A1 | 1/2004 | Gabehart |
| 2004/0015139 A1 | 1/2004 | La Bianco et al. |
| 2004/0019297 A1 | 1/2004 | Angel |
| 2004/0023771 A1 | 2/2004 | Reising et al. |
| 2004/0054410 A1 | 3/2004 | Barrows |
| 2004/0073195 A1 | 4/2004 | Cucin |
| 2004/0087893 A1 | 5/2004 | Kwon |
| 2004/0087992 A1 | 5/2004 | Gartstein et al. |
| 2004/0098094 A1 | 5/2004 | Boyle et al. |
| 2004/0122471 A1 | 6/2004 | Toby et al. |
| 2004/0138680 A1 | 7/2004 | Twitchell et al. |
| 2004/0162566 A1 | 8/2004 | Carson et al. |
| 2004/0167430 A1 | 8/2004 | Roshdieh et al. |
| 2004/0175690 A1 | 9/2004 | Mishra et al. |
| 2004/0186421 A1 | 9/2004 | Freeman |
| 2004/0220589 A1 | 11/2004 | Feller |
| 2005/0049582 A1 | 3/2005 | DeBenedictis et al. |
| 2005/0065463 A1 | 3/2005 | Tobinaga et al. |
| 2005/0090765 A1 | 4/2005 | Fisher |
| 2005/0130821 A1 | 6/2005 | Reising et al. |
| 2005/0137525 A1 | 6/2005 | Wang et al. |
| 2005/0165329 A1 | 7/2005 | Taylor et al. |
| 2005/0171480 A1 | 8/2005 | Mukerjee et al. |
| 2005/0171567 A1 | 8/2005 | Dehart |
| 2005/0203575 A1 | 9/2005 | Carson et al. |
| 2005/0209567 A1 | 9/2005 | Sibbitt |
| 2005/0215921 A1 | 9/2005 | Hibner et al. |
| 2005/0215970 A1 | 9/2005 | Kline et al. |
| 2005/0215971 A1 | 9/2005 | Roe et al. |
| 2005/0226856 A1 | 10/2005 | Ahlfors |
| 2005/0234419 A1 | 10/2005 | Kline et al. |
| 2005/0245952 A1 | 11/2005 | Feller |
| 2005/0267506 A1 | 12/2005 | Harris |
| 2005/0274679 A1 | 12/2005 | Kao et al. |
| 2005/0283141 A1 | 12/2005 | Giovannoli |
| 2006/0047234 A1 | 3/2006 | Glucksman et al. |
| 2006/0064031 A1 | 3/2006 | Miller |
| 2006/0116605 A1 | 6/2006 | Nakao |
| 2006/0155266 A1 | 7/2006 | Manstein et al. |
| 2006/0161179 A1 | 7/2006 | Kachenmeister |
| 2006/0184153 A1 | 8/2006 | Mark et al. |
| 2006/0193819 A1 | 8/2006 | Lu et al. |
| 2006/0216781 A1 | 9/2006 | Gebing |
| 2006/0259006 A1 | 11/2006 | McKay et al. |
| 2006/0264926 A1 | 11/2006 | Kochamba |
| 2006/0271070 A1 | 11/2006 | Eriksson et al. |
| 2006/0276806 A1 | 12/2006 | Martinez Zunino |
| 2007/0010810 A1 | 1/2007 | Kochamba |
| 2007/0031092 A1 | 2/2007 | Saitoh et al. |
| 2007/0038181 A1 | 2/2007 | Melamud et al. |
| 2007/0038236 A1 | 2/2007 | Cohen |
| 2007/0060888 A1 | 3/2007 | Goff et al. |
| 2007/0068537 A1 | 3/2007 | Giovannoli |
| 2007/0073217 A1 | 3/2007 | James |
| 2007/0073327 A1 | 3/2007 | Giovannoli |
| 2007/0078359 A1 | 4/2007 | Luloh et al. |
| 2007/0078466 A1 | 4/2007 | Bodduluri et al. |
| 2007/0078473 A1 | 4/2007 | Bodduluri et al. |
| 2007/0106306 A1 | 5/2007 | Bodduluri et al. |
| 2007/0142722 A1 | 6/2007 | Chang |
| 2007/0142744 A1 | 6/2007 | Provencher |
| 2007/0142885 A1 | 6/2007 | Hantash et al. |
| 2007/0149991 A1 | 6/2007 | Mulholland |
| 2007/0156161 A1 | 7/2007 | Weadock et al. |
| 2007/0167958 A1 | 7/2007 | Sulamanidze et al. |
| 2007/0171504 A1 | 7/2007 | Fujimori |
| 2007/0179455 A1 | 8/2007 | Geliebter et al. |
| 2007/0179481 A1 | 8/2007 | Frangineas et al. |
| 2007/0183938 A1 | 8/2007 | Booker |
| 2007/0198000 A1 | 8/2007 | Miyamoto et al. |
| 2007/0213634 A1 | 9/2007 | Teague |
| 2007/0239236 A1 | 10/2007 | Manstein |
| 2007/0239260 A1 | 10/2007 | Palanker et al. |
| 2007/0249960 A1 | 10/2007 | Williamson |
| 2007/0270710 A1 | 11/2007 | Frass et al. |
| 2007/0156164 A1 | 12/2007 | Cole et al. |
| 2008/0009802 A1 | 1/2008 | Lambino et al. |
| 2008/0009896 A1 | 1/2008 | Shiao |
| 2008/0009901 A1 | 1/2008 | Redmond et al. |
| 2008/0033334 A1 | 2/2008 | Gurtner et al. |
| 2008/0045858 A1 | 2/2008 | Tessitore et al. |
| 2008/0045861 A1 | 2/2008 | Miller et al. |
| 2008/0051805 A1 | 2/2008 | Pinchuk |
| 2008/0132979 A1 | 6/2008 | Gerber |
| 2008/0146982 A1 | 6/2008 | Rastegar et al. |
| 2008/0177287 A1 | 7/2008 | Rassman et al. |
| 2008/0183167 A1 | 7/2008 | Britva et al. |
| 2008/0208146 A1 | 8/2008 | Brandwein et al. |
| 2008/0221548 A1 | 9/2008 | Danenberg et al. |
| 2008/0234602 A1 | 9/2008 | Oostman et al. |
| 2008/0234699 A1 | 9/2008 | Oostman, Jr. et al. |
| 2008/0249553 A1 | 10/2008 | Gruber et al. |
| 2008/0269735 A1 | 10/2008 | Vila Echague et al. |
| 2008/0275378 A1 | 11/2008 | Herndon |
| 2008/0300507 A1 | 12/2008 | Figueredo et al. |
| 2008/0306471 A1 | 12/2008 | Altshuler et al. |
| 2008/0312648 A1 | 12/2008 | Peterson |
| 2009/0030340 A1 | 1/2009 | McClellan |
| 2009/0048557 A1 | 2/2009 | Yeshurun et al. |
| 2009/0076497 A1 | 3/2009 | Morris et al. |
| 2009/0088720 A1 | 4/2009 | Oostman, Jr. |
| 2009/0093864 A1 | 4/2009 | Anderson |
| 2009/0125050 A1 | 5/2009 | Dixon |
| 2009/0146068 A1 | 6/2009 | Agarwal |
| 2009/0163877 A1 | 6/2009 | Christoffersen et al. |
| 2009/0198336 A1 | 8/2009 | Qiao et al. |
| 2009/0227895 A1 | 9/2009 | Goldenberg |

(56) References Cited

U.S. PATENT DOCUMENTS

| | | |
|---|---|---|
| 2009/0312749 A1 | 12/2009 | Pini et al. |
| 2010/0004558 A1 | 1/2010 | Frankhouser et al. |
| 2010/0023003 A1 | 1/2010 | Mulholland |
| 2010/0030152 A1 | 2/2010 | Lee et al. |
| 2010/0041938 A1 | 2/2010 | Stoianovici et al. |
| 2010/0042014 A1 | 2/2010 | Djordjevic et al. |
| 2010/0057100 A1 | 3/2010 | Zeevi |
| 2010/0082042 A1 | 4/2010 | Drews |
| 2010/0121307 A1 | 5/2010 | Lockard et al. |
| 2010/0145373 A1 | 6/2010 | Alon |
| 2010/0160822 A1 | 6/2010 | Parihar et al. |
| 2010/0185116 A1 | 7/2010 | Al-Mohizea |
| 2010/0191253 A1 | 7/2010 | Oostman, Jr. et al. |
| 2010/0286618 A1 | 11/2010 | Choi |
| 2010/0330589 A1 | 12/2010 | Bahrami et al. |
| 2011/0009882 A1 | 1/2011 | Remsburg et al. |
| 2011/0028898 A1 | 2/2011 | Clark, III et al. |
| 2011/0040497 A1 | 2/2011 | Olesen |
| 2011/0046616 A1 | 2/2011 | Manstein |
| 2011/0092844 A1 | 4/2011 | Bargo et al. |
| 2011/0105949 A1 | 5/2011 | Wiksell |
| 2011/0152738 A1 | 6/2011 | Zepeda et al. |
| 2011/0166520 A1 | 7/2011 | Iwase et al. |
| 2011/0172745 A1 | 7/2011 | Na et al. |
| 2011/0245726 A1 | 10/2011 | Flatland et al. |
| 2011/0245834 A1 | 10/2011 | Miklosovic |
| 2011/0251602 A1 | 10/2011 | Anderson et al. |
| 2011/0257588 A1 | 10/2011 | Knowlton |
| 2011/0270274 A1 | 11/2011 | Hull, Jr. |
| 2011/0282238 A1 | 11/2011 | Houser et al. |
| 2011/0313345 A1 | 12/2011 | Schafer |
| 2011/0313429 A1 | 12/2011 | Anderson et al. |
| 2012/0010526 A1 | 1/2012 | Hilpert et al. |
| 2012/0010527 A1 | 1/2012 | Sundheimer et al. |
| 2012/0041430 A1 | 2/2012 | Anderson et al. |
| 2012/0065551 A1 | 3/2012 | Aviad et al. |
| 2012/0136387 A1 | 5/2012 | Redmond et al. |
| 2012/0158100 A1 | 6/2012 | Schomacker |
| 2012/0179189 A1 | 7/2012 | Zingaretti et al. |
| 2012/0209283 A1 | 8/2012 | Zhu |
| 2012/0226214 A1 | 9/2012 | Gurtner et al. |
| 2012/0226268 A1 | 9/2012 | Liu et al. |
| 2012/0226306 A1 | 9/2012 | Jackson et al. |
| 2012/0245629 A1 | 9/2012 | Gross et al. |
| 2012/0253333 A1 | 10/2012 | Garden et al. |
| 2012/0259237 A1 | 10/2012 | Axelrod |
| 2012/0271320 A1 | 10/2012 | Hall et al. |
| 2012/0289985 A1 | 11/2012 | Motai et al. |
| 2013/0006168 A1 | 1/2013 | Del Vecchio |
| 2013/0041397 A1 | 2/2013 | Nishimura |
| 2013/0045171 A1 | 2/2013 | Utecht et al. |
| 2013/0110026 A1 | 5/2013 | Jackson et al. |
| 2013/0131635 A1 | 5/2013 | Rimsa et al. |
| 2013/0204238 A1 | 8/2013 | Lederman et al. |
| 2014/0036523 A1 | 2/2014 | Thullier et al. |
| 2014/0039523 A1 | 2/2014 | Austen |
| 2014/0163582 A1 | 6/2014 | Austen et al. |
| 2014/0200484 A1 | 7/2014 | Austen et al. |
| 2014/0249547 A1 | 9/2014 | Boone, III |
| 2014/0276205 A1 | 9/2014 | Miller et al. |
| 2014/0276959 A1 | 9/2014 | Oostman et al. |
| 2014/0277055 A1 | 9/2014 | Austen, Jr. |
| 2014/0296741 A1 | 10/2014 | Austen |
| 2014/0296796 A1 | 10/2014 | Lim |
| 2014/0303648 A1 | 10/2014 | Knowlton |
| 2014/0343481 A1 | 11/2014 | Ignon |
| 2015/0143713 A1 | 5/2015 | Cheng |
| 2015/0173991 A1 | 6/2015 | Anderson et al. |
| 2015/0216545 A1 | 8/2015 | Anderson et al. |
| 2015/0238214 A1 | 8/2015 | Anderson et al. |
| 2015/0258319 A1 | 9/2015 | Simmers |
| 2015/0320990 A1 | 11/2015 | Burton et al. |
| 2015/0366719 A1 | 12/2015 | Levinson et al. |
| 2016/0082241 A1 | 3/2016 | Burton et al. |
| 2016/0095592 A1 | 4/2016 | Levinson et al. |
| 2016/0121091 A1 | 5/2016 | Burton et al. |
| 2016/0129198 A1 | 5/2016 | Bitar et al. |
| 2016/0136406 A1 | 5/2016 | Berry et al. |
| 2016/0192961 A1 | 7/2016 | Ginggen et al. |
| 2016/0317721 A1 | 11/2016 | Ginggen et al. |
| 2016/0361527 A1 | 12/2016 | Jung et al. |
| 2016/0367280 A1 | 12/2016 | Austen |
| 2017/0105749 A1 | 4/2017 | Austen et al. |
| 2017/0367729 A1 | 12/2017 | Ginggen et al. |
| 2018/0008500 A1 | 1/2018 | Anderson et al. |
| 2018/0021087 A1 | 1/2018 | Anderson et al. |
| 2018/0036029 A1 | 2/2018 | Anderson et al. |
| 2018/0078278 A1 | 3/2018 | Levinson et al. |
| 2018/0140316 A1 | 5/2018 | Anderson et al. |
| 2018/0185196 A1 | 7/2018 | Levinson et al. |
| 2018/0193054 A1 | 7/2018 | Austen |
| 2018/0206875 A1 | 7/2018 | Austen et al. |
| 2019/0099199 A1 | 4/2019 | Levinson et al. |
| 2019/0231324 A1 | 8/2019 | Austen et al. |
| 2019/0366067 A1 | 12/2019 | Ginggen et al. |
| 2020/0038051 A1 | 2/2020 | Austen |
| 2020/0121354 A1 | 4/2020 | Ginggen et al. |
| 2020/0188184 A1 | 6/2020 | Levinson et al. |
| 2020/0214766 A1 | 7/2020 | Anderson et al. |
| 2020/0246039 A1 | 8/2020 | Levinson et al. |
| 2020/0360039 A1 | 11/2020 | Anderson et al. |
| 2020/0360043 A1 | 11/2020 | Anderson et al. |
| 2021/0059703 A1 | 3/2021 | Austen et al. |
| 2021/0178028 A1 | 6/2021 | Ginggen et al. |
| 2021/0322005 A1 | 10/2021 | Levinson et al. |
| 2021/0401453 A1 | 12/2021 | Dimatteo et al. |
| 2022/0125477 A1 | 4/2022 | Brik et al. |

FOREIGN PATENT DOCUMENTS

| | | |
|---|---|---|
| CA | 2361777 A1 | 5/2002 |
| CN | 2126570 | 1/1993 |
| CN | 2126570 Y | 1/1993 |
| CN | 1115629 A | 1/1996 |
| CN | 201005966 Y | 1/2008 |
| CN | 101128156 A | 2/2008 |
| CN | 101208128 A | 6/2008 |
| CN | 101232858 A | 7/2008 |
| CN | 101277657 A | 10/2008 |
| CN | 101312692 A | 11/2008 |
| CN | 101347346 A | 1/2009 |
| CN | 201216811 | 4/2009 |
| CN | 101563113 A | 10/2009 |
| CN | 101670145 A | 3/2010 |
| CN | 102119006 A | 7/2011 |
| CN | 102143724 A | 8/2011 |
| CN | 102178616 A | 9/2011 |
| CN | 202113484 U | 1/2012 |
| CN | 102958460 | 3/2013 |
| CN | 103547226 A | 1/2014 |
| CN | 105492064 | 4/2016 |
| DE | DD287651 A5 | 3/1991 |
| DE | 9211681 | 11/1992 |
| DE | 202004010659 U1 | 10/2004 |
| DE | 102007026973 A1 | 12/2008 |
| EA | 9092 | 10/2007 |
| EP | 0027974 A1 | 5/1981 |
| EP | 1224949 A1 | 7/2002 |
| EP | 1278061 A1 | 1/2003 |
| EP | 1396230 A1 | 3/2004 |
| EP | 1618925 A1 | 1/2006 |
| EP | 2181732 A1 | 5/2010 |
| EP | 1278061 B1 | 2/2011 |
| EP | 2409727 A1 | 1/2012 |
| FR | 2846221 B1 | 7/2005 |
| JP | S57-163208 A | 10/1982 |
| JP | 10210 | 1/1998 |
| JP | 2000-139929 A | 5/2000 |
| JP | 2001-187058 A | 7/2001 |
| JP | 2002-505605 A | 2/2002 |
| JP | 2003-515424 A | 5/2003 |
| JP | 2003-518975 A | 6/2003 |
| JP | 2003-532480 A | 11/2003 |
| JP | 2004-503342 A | 2/2004 |

(56) References Cited

FOREIGN PATENT DOCUMENTS

| | | |
|---|---|---|
| JP | 2004154296 | 6/2004 |
| JP | 2005-000642 A | 1/2005 |
| JP | 2005-87519 A | 4/2005 |
| JP | 2005-87520 A | 4/2005 |
| JP | 2005-103276 A | 4/2005 |
| JP | 2005103276 | 4/2005 |
| JP | 2005137454 | 6/2005 |
| JP | 2006-516201 A | 6/2006 |
| JP | 2006-517814 A | 8/2006 |
| JP | 2007-041267 A | 2/2007 |
| JP | 2007-100140 A | 4/2007 |
| JP | 2007229330 | 9/2007 |
| JP | 2008-036393 A | 2/2008 |
| JP | 2008-528207 A | 7/2008 |
| JP | 2009-502413 A | 1/2009 |
| JP | 2009-507773 A | 2/2009 |
| JP | 2009-509671 A | 3/2009 |
| JP | 2009-172418 A | 8/2009 |
| JP | 2009-219858 A | 10/2009 |
| JP | 2009-545382 A | 12/2009 |
| JP | 2010-000210 A | 1/2010 |
| JP | 4431637 B2 | 3/2010 |
| JP | 2010-515469 A | 5/2010 |
| JP | 2010-524591 A | 7/2010 |
| JP | 2010-525887 A | 7/2010 |
| JP | 2010532178 | 10/2010 |
| JP | 2011-516169 A | 5/2011 |
| JP | 2013094530 | 5/2013 |
| JP | 2013-526300 A | 6/2013 |
| JP | 2013532557 | 8/2013 |
| JP | 2014506498 | 3/2014 |
| JP | 5944925 B2 | 7/2016 |
| JP | 6406915 | 10/2018 |
| KR | 2008-0030553 A | 4/2008 |
| KR | 2008-0049793 A | 6/2008 |
| KR | 20090039073 | 4/2009 |
| KR | 2010-0135863 A | 12/2010 |
| KR | 2010/0135864 A | 12/2010 |
| KR | 10-2012-0135429 A | 12/2012 |
| KR | 101571291 | 11/2015 |
| KR | 101571291 B1 | 11/2015 |
| RU | 1801391 C | 3/1993 |
| RU | 2119304 C1 | 9/1998 |
| RU | 11679 | 11/1999 |
| RU | 28328 | 3/2003 |
| RU | 50799 | 1/2006 |
| RU | 58359 | 11/2006 |
| RU | 2289332 C2 | 12/2006 |
| RU | 2308873 C2 | 10/2007 |
| RU | 2325859 C2 | 6/2008 |
| SU | 1426740 | 9/1988 |
| TW | 402497 B | 8/2000 |
| TW | 200841866 A | 11/2008 |
| WO | WO-93/22971 A1 | 11/1993 |
| WO | WO-1995/28896 A1 | 11/1995 |
| WO | WO-97/18758 A1 | 5/1997 |
| WO | 9826719 | 6/1998 |
| WO | WO-98/26719 A1 | 6/1998 |
| WO | 9829149 | 7/1998 |
| WO | WO-98/57587 A1 | 12/1998 |
| WO | 9921497 | 5/1999 |
| WO | WO-99/29243 A1 | 6/1999 |
| WO | 0064379 | 11/2000 |
| WO | 0074763 | 12/2000 |
| WO | WO-0141651 A2 | 6/2001 |
| WO | WO-01/49186 A2 | 7/2001 |
| WO | WO-01/85035 A2 | 11/2001 |
| WO | WO-02/05890 A2 | 1/2002 |
| WO | WO-02/096321 A1 | 12/2002 |
| WO | WO-2004/045671 A2 | 6/2004 |
| WO | WO-2004/107984 A1 | 12/2004 |
| WO | WO-2005/013830 A1 | 2/2005 |
| WO | WO-2005/072181 A2 | 8/2005 |
| WO | WO-2005/109799 A2 | 11/2005 |
| WO | WO-2006/081556 A2 | 8/2006 |
| WO | WO-2006/116281 A2 | 11/2006 |
| WO | WO-2006/118804 A1 | 11/2006 |
| WO | WO-2007/011788 A2 | 1/2007 |
| WO | 2007021905 | 2/2007 |
| WO | WO-2007/015232 A1 | 2/2007 |
| WO | WO-2007/015247 A2 | 2/2007 |
| WO | WO-2007/024038 A2 | 3/2007 |
| WO | 2007041267 | 4/2007 |
| WO | WO-2007/041267 A2 | 4/2007 |
| WO | WO-2007/066339 A1 | 6/2007 |
| WO | WO-2007/080596 A2 | 7/2007 |
| WO | WO-2007/106170 A2 | 9/2007 |
| WO | WO-2008/019051 A2 | 2/2008 |
| WO | WO-2008/033873 A2 | 3/2008 |
| WO | WO-2008/052189 A2 | 5/2008 |
| WO | 2008121920 | 10/2008 |
| WO | WO-2008/131302 A2 | 10/2008 |
| WO | 200904093 | 4/2009 |
| WO | WO-2009/040493 A1 | 4/2009 |
| WO | WO-2009/072108 A2 | 6/2009 |
| WO | WO-2009/072711 A2 | 6/2009 |
| WO | 2009099988 | 8/2009 |
| WO | WO-2009/099988 A2 | 8/2009 |
| WO | WO-2009/137288 A2 | 11/2009 |
| WO | WO-2009/146053 A1 | 12/2009 |
| WO | WO-2009/146068 A1 | 12/2009 |
| WO | WO-2009/146072 A1 | 12/2009 |
| WO | WO-2010/027188 A2 | 3/2010 |
| WO | WO-2010/080014 A2 | 7/2010 |
| WO | WO-2010/095456 A1 | 8/2010 |
| WO | WO-2010/097790 A1 | 9/2010 |
| WO | WO-2011/006009 A1 | 1/2011 |
| WO | WO-2011/019859 A2 | 2/2011 |
| WO | WO-2011/075676 A2 | 6/2011 |
| WO | WO-2011/104875 A1 | 9/2011 |
| WO | WO-2011/123218 A1 | 10/2011 |
| WO | 2011140197 | 11/2011 |
| WO | WO-2011/075676 A3 | 11/2011 |
| WO | WO-2011140497 A2 | 11/2011 |
| WO | WO-2012/052986 A2 | 4/2012 |
| WO | WO-2012/103483 A2 | 8/2012 |
| WO | WO-2012/103488 A1 | 8/2012 |
| WO | WO-2012/103492 A1 | 8/2012 |
| WO | WO-2012/119131 A1 | 9/2012 |
| WO | WO-2012/135828 A1 | 10/2012 |
| WO | WO-2013/013196 A1 | 1/2013 |
| WO | WO-2013/013199 A2 | 1/2013 |
| WO | WO-2013/104414 A1 | 7/2013 |
| WO | WO-2014/008470 A1 | 1/2014 |
| WO | WO-2014/008481 A1 | 1/2014 |
| WO | 2014028626 | 2/2014 |
| WO | WO-2014/089488 A2 | 6/2014 |
| WO | WO-2014/130359 A1 | 8/2014 |
| WO | WO-2014/151104 A1 | 9/2014 |
| WO | WO-2014/179729 A1 | 11/2014 |
| WO | WO-2015/021434 A2 | 2/2015 |
| WO | WO-2015/051164 A2 | 4/2015 |
| WO | WO-2015/095675 A1 | 6/2015 |
| WO | WO-2015/126926 A1 | 8/2015 |
| WO | WO-2016/033584 A1 | 3/2016 |
| WO | WO-2016/033586 A1 | 3/2016 |
| WO | WO-2016/077759 A1 | 5/2016 |
| WO | WO-2016/127091 A1 | 8/2016 |
| WO | WO-2017/139773 A2 | 8/2017 |
| WO | WO-2017/172920 A1 | 10/2017 |
| WO | WO-2017/192723 A1 | 11/2017 |
| WO | WO-2018/057630 A1 | 3/2018 |
| WO | WO-2018/057637 A1 | 3/2018 |
| WO | WO-2020/097244 A1 | 5/2020 |

OTHER PUBLICATIONS

Canadian Office Action dated Nov. 17, 2021 issued in corresponding Canadian Application No. 3037490.
Chinese Office Action dated Oct. 18, 2021 issued in corresponding Chinese Application No. 201780069547.9, with English language summary.

(56) References Cited

OTHER PUBLICATIONS

International Search Report for PCT/US2019/060131 (Systems and Methods for Skin Treatment, filed Nov. 6, 2019) received from ISA/EP, 5 pages (dated Mar. 27, 2020).
Written Opinion for PCT/US2019/060131 (Systems and Methods for Skin Treatment, filed Nov. 6, 2019) received from ISA/EP, 7 pages (dated Mar. 27, 2020).
Brazilian Office Action dated Feb. 1, 2022 issued in corresponding Brazilian Application No. 112019005312-3, with informal translation to English.
Japanese Office Action dated Jun. 15, 2021 issued in corresponding Japanese Application No. 2019-537035, with English translation.
Alsberg, E. et al., Engineering growing tissues, PNAS, 99(19):12025-12030 (2002).
Banzhaf, C. et al., Spatiotemporal Closure of Fractional Laser-Ablated Channels Imaged by Optical Coherence Tomography and Reflectance Confocal Microscopy, Lasers in Surgery and Medicine, 48:157-165 (2016).
Bedi, V. et al., The effects of pulse energy variations on the dimensions of microscopic thermal treatment zones in nonablative fractional resurfacing, Lasers Surg Med, 39(2):145-55 (2007).
Cevc, Gregor, Drug delivery across the skin, Expert Opinion Investigational Drugs, 6(12):1887-937 (1997).
Chang, Te-Sheng, An updated review of tyrosinase inhibitors, Int J Mol Sci, 10(6):2440-2475 (2009).
International Search Report for International Patent Application No. PCT/US2012/022980 dated Aug. 9, 2012.
International Written Opinion for International Patent Application No. PCT/US2012/022980 dated Aug. 9, 2012.
Czech, Z. et al., Pressure-sensitive adhesives for medical applications, Wide Spectra of Quality Control, Akyar, 309-332 (2011).
de las Heras Alarcon et al., Stimuli responsive polymers for biomedical applications, Chem Soc Rev. 34(3):276-85 (2005).
Dini, G. et al., Grasping leather plies by Bernoulli grippers, CIRP Ann Manuf Technol. 58(1):21-4 (2009).
Dujardin, J. et al., In vivo assessment of skin electroporation using sguare wave pulses, J Control Release, 79(1-3):219-27 (2002).
Dunkin, C. et al., Scarring occurs at a critical depth of skin injury: precise measurement in a graduated dermal scratch in human volunteers, Plast Reconstr Surg, 119(6):1722-32 (2007).
European Patent Office, Supplementary European Search Report, Application No. EP13813955.5, dated Mar. 18, 2016.
Fernandes, J. et al., Micro-mechanical fractional skin rejuvenation, Plast Reconstr Surg, 130(5S-1):28 (2012).
Fernandes, J. et al., Micro-mechanical fractional skin rejuvenation, Plast Reconstr Surg, 131(2):216-23 (2013).
Galaev., 'Smart' polymers in biotechnology and medicine, Russ Chem Rev. 64(5):471-489 (1995).
Glogau, Aesthetic and anatomic analysis of the aging skin, Semin Cutan Med Surg. 15(3):134-8 (1996).
Hale, G. and Querry, M. , Optical constants of water in the 200-nm to 200-microm wavelength region, Appl Opt, 12(3):555-63 (1973).
Han, H. et al., Combined, Minimally Invasive, Thread-based Facelift, Archives of Aesthetic Plastic Surgery, 20(3):160-164 (2014).
Huang, W.M. et al., Shape memory materials, Material Today, 13(7-8):54-61 (2010).
International Preliminary Report on Patentability for International Patent Application No. PCT/US2009/039125, dated Oct. 5, 2010 (6 pages).
International Preliminary Report on Patentability for International Patent Application No. PCT/US2012/022987, dated Jul. 30, 2013 (5 pages).
International Preliminary Report on Patentability for International Patent Application No. PCT/US2012/022993, dated Jul. 30, 2013 (5 pages).
International Preliminary Report on Patentability for International Patent Application No. PCT/US2012/047716, dated Nov. 4, 2014 (4 pages).
International Preliminary Report on Patentability for International Patent Application No. PCT/US2013/049445, dated Jan. 6, 2015 (4 pages).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2009/039125, dated Nov. 16, 2009 (9 pages).
International Search Report and Written Opinion for International Patent Application No. PCT/US2012/022987, dated Apr. 12, 2012 (6 pages).
International Search Report and Written Opinion for International Patent Application No. PCT/US2012/022993, dated May 17, 2012 (6 pages).
International Search Report and Written Opinion for International Patent Application No. PCT/US2012/047716, dated Oct. 25, 2012 (5 pages).
International Search Report and Written Opinion for International Patent Application No. PCT/US2013/049445, dated Oct. 18, 2013 (5 pages).
International Search Report and Written Opinion for International Patent Application No. PCT/US2014/016483, dated May 6, 2014 (9 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (11 pages).
International Search Report and Written Opinion for PCT/US2009/039125 dated Nov. 16, 2009.
International Search Report and Written Opinion for PCT/US2011/035613, dated May 6, 2011.
International Search Report and Written Opinion issued by the Korean Intellectual Property Office as International Searching Authority for International Application No. PCT/US2009/039114 dated Nov. 16, 2009 (10 pages).
International Search Report and Written Opinion under dated Oct. 18, 2013 in connection with PCT/US2013/049445.
International Search Report for International Patent Application No. PCT/US2012/022993 dated May 17, 2012.
International Search Report for PCT/US14/71443, 3 pages (dated Mar. 19, 2015).
International Search Report for PCT/US2014/016483, 3 pages (dated May 6, 2014).
International Search Report for PCT/US2015/060685, 3 pages (dated Feb. 2, 2016).
International Search Report for PCT/US2017/024752, 8 pages (dated Aug. 29, 2017).
International Search Report for PCT/US2017/052528 (Devices and Methods for Cosmetic Skin Resurfacing, filed Sep. 20, 2017), issued by ISA/US, 5 pages (dated Jan. 4, 2018).
International Search Report for PCT/US2017/052539 (Rapid Skin Treatment Using Microcoring, filed Sep. 20, 2017), issued by ISA/US, 7 pages (dated Nov. 22, 2017).
International Searching Report and Written Opinion issued by the Korean Intellectual Property Office as International Search Authority for International Application No. PCT/US2011 /035613 dated Jan. 12, 2012 (6 pages).
International Written Opinion for International Patent Application No. PCT/US2012/022993 dated May 17, 2012.
International Written Opinion or International Patent Application No. PCT/US2012/022987 dated Apr. 12, 2012.
Kakasheva-Mazenkovska, L. et al., Variations of the histomorphological characteristics of human skin of different body regions in subjects of different age, Contributions, 32(2):119-28 (2011).
Konermann, W. et al., Ultrasonographically guided needle biopsy of benign and malignant soft tissue and bone tumors, J Ultrasound Med, 19(7):465-71 (2000).

(56) References Cited

OTHER PUBLICATIONS

Lemperle, G. et al., A Classification of Facial Wrinkles, Plastic and Reconstructive Surgery, 108(6):1735-1750 (2001).
Lien, T.K. and Davis, P.G.G., A novel gripper for limp materials based on lateral Coanda ejectors, CIRP Ann Manuf Technol, 57(1):33-6 (2008).
Majid, Imran, Microneedling therapy in atrophic facial scars: an objective assessment, J Cutan Aesthet Surg. 2(1):26-30 (2009).
Moore, J. et al., Modeling of the Plane Needle Cutting Edge Rake and Inclination Angles for Biopsy, Journal of Manufacturing Science and Engineering, 132:051005-1-051005-8 (2010).
Narins, R. et al., Validated Assessment Scales for the Lower Face, Dermatology Surgery, 38:333-342 (2012).
PCT International Preliminary Report on Patentability, PCT/US2014/036638, dated Nov. 3, 2015, 7 pages.
PCT International Preliminary Report on Patentability, PCT/US2014/050426, dated Feb. 9, 2016, 8 pages.
PCT International Search Report and Written Opinion, PCT/US2014/036638, dated Oct. 2, 2014, 10 pages.
PCT International Search Report and Written Opinion, PCT/US2014/050426, dated Feb. 4, 2015, 18 pages.
Pliquett, U. et al., A propagating heat wave model of skin electroporation, J Theor Biol, 251(2):195-201 (2008).
Prausnitz, M. et al., Electroporation of mammalian skin: a mechanism to enhance transdermal drug delivery, Proc Natl Acad Sci USA, 90(22):10504-8 (1993).
Salam, G. and Amin, J., The basic Z-plasty, Am Fam Physician, 67(11):2329-32 (2003).
Written Opinion for PCT/US14/71443, 4 pages (dated Mar. 19, 2015).
Written Opinion for PCT/US2014/016483, 6 pages (dated May 6, 2014).
Written Opinion for PCT/US2015/060685, 4 pages (dated Feb. 2, 2016).
Written Opinion for PCT/US2017/024752, 11 pages (dated Aug. 29, 2017).
Written Opinion for PCT/US2017/052528 (Devices and Methods for Cosmetic Skin Resurfacing, filed Sep. 20, 2017), issued by ISA/US, 17 pages (dated Jan. 4, 2018).
Written Opinon for PCT/US2017/052539 (Rapid Skin Treatment Using Microcoring, filed Sep. 20, 2017), issued by ISA/US, 8 pages (dated Nov. 22, 2017).
Zhu, J. et al., The Efficacy and Safety of Fractional CO2 Laser Combined with Topical Type A Botulinum Toxin for Facial Rejuvenation: A Randomized Controlled Split-Face Study, BioMed Research International, 7 pages (2016).
Korean Office Action dated Nov. 26, 2021 issued in corresponding Korean Application No. 10-2019-7011167, with English summary.
International Search Report and Written Opinion dated Oct. 18, 2012 issued in corresponding International Application No. PCT/US2012/047708 Previously cited in IDS submitted Aug. 9, 2019—resubmission includes mailing date.
Canadian Office Action dated May 18, 2022 issued in corresponding Canadian Application No. 3037490.
Alkilani et al. "Transdermal Drug Delivery: Innovative Pharmaceutical Developments Based on Disruption of the Barrier Properties of the stratum corneum", Pharmaceutics, vol. 7, No. 4 (Oct. 22, 2015), pp. 438-470.
Dai, et al., Magnetically-Responsive Self Assembled Composites, Chemical Society Reviews, 2010, 39:4057-4066.
Fabi, Noninvasive skin tightening: focus on new ultrasound techniques, Clinical, Cosmetic and Investigative Dermatology, vol. 8 (Feb. 5, 2015), pp. 47-52.
Goldberg et al. "Skin Rejuvenation with Non-Invasive Pulsed Electric Fields", Scientific Reports, vol. 5 (May 12, 2015), p. 1-18.
Lee et al. "Combined Treatment with Botulinum Toxin and 595-nm Pulsed Dye Laser for Traumatic Scarring", Annals of Dermatology, vol. 27, No. 6 (2015), p. 756-758.
Paithankar et al. "Acne Treatment Based on Selective Photothermolysis of Sebaceous Follicles with Topically Delivered Light-Absorbing Gold Microparticles", Journal of Investigative Dermatology, vol. 135 (Apr. 9, 2015) p. 1727-1734.
Wong et al. "Hypopigmentation Induced by Frequent Low-Fluence, Large-Spot-Size QS Nd:YAG Laser Treatments", Annals of Dermatology, vol. 27, No. 6, (2015), p. 751-755.
Japanese Office Action dated Feb. 1, 2022 issued in corresponding Japanese Application No. 2019-537035, with English translation.
Chinese Office Action dated Mar. 23, 2022 issued in corresponding Chinese Application No. 201780069547.9, with English translation.
Dua et al.; Follicular Unit Extraction Hair Transplant; 2010; J Cutan Aesthet Surg. May-Aug. 2010; 3(2):76-81(Year: 2010).
Wikipedia; Subcutaneous tissue; https://en.wi?pedia.org/wiki/Subcutaneous—tissue; originally accessed Oct. 18, 2017; accessed again on Jun. 1, 2022.
Brannon, Heather. "Skin anatomy" Jul. 30, 2004 (updated Dec. 19, 2014), 4 pages. Originally Retrieved from Internet on Jan. 18, 2019. Retrieved again on Jun. 1, 2022. URL: https://web.archive.org/web/20150329121127/http:l/dermatology.about.com/CS/skinanatomy/a/anatomy.htm.
Bolshaya meditsinkaya entsiklopediya, M. 1976, vol. 3, p. 184.
Spravochik Opertsionnoy I Perevyazochnoy Sestrie, M., <<Meditsina>>, 1985, p. 31.
Korean Office Action dated Jun. 3, 2022 issued in corresponding Korean Application No. 10-2019-7011167, with English translation.
Japanese Office Action dated Jul. 5, 2022 issued in corresponding Japanese Application No. 2019-537035, with English translation.

* cited by examiner

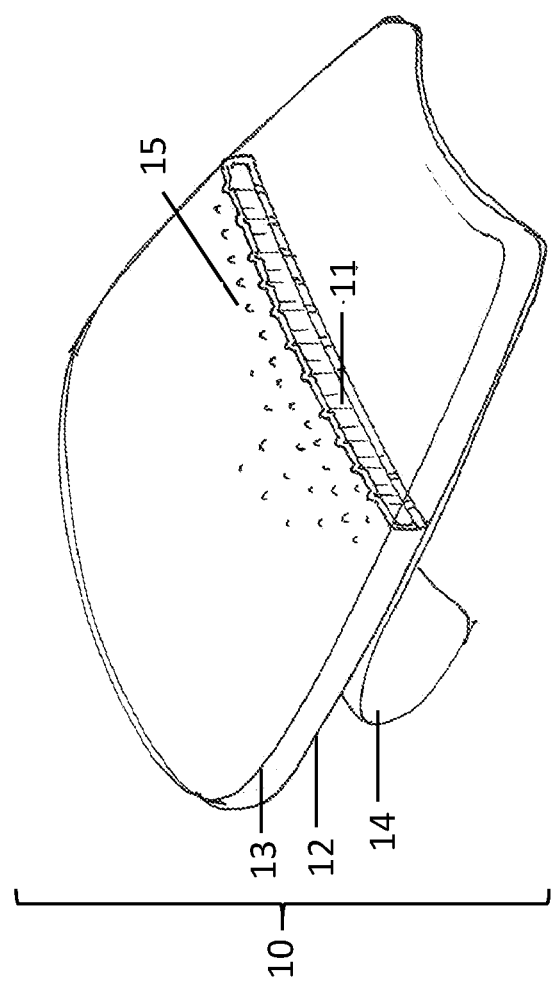

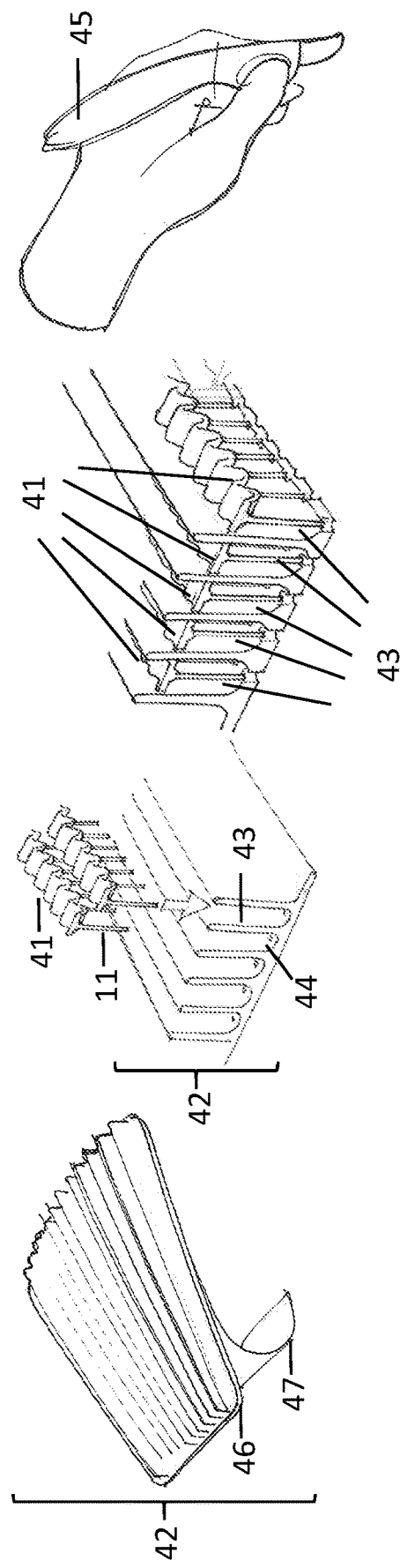

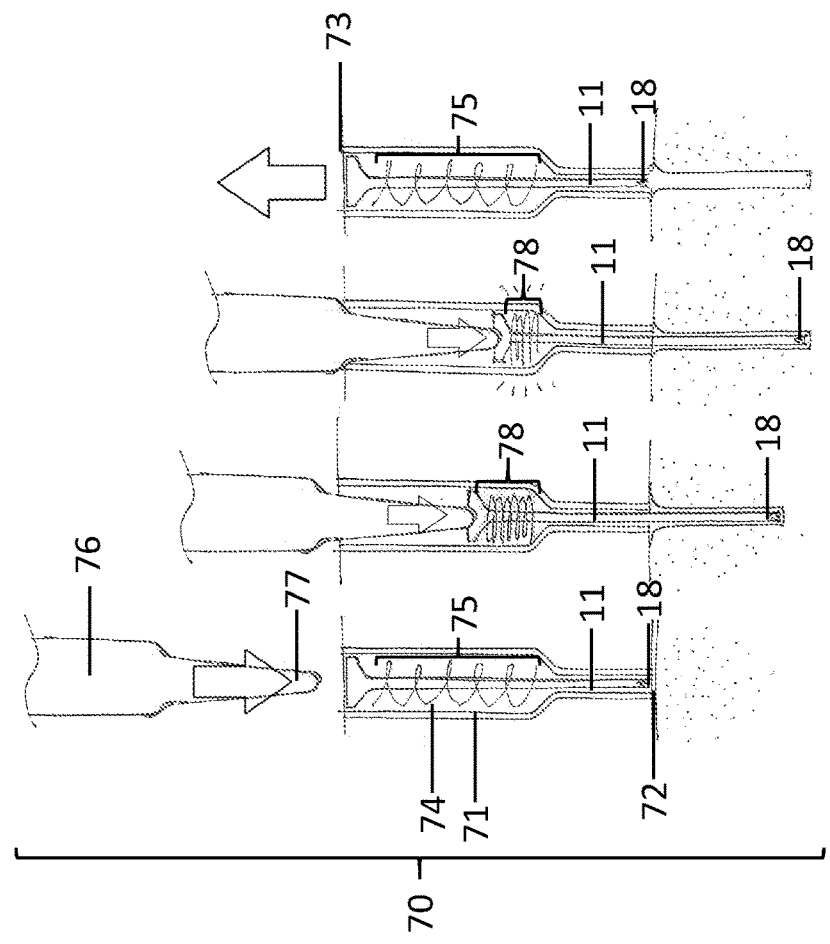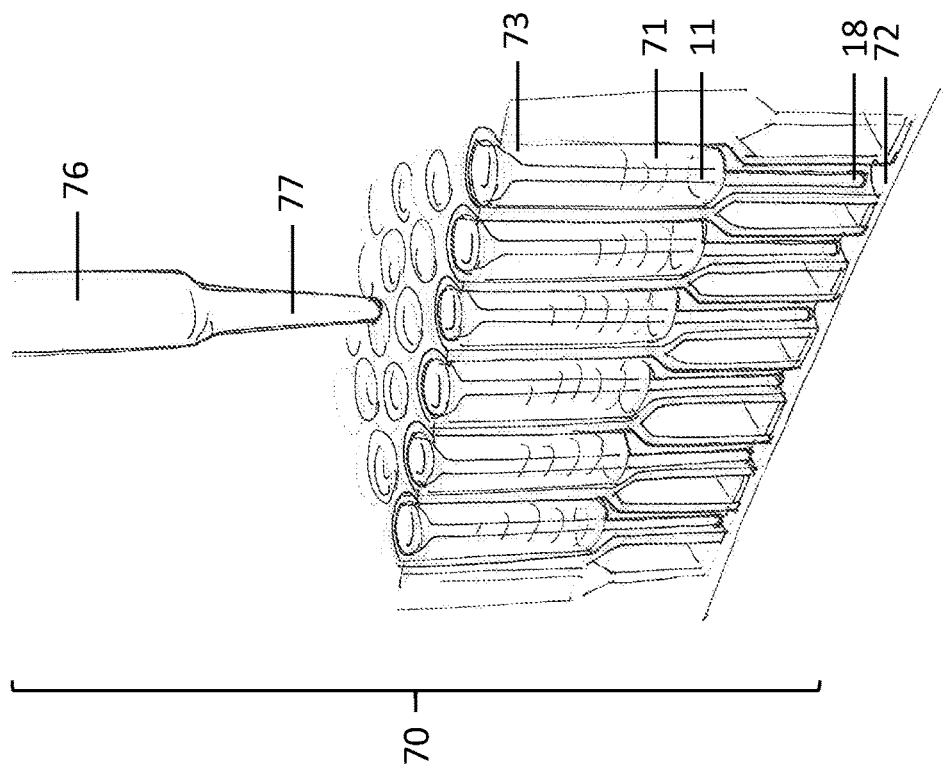

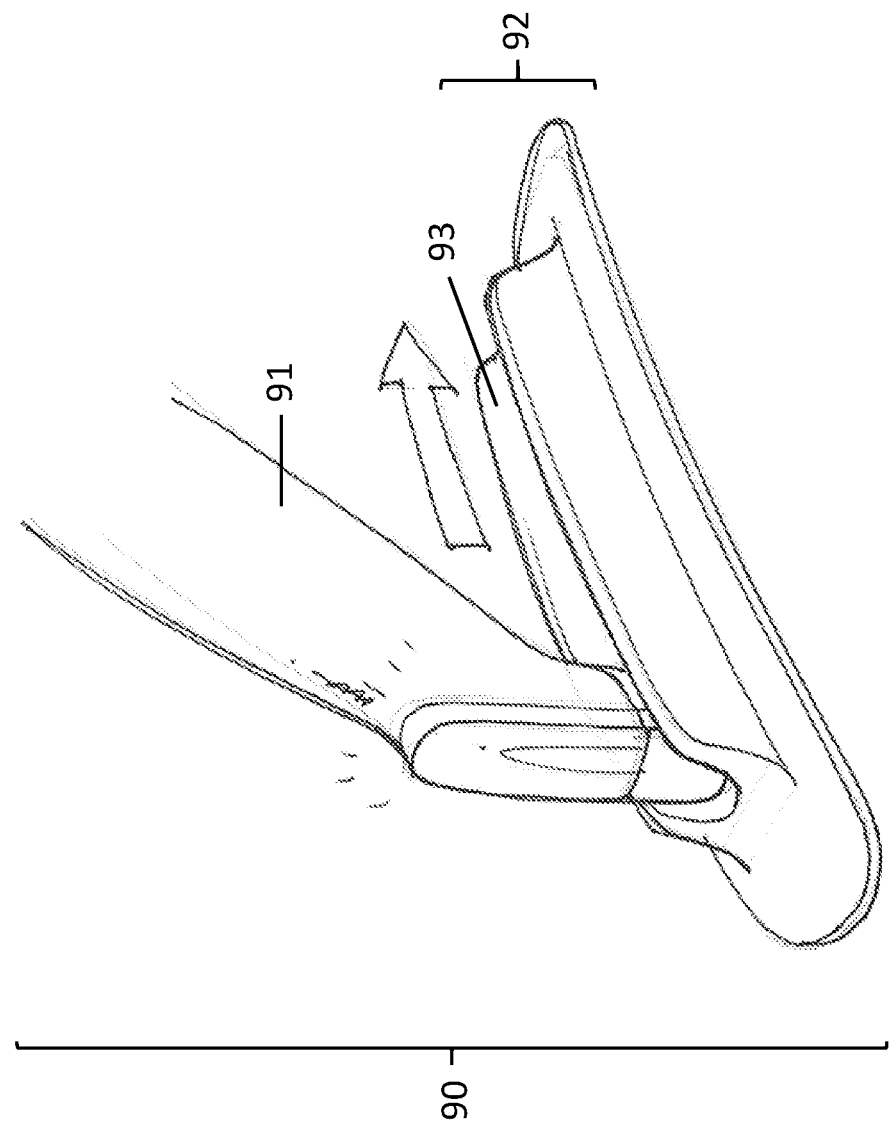

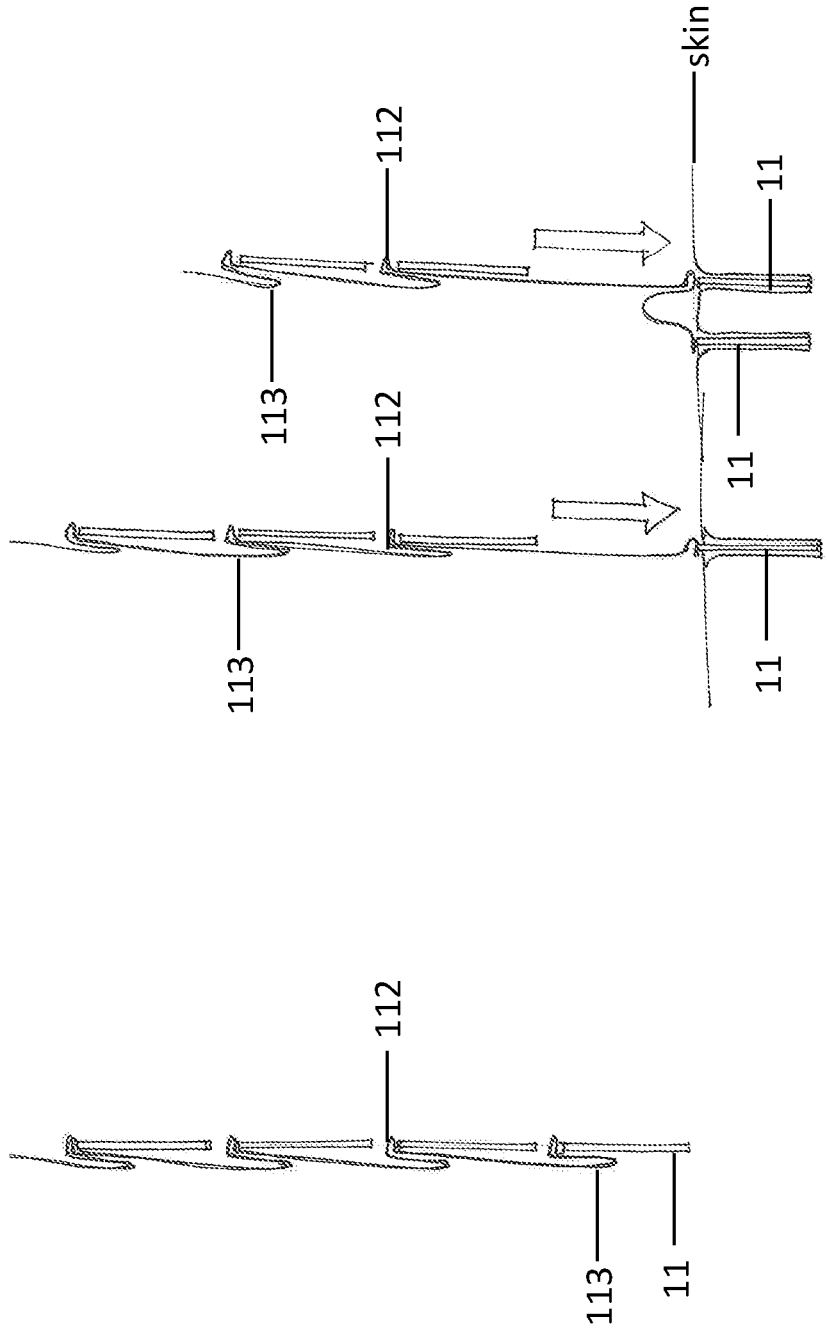

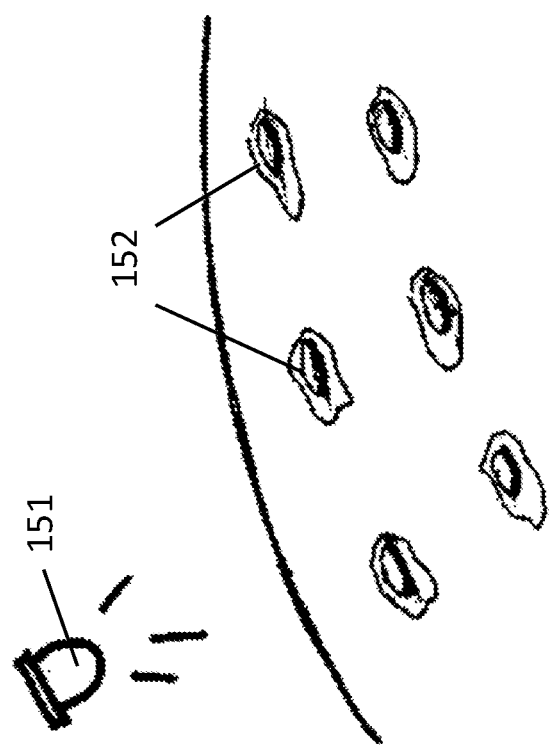

DEVICES AND METHODS FOR COSMETIC SKIN RESURFACING

CROSS REFERENCE TO RELATED APPLICATIONS

This application is a U.S. National Phase Application under 35 U.S.C. § 371 of International Patent Application No. PCT/US2017/052528, filed on Sep. 20, 2017, which claims the benefit of and priority to U.S. Provisional Application No. 62/397,869, filed on Sep. 21, 2016, the entire contents of each of which are hereby incorporated by reference in their entireties.

BACKGROUND OF THE INVENTION

Aesthetic medicine seeks to enhance a patient's satisfaction with their physical appearance, e.g., by eliminating excess unwanted tissue and/or reducing skin laxity. Conventional surgical therapies (e.g., a face lift, brow lift, or breast lift) can be effective but are often invasive, inconvenient, and expensive. In addition, scarring resulting from surgical therapies limits the applicability of surgery to certain treatment sites.

Although minimally invasive methods are available, such methods are generally less effective than surgical methods. For example, methods using energy sources (e.g., laser, non-coherent light, radiofrequency, and ultrasound) can be effective at improving the architecture and texture of the skin but are less effective at tightening the skin. In addition, tissue ablative methods that create micro-ablations with photo-thermal energy can generate a coagulation zone in tissue that interferes with closure of the ablation zones, thereby inhibiting tissue tightening. These methods also require longer patient healing times due to the biological reparative response to coagulated and dead tissue during the remodeling process. Also, laser ablation depth is typically limited by the depth of the laser beam focus. Ablation of deeper tissue layers than is possible with available laser systems is desirable for the treatment of scars, for example.

Other methods, such as the use of neurotoxins, for example, botulinum toxin, reduce the formation of dynamic wrinkles by paralysis of the injected muscles, but such toxins have minimal or no direct effect on skin tightness or laxity. Finally, dermal fillers, such as hyaluronic acid, can be injected in the dermal layer to smooth out wrinkles and improve contours, but such fillers do not directly tighten or reduce laxity of the skin. Thus, surgical therapies remain the gold standard for lifting and/or tightening skin, as compared to energy-based techniques (e.g., laser, radiofrequency, and ultrasound) and injection-based techniques (e.g., botulinum toxin and fillers such as hyaluronic acid- and collagen-based fillers).

SUMMARY OF THE INVENTION

There is a need for improved methods and devices for cosmetic resurfacing that provide increased effectiveness over currently available techniques while maintaining convenience, affordability, and accessibility to patients desiring skin rejuvenation.

This invention relates to technologies, devices (e.g., needles (e.g., hollow needles), staples (e.g., hollow staples), articles, apparatuses, and systems), kits, and methods for cosmetic resurfacing of skin tissue. The technologies, devices, kits, and methods described herein may be used to generate a cosmetic effect in the skin tissue (e.g., by removing tissue portions from the skin and/or by triggering biological responses that contribute to tissue remodeling and new skin tissue formation).

In one aspect, the invention features an article for producing a cosmetic effect in a skin tissue. In some embodiments, an article includes: a) first and second layers; and b) a plurality of solid or hollow needles affixed between first and second layers, wherein the article is constructed and arranged so that needles can adopt at least two positions relative to layers, wherein the at least two positions include a retracted position and a protracted position.

In some embodiments, a first layer includes a plurality of openings and tips of needles are aligned with openings in a first layer when the needles are in the retracted position.

In some embodiments, when needles are extended to a protracted position, tips of needles are configured to extend through openings in a first layer and to insert into skin tissue when an article is in contact with skin tissue.

In some embodiments, one or more needles are hollow (e.g., a hollow needle configured to remove a portion of skin tissue when extended into and extracted from skin tissue).

In some embodiments, each needle is in contact with a tensioner that is configured to hold needles in a retracted position. In some embodiments, each needle is in contact with a tensioner that is configured to restore needles to a retracted position after needles are extended to a protracted position.

In some embodiments, at least a portion of a first layer further includes an adhesive material. A first layer may further include a releasable backing material that covers, and can be removed to expose, adhesive material. In some embodiments, adhesive material is a pressure sensitive adhesive (PSA), a non-reactive adhesive, a contact adhesive, a hot melt adhesive, a reactive adhesive, a one-part adhesive, a natural adhesive, or a synthetic adhesive. In some embodiments, the adhesive material is an elastomer, a thermoplastic, an emulsion, or a thermoset. In some embodiments, the adhesive material is an acrylic, a synthetic or natural rubber, an ethylene-vinyl acetate (EVA), a nitrile, a silicone (e.g., a siliconized material), a styrene block copolymer, or a vinyl ether.

In some embodiments, at least a portion of the first layer further includes a texture configured to reduce movement along the skin tissue. The texture may include hooks, bumps, ridges, or grooves.

In some embodiments, a second layer includes a plurality of protrusions, wherein the second layer includes a plurality of protrusions, wherein each protrusion indicates a location of a single one of a plurality of needles, and wherein protrusions are configured to be pushed down to extend needles to a protracted position.

In some aspects, the invention features an article for producing a cosmetic effect in a skin tissue that includes a) a layer; and b) a plurality of solid or hollow needles, wherein the plurality of needles are affixed onto a surface of a layer at proximal ends of needles.

In some embodiments, needles are configured to insert into skin tissue when an article is applied onto skin tissue. In some embodiments, one or more of the needles in an article are hollow. In some embodiments, hollow needle or needles are configured to remove a portion of skin tissue when an article is removed from skin tissue.

In some embodiments, each needle is in contact with a tensioner that is configured to hold needles in a retracted position.

In some embodiments, each needle is in contact with a tensioner that is configured to restore needles to a retracted position after the needles are extended to a protracted position.

In some embodiments, at least a portion of a layer of an article further includes an adhesive material. In some embodiments, an article further includes a releasable backing material that covers, and can be removed to expose, an adhesive material. In some embodiments, an adhesive material is a pressure sensitive adhesive (PSA), a non-reactive adhesive, a contact adhesive, a hot melt adhesive, a reactive adhesive, a one-part adhesive, a natural adhesive, or a synthetic adhesive. In some embodiments, the adhesive material is an elastomer, a thermoplastic, an emulsion, or a thermoset. In some embodiments, the adhesive material is an acrylic, a synthetic or natural rubber, an ethylene-vinyl acetate (EVA), a nitrile, a silicone, a styrene block copolymer, or a vinyl ether. In some embodiments, an adhesive material is a siliconized material.

In some embodiments, at least a portion of a layer further comprises a texture configured to reduce movement along skin tissue. In some embodiments, a texture comprises hooks, bumps, ridges, or grooves.

In some embodiments, an article is shaped to maintain a close proximity to skin tissue by way of suction. An article may be shaped to conform to contours of skin tissue.

In some embodiments, skin tissue is an eyelid, a cheek, a chin, a forehead, a lip (e.g., an upper lip), a nose, a neck, a chest, a breast, an arm, a hand, a leg, an abdomen, and/or a back.

In some embodiments, an article is in the form of a tape or a patch. An article may be stretchable.

In some embodiments, an article is configured to produce a pattern on skin tissue. A pattern may include one or more rows or a semi-random spatial distribution.

In some embodiments, a hollow needle or needles in the article are configured to remove an areal fraction of the skin tissue that is between about 0.01 to about 0.65 (e.g., between about 0.05 and 0.2; between about 0.05 and 0.1; between about 0.01 to about 0.05; between about 0.02 to about 0.03).

In some embodiments, needles in an article are configured for single use. In some embodiments, an entire article is configured for single use.

In some aspects, the invention features a system including an article described herein and an applicator, wherein the applicator is configured to contact at least one of a plurality of needles, whereby pressure from the applicator on a needle extends one or more needles to a protracted position.

In some embodiments, an applicator is coated with a lubricant.

In some aspects, the invention features a method for producing a cosmetic effect in a skin tissue of a subject by applying an article described herein or a system described herein, on skin tissue, translating needles in an article or system from a retracted position to a protracted position, thereby inserting needles into skin tissue, and removing needles from skin tissue.

In some embodiments, needles are hollow needles. In some embodiments, portions of skin tissue are removed by hollow needles. In some embodiments, a method produces a plurality of holes in the skin tissue.

In some embodiments, a releasable backing material that covers an adhesive material on an article described herein may be removed prior to applying an article on skin tissue.

In some embodiments, skin tissue is an eyelid, a cheek, a chin, a forehead, a lip (e.g., an upper lip), a nose, a neck, a chest, a breast, an arm, a hand, a leg, an abdomen, and/or a back.

In some embodiments, removing needles from skin tissue includes extracting needles by moving needles from a protracted position to a retracted position. In some embodiments, removing needles from skin tissue includes removing an article from skin tissue.

In some aspects, the invention features a system for producing a cosmetic effect in a skin tissue that includes (a) a plurality of solid or hollow needles; and (b) a template including a plurality of openings, wherein the plurality of openings are configured to engage with a plurality of needles.

In some embodiments, a template includes at least one trough, wherein the trough includes a plurality of openings, and wherein the template is configured for contact with skin tissue by the trough.

In some embodiments, a plurality of needles are configured in a strip (e.g., arranged in a row on a strip). A strip may include a plurality of corrugations, and corrugations may include peaks and grooves. In some embodiments, needles are affixed within grooves.

In some embodiments, a strip is configured for engagement with a trough in a template such that one needle in a strip is configured to engage with one opening in a template.

In some embodiments, a needle, in a first position, includes a tip that is aligned with one opening in a template.

In some embodiments, the system further includes an applicator, wherein the applicator is configured to apply pressure on a strip, thereby translating a needle from a first position to a second position, whereby a tip of the needle extends beyond an opening in a template and inserts into skin tissue. In some embodiments, an applicator is coated with a lubricant.

In some embodiments, a template includes: (a) a first layer including a plurality of openings in at least one row; (b) a second layer including at least one track; and (c) a receptacle disposed inside a track, wherein the plurality of needles are affixed between first and second layers and tips of the needles are configured to engage with openings.

In some embodiments, a first layer of a template includes a plurality of openings in one to ten rows. In some embodiments, a template is configured for contact with skin tissue by a first layer.

In some embodiments, when a template is in contact with skin tissue, a plurality of needles are configured to extend from a first position, in which tips of needles are aligned with openings in a first layer, to a second position, in which tips of needles extend through openings in a template, allowing them to insert into skin tissue.

In some embodiments, a system further includes an applicator, wherein an applicator is configured to fit inside a receptacle and to engage with one needle.

In some embodiments, a receptacle is configured to translate along a track.

In some embodiments, a template includes a plurality of sleeves, wherein each sleeve includes a first opening at one end thereof. Each needle may be slidably mounted inside each sleeve. A tensioner (e.g., a spring) may be further included inside each sleeve, wherein the tensioner is configured to engage with a needle inside a sleeve.

In some embodiments, a system further includes an applicator, wherein the applicator is configured to fit inside a sleeve and to engage with a tensioner and/or a needle inside a sleeve.

In some embodiments, each needle is configured to be in a retracted position, in which a tip of each needle is aligned with a first opening in a sleeve.

In some embodiments, an applicator is configured to i) translate a needle from a retracted position to a protracted position, in which a tip of a needle extends beyond a first opening in a sleeve, and ii) compress a tensioner as a needle translates to the protracted position.

In some embodiments, a tensioner is configured to decompress, thereby translating a needle from a protracted position back to a retracted position upon release by an applicator.

In some embodiments, one or more of the needles are hollow (e.g., a hollow needle is configured to remove a portion of skin tissue when extended into and extracted from skin tissue).

In some embodiments, a system is configured to produce a pattern on skin tissue. A pattern may include one or more rows or a semi-random spatial distribution.

In some embodiments, a hollow needle or needles are configured to remove an areal fraction of skin tissue that is between about 0.01 to about 0.65 (e.g., between about 0.05 and 0.2; between about 0.05 and 0.1; between about 0.01 to about 0.05; between about 0.02 to about 0.03).

In some embodiments of the system described herein, needles in a system are configured for single use. In some embodiments, a strip in a system is configured for single use.

In some aspects, the invention features a strip for producing a cosmetic effect in a skin tissue including a plurality of needles affixed to a strip. A plurality of needles may be arranged in a row on a strip. A strip may include a plurality of corrugations, and corrugations may include peaks and grooves. In some embodiments, needles are affixed within grooves.

In some embodiments, one or more needles are hollow.

In some embodiments, a strip is configured for single use.

In some aspects, the invention features a method for producing a cosmetic effect in a skin tissue of a subject by applying a system or a strip described herein on skin tissue, translating needles in a system or a strip from a retracted position to a protracted position, thereby inserting needles into skin tissue, and removing needles from skin tissue.

In some embodiments, needles are hollow needles. Portions of skin tissue may be removed by hollow needles.

In some embodiments, a method produces a plurality of holes in skin tissue.

In some embodiments, removing needles from skin tissue includes extracting needles from a first position to a second position or from a protracted position to a retracted position.

In some aspects, the invention features a system for producing a cosmetic effect in a skin tissue that includes: a) a guide rail (e.g., a guide rail that includes a plurality of openings; b) a main body configured for handheld operation; c) one or more solid or hollow needles mounted inside a main body (e.g., detachably mounted inside a main body); and d) a tensioner mounted inside a main body and configured to engage with a needle, wherein a main body is configured to slide along a guide rail.

In some embodiments, a main body further includes a position sensor.

In some embodiments, a guide rail includes a raised backbone.

In some embodiments, a main body includes a trough at a first end of a main body, wherein the trough is configured to fit on top of a raised backbone of a guide rail as the main body slides along a guide rail.

In some embodiments, a raised backbone of a guide rail includes at least one indentation and wherein the indentation can be detected by a position sensor in a main body.

In some embodiments, a guide rail includes a trough. A trough may include at least one indentation and wherein the indentation can be detected by a position sensor in a main body.

In some embodiments, a tensioner is configured to place a needle in a retracted position, in which a tip of a needle is aligned with a first end of a main body, and/or in a protracted position, in which a tip of a needle extends beyond a first end of a main body.

In some embodiments, a system is configured to produce a pattern on skin tissue. A pattern may include one or more rows or a semi-random spatial distribution.

In some embodiments, a needle is a hollow needle (e.g., a hollow needle is configured to remove a portion of skin tissue).

In some embodiments, a hollow needle is configured to remove an areal fraction of skin tissue that is between about 0.01 to about 0.65 (e.g., between about 0.05 and 0.2; between about 0.05 and 0.1; between about 0.01 to about 0.05; between about 0.02 to about 0.03).

In some embodiments, needles in a system are configured for single use.

In some aspects, the invention features a guide rail configured to contact skin tissue. A guide rail may include a plurality of openings and is configured for mounting by a main body, wherein the main body includes: a) a needle detachably mounted inside a main body; and b) a tensioner mounted inside a main body and configured to engage with a needle, wherein a main body is configured for handheld position and to slide along a guide rail.

In some embodiments, a guide rail includes a raised backbone. A raised backbone may include at least one indentation.

In some embodiments, a guide rail includes a trough. A trough may include at least one indentation.

In some embodiments, a main body further includes a position sensor, which is configured to detect an indentation in a raised backbone or a trough of a guide rail.

In some embodiments, a main body further includes a trough at a first end of a main body, wherein the trough is configured to fit on top of a raised backbone of a guide rail as a main body slides along a guide rail.

In some embodiments, a needle is a hollow needle.

In some aspects, the invention features a main body for producing a cosmetic effect in a skin tissue of a subject that includes: a) a needle detachably mounted inside a main body; and b) a tensioner mounted inside a main body and configured to engage with a needle, wherein a main body is configured for handheld position and to slide along a guide rail, and wherein a guide rail includes a plurality of openings.

In some embodiments, a main body further includes a trough at a first end of a main body.

In some embodiments, a guide rail includes a raised backbone and a raised backbone may be configured to engage with a trough at a first end of a main body. A raised backbone may include at least one indentation.

In some embodiments, a guide rail includes a trough. A trough may include at least one indentation.

In some embodiments, a main body further includes a position sensor and wherein the position sensor is configured to detect an indentation.

In some embodiments, a needle is a hollow needle.

In some aspects, the invention features a method for producing a cosmetic effect in a skin tissue of a subject that includes applying a system including a guide rail and a main body comprising a needle and a tensioner to skin tissue, translating a needle in a system or a main body from a retracted position to a protracted position, thereby inserting a needle into skin tissue, and removing a needle from skin tissue.

In some embodiments, a needle is a hollow needle. Portions of skin tissue may be removed by a hollow needle. In some embodiments, a method produces a plurality of holes in skin tissue.

In some aspects, the invention features a device for producing a cosmetic effect in a skin tissue that includes a main body configured for handheld operation, wherein a main body includes a support base including a plurality of needles or staples affixed thereto, wherein a main body is configured to engage a support base, thereby ejecting a support base including a plurality of needles or staples, and wherein needles or staples insert into skin tissue when in contact therewith.

In some embodiments, a support base may be at least one inflatable bladder. In some embodiments, an inflatable bladder is in a collapsed form and needles or staples are configured to insert into skin tissue over a first surface of an inflatable bladder.

In some embodiments, an inflatable bladder is configured to inflate, whereby needles or staples are withdrawn from skin tissue. In some embodiments, needles or staples are affixed onto a first surface of an inflatable bladder.

In some embodiments, a second surface of a support base includes an adhesive material, wherein the adhesive material is a substantially non-releasable adhesive material. A second surface of a support base may include a release backing material that covers, and can be removed to expose, an adhesive material. In some embodiments, a release backing material includes a siliconized material.

In some embodiments, when a support base is at least one inflatable bladder, a main body includes a plurality of staples.

In some embodiments, a support base may be a folded tape including multiple folded ledges and a plurality of needles or staples may be affixed onto folded ledges of a folded tape.

In some embodiments, a first surface of a support base further includes an adhesive material, wherein the adhesive material is a substantially non-releasable adhesive material.

In some embodiments, when a support base is a folded tape including multiple folded ledges, a main body includes a plurality of needles.

An adhesive material may be a pressure sensitive adhesive (PSA), a non-reactive adhesive, a contact adhesive, a hot melt adhesive, a reactive adhesive, a one-part adhesive, a natural adhesive, or a synthetic adhesive. An adhesive material may be an elastomer, a thermoplastic, an emulsion, or a thermoset. The adhesive material may be an acrylic, a synthetic or natural rubber, an ethylene-vinyl acetate (EVA), a nitrile, a silicone, a styrene block copolymer, or a vinyl ether.

In some embodiments, a device is configured to produce a pattern on skin tissue. A pattern may include one or more rows or a semi-random spatial distribution.

In some embodiments, one or more of needles or staples in a plurality of needles or staples are hollow. In some embodiments, one or more hollow needles or staples are configured to remove an areal fraction of skin tissue that is between about 0.01 to about 0.65 (e.g., between about 0.05 and 0.2; between about 0.05 and 0.1; between about 0.01 to about 0.05; between about 0.02 to about 0.03).

In some embodiments, needles in a system are configured for single use. In some embodiments, a support base comprising a plurality of needles or staples is configured for single use.

In some aspects, the invention features a method for producing a cosmetic effect in a skin tissue of a subject by contacting a device including a support base and a plurality of needles (e.g., hollow needles) or staples (e.g., hollow staples) to skin tissue, ejecting one or more needles or staples into skin tissue, and removing needles or staples from skin tissue.

In some embodiments, needles or staples are hollow. Portions of skin tissue may be removed by hollow needles or staples.

In some embodiments, a method produces a plurality of holes in skin tissue.

In some aspects, the invention features an apparatus for producing a cosmetic effect in a skin tissue that includes: a) a first paddle comprising a distal end and a proximal end, wherein the distal end comprises an inner surface and an outer surface; b) a second paddle comprising a distal end and a proximal end, wherein the distal end comprises an inner surface and an outer surface; c) a plurality of needles attached to a first paddle; and d) a handle connecting proximal ends of first and second paddles, wherein distal ends of first and second paddles are configured to press together to contact skin tissue.

In some embodiments, a plurality of needles are embedded between inner and outer surfaces of a first paddle. In some embodiments, a plurality of needles are affixed to an inner surface of a first paddle at proximal ends of needles.

In some embodiments, when distal ends of first and second paddles are pressed together to contact skin tissue, an inner surface of a first paddle and an inner surface of a second paddle are configured to be in contact with skin tissue.

In some embodiments, an inner surface of a first paddle includes a plurality of openings.

In some embodiments, needles are configured to be translated from a first position, in which tips of needles are aligned with openings in an inner surface of a first paddle, to a second position, in which tips of needles extend through openings in an inner surface of a first paddle, whereby needles insert into skin tissue.

In some embodiments, skin tissue is an eyelid.

In some embodiments, an inner surface of a first paddle is configured to be in contact with an outer skin surface of an eyelid and an inner surface of a second paddle is configured to be in contact with an inner surface of an eyelid.

In some embodiments, needles are configured to be translated from a first position to a second position, in which tips of the needles extend through openings in an inner surface of a first paddle, whereby needles insert into an outer surface of an eyelid.

In some embodiments, skin tissue is a lip (e.g., an upper lip).

In some embodiments, an inner surface of a first paddle is configured to be in contact with an outer skin surface of a lip and an inner surface of a second paddle is configured to be in contact with an inner surface of a lip.

In some embodiments, needles are configured to be translated from a first position to a second position, in which tips of needles extend through openings in an inner surface of the a paddle, whereby needles insert into an outer surface of a lip.

In some embodiments, first and second paddles are configured to be manually controlled by a handle.

In some embodiments, one or more needles are hollow (e.g., a hollow needle is configured to remove a portion of skin tissue).

In some embodiments, an apparatus is configured to produce a pattern on skin tissue. A pattern may include one or more rows or a semi-random spatial distribution.

In some embodiments, one or more hollow needles are configured to remove an areal fraction of skin tissue that is between about 0.01 to about 0.65 (e.g., between about 0.05 and 0.2; between about 0.05 and 0.1; between about 0.01 to about 0.05; between about 0.02 to about 0.03).

In some embodiments, needles in a first paddle are configured for single use. In some embodiments, an entire apparatus is configured for single use.

In some aspects, the invention features a method for producing a cosmetic effect in a skin tissue of a subject by applying an apparatus described herein on skin tissue, pressing first and second paddles together to contact skin tissue, translating needles in an apparatus from a first position in a first paddle to a second position, thereby inserting needles into the tissue, and removing needles from skin tissue.

In some embodiments, needles are hollow needles. Portions of skin tissue may be removed by hollow needles. In some embodiments, a method produces a plurality of holes in skin tissue.

In some embodiments, removing the needles from skin tissue includes translating needles from a second position to a first position. In some embodiments, removing needles from skin tissue includes depressing first and second paddles, thereby releasing skin tissue.

In some embodiments, skin tissue is an eyelid or a lip (e.g., an upper lip).

In some aspects, the invention features an article for producing a cosmetic effect in a skin tissue, comprising: a) a layer; and b) a plurality of solid or hollow needles, wherein the plurality of needles are partially disposed within a layer at distal ends of needles.

In some embodiments, needles are configured to insert into skin tissue when an article is applied onto the skin tissue.

In some embodiments, one or more needles are hollow.

In some embodiments, one or more hollow needles are configured to remove a portion of skin tissue when an article is removed from skin tissue.

In some embodiments, each needle is in contact with a tensioner that is configured to hold needles in a retracted position.

In some embodiments, each needle is in contact with a tensioner that is configured to restore needles to a retracted position after needles are extended to a protracted position.

In some embodiments, at least a portion of a layer further comprises an adhesive material.

In some embodiments, an article comprises a releasable backing material that covers, and can be removed to expose, an adhesive material.

In some embodiments, an adhesive material is a pressure sensitive adhesive (PSA), a non-reactive adhesive, a contact adhesive, a hot melt adhesive, a reactive adhesive, a one-part adhesive, a natural adhesive, or a synthetic adhesive.

In some embodiments, an adhesive material is an elastomer, a thermoplastic, an emulsion, or a thermoset.

In some embodiments, an adhesive material is an acrylic, a synthetic or natural rubber, an ethylene-vinyl acetate (EVA), a nitrile, a silicone, a styrene block copolymer, or a vinyl ether.

In some embodiments, an adhesive material is a siliconized material.

In some embodiments, at least a portion of a layer further comprises a texture configured to reduce movement along skin tissue.

In some embodiments, a texture comprises hooks, bumps, ridges, or grooves.

In some embodiments, an article is shaped to maintain a close proximity to skin tissue by way of suction.

In some embodiments, an article is shaped to conform to contours of skin tissue.

In some embodiments, skin tissue is an eyelid, a cheek, a chin, a forehead, a lip, a nose, a neck, a chest, a breast, an arm, a hand, a leg, an abdomen, and/or a back.

In some embodiments, an article is in the form of a tape or a patch.

In some embodiments, an article is stretchable.

In some embodiments, an article is configured to produce a pattern on skin tissue.

In some embodiments, a pattern comprises one or more rows or a semi-random spatial distribution.

In some embodiments, one or more hollow needles are configured to remove an areal fraction of skin tissue that is between about 0.01 to about 0.65.

In some embodiments, one or more hollow needles are configured to remove an areal fraction of skin tissue that is between about 0.05 and 0.2.

In some embodiments, one or more hollow needles are configured to remove an areal fraction of tissue that is between about 0.01 to about 0.05.

In some embodiments, one or more hollow needles are configured to remove an areal fraction of skin tissue that is between about 0.02 to about 0.03.

In some embodiments, needles are configured for single use.

In some embodiments, an article is configured for single use.

Definitions

By "tissue portion" is meant that portion of skin and/or proximal tissue layers (e.g., epidermal layer, dermal layer, and subcutaneous fat layer) that is removed (e.g., as a plug) by a hollow needle or hollow staple described herein. A tissue portion may have particular dimensions, geometry, and other characteristics that correspond to the particular dimensions, geometry, and other characteristics of a hollow needle or hollow staple.

By removal of a tissue portion that is "substantially intact" is meant that the tissue portion that is removed from the lumen of a hollow needle or hollow staple remains as an unbroken or whole tissue portion (e.g., the removed tissue portion has not been substantially broken or separated into individual, smaller pieces or macerated).

By "about" is meant, as applied to one or more values of interest, a value that is similar to a stated reference value. In certain embodiments, the term or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

By "subject" is meant a mammal (e.g., a human or non-human mammal).

By "proximal" or "proximal end" is meant the end of the needle (e.g., a hollow needle) that is away from or opposite a needle tip.

By "distal" or "distal end" is meant the end of the needle (e.g., a hollow needle) that is at or close to a needle tip.

By "tensioner" is meant a mechanical component in a device, article, apparatus, or system described herein that is configured to apply a force to create or maintain tension. For example, a tensioner may be configured to be engaged, either directly or indirectly, with a needle (e.g., a hollow needle) or staple (e.g., a hollow staple) in a device, article, apparatus, or system described herein. The force applied by the tensioner can be used to translate the needle or the staple from a retracted position to a protracted position and/or from a protracted position to a retracted position. Examples of tensioners include springs, elastic bands (e.g., a rubber band), and snap domes.

By "semi-random" is meant a pattern or spatial distribution of holes in skin created by one or more of needles (e.g., hollow needles) or staples (e.g., hollow staples) in a device, article, apparatus, or system described herein. For example, a semi-random spatial distribution may include multiple rows of holes, in which the rows of holes are placed without regularity or uniformity over all or a portion of the skin.

By "coring rate" is meant the percentage of hollow needle or hollow staple actuations (entry into skin tissue) that result in cored tissue removal from the treatment area out of the total number of hollow needle or hollow staple actuations.

By "coring force" is meant the force applied by the hollow needle or hollow staple to the cored tissue portion as the needle or staple is being withdrawn from the skin. The coring force is determined by, e.g., the friction between the lumen wall of the hollow needle or hollow staple and the cored tissue portion as the needle or staple is being withdrawn from the skin and the position, geometry, and orientation of micro-features in the hollow needle.

By "insertion force" is meant the force generated by the needle (e.g., a hollow needle) or staple (e.g., a hollow staple) on the skin as it is inserted into the skin. The insertion force is initially determined by the amount of force required to penetrate the tissue. Once the tissue is penetrated, the insertion force is determine by the friction between the needle or staple walls (inner and outer) and the surrounding tissue, as well as the force required to separate the tissue at the tip of the needle or staple.

By "retraction force" is meant the force needed to withdraw the needle (e.g., a hollow needle) or staple (e.g., a hollow staple) from the skin. The retraction force is determined by, e.g., the depth of needle or staple insertion and the friction between the needle or staple walls (inner and outer) and the surrounding tissue. For a hollow needle or a hollow staple, the retraction force is also determined by the force required to separate the tissue portion in the lumen of the hollow tissue or the hollow staple from the surrounding tissue.

Other features and advantages of the invention will be apparent from the following Detailed Description and the claims.

DESCRIPTION OF THE DRAWINGS

FIG. 1A is a schematic illustration showing article 10 containing needles 11 (e.g., hollow needles).

FIG. 1B shows a needle (e.g., a hollow needle) in a retracted position. FIG. 1C shows a needle (e.g., a hollow needle) in a protracted position.

FIG. 2B is a schematic illustration showing template 42 in folded form.

FIG. 2C is a schematic illustration showing strip 41 being assembled into template 42.

FIG. 2D is a schematic illustration showing strip 41 nested into template 42.

FIG. 2E is a schematic illustration showing applicator 45 configured for handheld operation.

FIG. 4A is a schematic illustration showing system 70 including sleeve 71, needles 11 (e.g., hollow needles), and applicator 76.

FIG. 4B is a schematic illustration showing cross-sectional views of system 70 of FIG. 4A in different stages of operation.

FIG. 6A is a schematic illustration showing system 90 including main body 91 and guide rail 92 featuring trough 93.

FIGS. 8B, 8C, and 8D are schematic illustrations showing folded tape 111 featuring needles 11 (e.g., hollow needles) affixed to ledge 112.

FIG. 11 is a drawing showing positions for needle insertion on the skin tissue marked by UV-sensitive material 152 and apparent from UV light 151.

DETAILED DESCRIPTION OF THE INVENTION

Figure 1C:
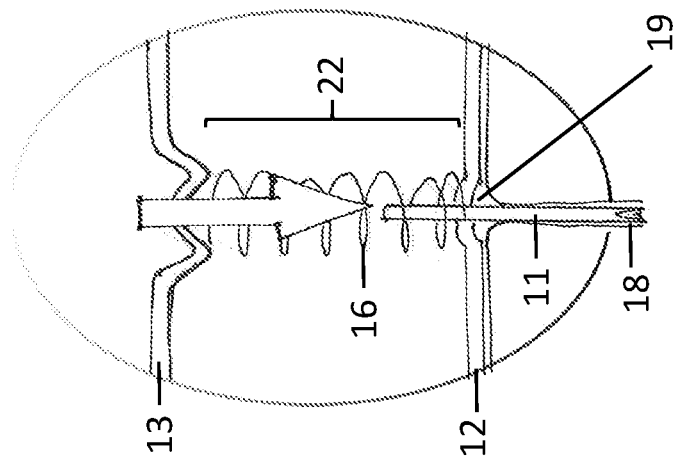
FIGS. 1B and 1C are schematic illustrations showing cross-sectional views of the article in FIG. 1A.

Described herein are technologies, devices (e.g., needles (e.g., hollow needles), staples (e.g., hollow staples), articles, apparatuses, and systems), kits, and methods for generating a cosmetic effect in skin (e.g., by eliminating tissue volume, tightening skin, and/or reducing skin laxity). Without being bound by theory, technologies, devices and/or methods facilitate skin remodeling by debulking the skin tissue (e.g., removing tissue portions from the skin) and/or by triggering biological responses that contribute to tissue resurfacing and remodeling. In particular, described herein are technologies articles, apparatuses, and systems having one or more hollow needles or hollow staples capable of coring tissue portions by capturing and retaining the tissue portions inside the lumen of the hollow needle or the hollow staple after the hollow needles or hollow staples are inserted and withdrawn from the skin. Cored tissue portions may be removed from the lumen of a hollow needle or a hollow staple and discarded, e.g., if a hollow needle or hollow staple is configured for repeated insertion/extraction into/from skin tissue. Technologies, devices and/or methods described herein can be used repeatedly to generate multiple cored skin tissue portions, in particular over a desired area of skin or at chosen sites of a body of a subject. Alternatively, the hollow needle or the hollow staple may be configured for single use. A hollow needle or hollow staple may retain cored tissue portions in a lumen and be discarded after a single use. If a hollow needle is designed for single use, the number of needles needed in a treatment would be the same as the number of holes desired. In some embodiments, if a hollow staple is designed for single use, the number of staples needed in a treatment would be about half of the number of holes desired. In some embodiments, technologies, devices and/or methods described herein can provide increased effectiveness in cosmetic resurfacing when compared to currently available apparatuses and techniques, while maintaining convenience, affordability, and accessibility to patients desiring skin rejuvenation.

Articles Having Integrated Needles

In some embodiments, technologies, devices and/or methods described herein comprise an article including a plurality of needles (e.g., hollow needles) for producing a cosmetic effect in a skin tissue. In some embodiments, an article may include a first layer joined to a second layer, within which a plurality of needles (e.g., hollow needles) may be affixed. Needles (e.g., hollow needles) may be disposed in an article in a retracted and/or a protracted position. In some embodiments, needles may be disposed in an article in a retracted and position and configured to extend to a protracted position. First and second layers of an article may be joined using, e.g., an adhesive polymer or stitches. An article may include an adhesive material on the exterior surface of one of the first or second layers that functions to adhere the article to the skin. An adhesive material can be covered with a backing material that can be removed prior to use of the article to expose the adhesive material. An article can then be placed on a region of skin tissue and secured by an adhesive material. An article can be prepared in a sterile wrapping or container for storage prior to use.

An article may also be stretchable. For example, one or both of first and second layers may comprise a material, such as rubber, lycra, spandex, nylon, or polyester. In some embodiments, an article may be in form of a tape or a patch. An article may be designed or configured to have any shape and/or size that fits or conforms to a shape and/or size of a desired skin area for treatment, e.g., the skin area of face (e.g., eyelid, lips, cheeks, chin, forehead, lips, or nose), neck, chest (e.g., as in a breast lift), arms, hands, legs, abdomen, and/or back. For example, an article may be ring shaped for treatment of the skin area around an eye.

An article described herein may be easily adapted to fit any contours of skin, such that there are no substantial gaps between needles (e.g., hollow needles) in an article and the skin surface caused by mismatch of shape and/or size of the article to the contours of the skin. For example, an article may be malleable to folding, stretching, and/or bending to conform to, e.g., a shape of the nose or the jaw. For example, an article may be cut to shape with, e.g., scissors, to fit a shape of a treatment area. A user may receive a large sized article and be able to easily cut or otherwise modify the article to apply it to a target treatment area. In another example, a user may be supplied with multiple small sized articles having a specific shape (e.g., a hexagon or octagon shape) that may be attached or connected together to cover a large treatment area. FIG. 1G illustrates an exemplary embodiment of small sized articles having a hexagon shape (article 10). Hexagon shaped articles may be attached together or placed closely adjacent to each other to cover a large area, e.g., an entire face. Such an article can provide benefits including ease of use, disposability of components or an entire article, rapid treatment of skin, lower skill level required for use, and potential for outpatient treatment with rapid healing times.

An article as described herein may be rigid. In some embodiments, a rigid article may fit any contour of skin. An article as described herein may be generated based on a 3D model of a treatment area, e.g., a model based on medical imaging. An article may be 3D printed or generated using a 3D printed mold. An article as described herein may comprise rigid and/or flexible components. In some embodiments, an article is rigid at a macroscopic scale and may comprise flexible microscopic components. In some embodiments, an article is flexible at a macroscopic scale and may comprise rigid microscopic components. In some embodiments, an article is customizable and/or adaptable. In some embodiments, an article may change its rigidity from flexible to rigid or from rigid to flexible.

First and Second Layers

In some embodiments, an article may include a first layer joined to a second layer. Needles (e.g., hollow needles) may be affixed between first and second layers, in which a length of needles may correspond approximately to the thickness of an article. One or more tips of needles may be in contact with or in proximity to an inner surface of a first layer of an article, while one or more ends of needles may be in contact with or in proximity to an inner surface of a second layer.

In some embodiments, a first layer of an article is configured to be in contact with skin tissue of a subject. In some embodiments, a first layer may include a plurality of openings that are aligned with tips of a plurality of needles (e.g., hollow needles) affixed between first and second layers. Prior to applying an article to skin tissue of a subject and inserting needles into skin tissue, needles are disposed in an article in a retracted position, in which tips of needles are not extended through openings in a first layer. In other words, needles are buried or covered entirely within first and second layers of an article. Once an article is in contact with the skin tissue, needles may be pushed to a protracted position, which can result in tips of needles extending through openings in the first layer and inserting into skin tissue.

In some embodiments, proximal ends of a plurality of needles (e.g., hollow needles) in an article may be in proximity to an inner surface of a second layer of an article or attached to an inner surface of a second layer of an article. A second layer of an article may include a plurality of protrusions, in which each protrusion indicates a location of a single one of a plurality of needles, and the protrusions are configured to be pushed down to extend one or more needles to a protracted position.

In some embodiments, an article may be configured with an adhesive layer that allows an article to adhere to skin tissue once it is in contact with skin tissue. For example, an exterior surface of a first layer may further include an adhesive material on one or more portions of a first layer (e.g., the surface that is in contact with skin tissue). In some embodiments, an article may further include a releasable backing material that covers an adhesive material on one or more portions of an outer surface of a first layer that can be removed (e.g., peeled off) to expose adhesive material prior to applying an article to skin tissue. In some embodiments, an adhesive material may be a pressure sensitive adhesive (PSA), a non-reactive adhesive, a contact adhesive, a hot melt adhesive, a reactive adhesive, a one-part adhesive, a natural adhesive, or a synthetic adhesive. For example, an adhesive material may be an elastomer, a thermoplastic, an emulsion, or a thermoset, such as acrylic, synthetic or natural rubber, ethylene-vinyl acetate (EVA), nitrile, silicone (e.g., a siliconized material), styrene block copolymer, or vinyl ether.

In some embodiments, an adhesive may comprise one or more additional substances, e.g., a bioactive agent, an anesthetic/analgesic, a coagulant, an anti-infective agent, a drug, and/or biological material. In some embodiments, an adhesive layer remains on skin after removal of an article. In some embodiments, an adhesive comprises a polymeric film. In some embodiments, an adhesive film contracts, shrinks, and/or deforms otherwise, e.g., causing and/or promoting wound closure in and/or in vicinity of a treatment area. In some embodiments, an adhesive film expands, extends, and/or deforms otherwise, e.g., causing and/or promoting wound closure in a treatment area. In some embodiments, a film is opaque, translucent, or transparent. In some embodiments, a film has certain physical and/or chemical properties. In some embodiments, a film may have certain thermal properties (e.g., cooling, heating, insulating). In some embodiments, a film may seal a skin area or may allow diffusion (e.g., "breathing"). In some embodiments, a film may be biodegradable and/or bioabsorbable. In some embodiments, a film can be removed and/or re-applied.

In some embodiments, an article may include a texture configured to reduce movement along skin tissue on a portion of a first layer. For example, the texture may include hooks, bumps, ridges, and/or grooves. In other embodiments, an article may be attached to skin through application of a vacuum (e.g., suction) and/or by using a vacuum seal. In some embodiments, an article is shaped to maintain close proximity to skin tissue by way of suction. In some embodiments, an article maintains a close proximity to skin tissue skin through application of a vacuum (e.g., suction) and/or by using a vacuum seal. A pressure generating source (e.g., a vacuum pump) may be disposed inside an article or used as a stand-alone device that is attached to an article, e.g., by tubing. In some embodiments, an evacuated chamber in fluid communication with a system can be used communicate negative pressure.

Tensioner

In some embodiments, technologies, devices and/or methods described herein comprise an article including one or more tensioners that are incorporated around needles (e.g., hollow needles). A tensioner may apply a force to create or maintain tension and/or compression. In some embodiments, a tensioner may apply a force to create or maintain tension. A tensioner may be a mechanical component that is configured to engage with a needle (e.g., a hollow needle) to translate a needle from a retracted position to a protracted position and/or from a protracted position to a retracted position. In some embodiments, a tensioner may be made from an elastic, flexible, and/or stretchable material. For example, a tensioner may comprise a spring, an elastic band (e.g., a rubber band), and/or a snap dome.

In an example, a tensioner may be a spring that is configured to wrap around a needle in an article. A needle (e.g., a hollow needle) in a retracted position in an article may be engaged with a spring in an uncompressed configuration (e.g., an uncompressed spring). As a needle is pushed down to extend through an opening in a first layer to insert into skin tissue, the needle is translated from a retracted position to a protracted position, and a spring engaging with a needle is compressed to a compressed configuration (e.g., a compressed spring). Since the natural tendency of the spring is to return to an uncompressed configuration, a compressed spring may translate a needle from a protracted position back to a retracted position as it goes back to an uncompressed configuration. Subsequently, ab article may be removed (e.g., peeled off) from skin.

In another example, a needle (e.g., a hollow needle) in a retracted position in the article may be engaged with a spring in a compressed configuration (e.g., a compressed spring). In this example, as a needle is pushed down to extend through a first layer to insert into skin tissue, the needle is translated from a retracted position to a protracted position, and a compressed spring engaging with the needle is released to an uncompressed configuration (e.g., an uncompressed spring). In particular, a spring may facilitate insertion of a needle into skin as it converts from a compressed configuration to an uncompressed configuration. Subsequently, needles may be withdrawn from skin by removing (e.g., peeling off) an entire article from skin.

In yet another example, a needle (e.g., a hollow needle) in a retracted position in an article may be engaged with a spring in a stretched configuration (e.g., a stretched spring). In this example, as a needle is pushed down to extend through a first layer to insert into skin tissue, the needle is translated from a retracted position to a protracted position, and a stretched spring engaging with the needle is released from a stretched configuration to an unstretched configuration, thereby adding force to the insertion of a needle into skin tissue. Subsequently, needles may be withdrawn from skin by removing (e.g., peeling off) an entire article from skin.

In another example, a tensioner may be a snap dome that is configured to engage with a needle in an article. A needle (e.g., a hollow needle) in a retracted position in the article may be engaged with a snap dome in an uncompressed configuration (e.g., an uncompressed snap dome). As a snap dome is pushed down either by hand (e.g., by hand or finger pressure) or using an applicator (described further herein), the snap dome is changed to a compressed configuration and a needle engaging with the snap dome is extended through the opening in a first layer to insert into skin tissue (e.g., translated from a retracted position to a protracted position). Since the natural tendency of a snap dome is to return to an uncompressed configuration, a compressed snap dome may translate the needle from a protracted position back to a retracted position as it goes back to an uncompressed configuration. Subsequently, an article may be removed (e.g., peeled off) from skin.

A tensioner engaging with a needle (e.g., a hollow needle) in an article may be have various degrees of tightness and/or elasticity. Different tensioners may be installed within an article depending on, e.g., the desired depth or velocity of penetration of needles. A needle may be configured to extend (i) into the dermal layer, (ii) through an entire dermal layer to a junction of a dermal layer and a subcutaneous fat layer, and/or (iii) into a subcutaneous fat layer. For example, a spring having a high degree of elasticity may be compressed or stretched more easily as compared to a spring having a low degree of elasticity. Springs having different lengths may engage with a needle for penetration into different depths of skin tissue. In some embodiments, a spring having a long length may engage with a needle for penetration into the subcutaneous fat layer, while a spring having a short length may engage with a needle for penetration into the dermal layer.

Applicator

In some embodiments, technologies, devices and/or methods described herein comprise an applicator that may be used in combination with the articles described herein, e.g., to apply pressure on needles or staples (e.g., hollow needles or hollow staples) to extend them from a retracted position to a protracted position. An applicator may be configured for handheld operation. In some embodiments, pressure from an applicator may be applied by hand (e.g., with hand or finger pressure) or via a mechanical component, which can be integrated into an applicator. In some embodiments, an applicator can be a finger, a stylus, a roller, a pen, a ball, a hammer, a paddle, a pad, a vibrating element (e.g., an ultrasonic element), or any solid or partially-solid object.

In some embodiments, a tip of an applicator may have a concave shape that accommodates a protrusion in a second layer of an article. A tip of an applicator may also include a visibility window that allows a user to visualize whether a protrusion is pressed down or remains in an uncompressed state, which indicates whether a needle (e.g., a hollow needle) underneath a protrusion is in a protracted position (e.g., inserted into skin tissue) or in a retracted position (e.g., not inserted into skin tissue), respectively. A tip of an applicator may be coated with a lubricant to facilitate ease of use.

In some embodiments, needles in an article may be inserted into skin tissue by applying an article to skin tissue, e.g., adhering an outer surface of a first layer of an article to skin tissue, and pushing down onto an article, e.g., pushing down onto protrusions (if present) in a second layer, to extend needles from a retracted position to a protracted position, where tips of needles are extended through openings in a first layer and inserted into skin tissue. To withdraw needles from skin tissue, an entire article may be removed (e.g., peeled off) from skin tissue, or needles may be translated from a protracted position back to a retracted position by, e.g., a tensioner (e.g., a spring).

Alternatively, in some embodiments, a user may also apply pressure on needles (e.g., hollow needles) of articles by hand (e.g., with hand or finger pressure) to insert needles into skin tissue. Each needle may be pressed by hand individually or multiple needles may be pressed by hand simultaneously to insert into skin tissue.

Figure 1B:
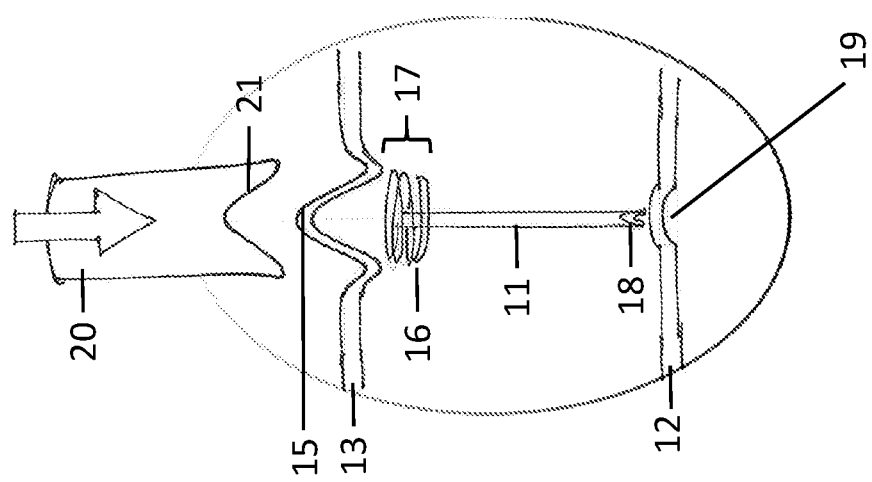
Figure 1D:
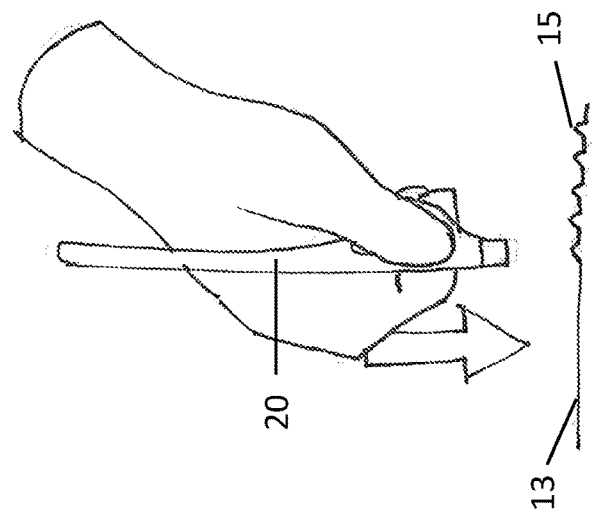
FIG. 1D is a schematic illustration showing applicator 20 configured for handheld operation (e.g., with the article of FIGS. 1A-1C).
Figure 1E:
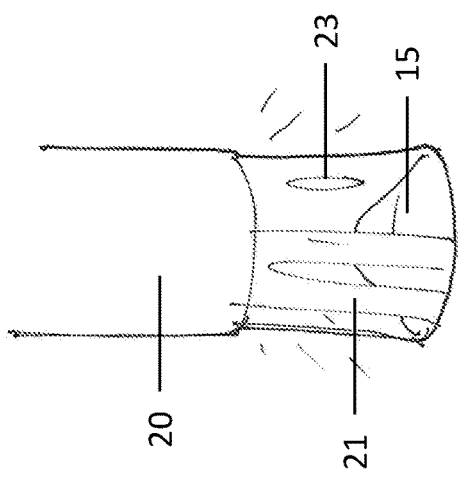
FIG. 1E is a schematic illustration showing an enlarged view of tip 21 of applicator 20 shown in FIG. 1D.
Figure 1F:
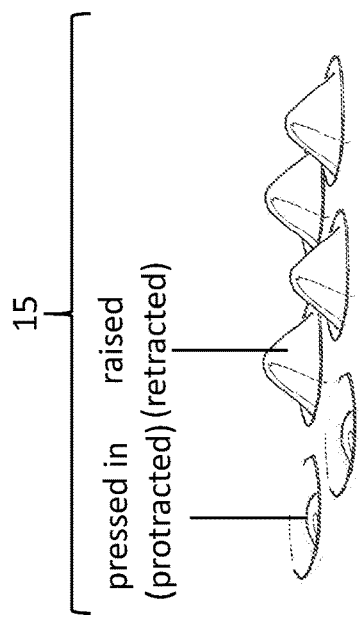
FIG. 1F is a schematic illustration showing an enlarged view of protrusions 15 in article 10 shown in FIG. 1A.
Figure 1G:
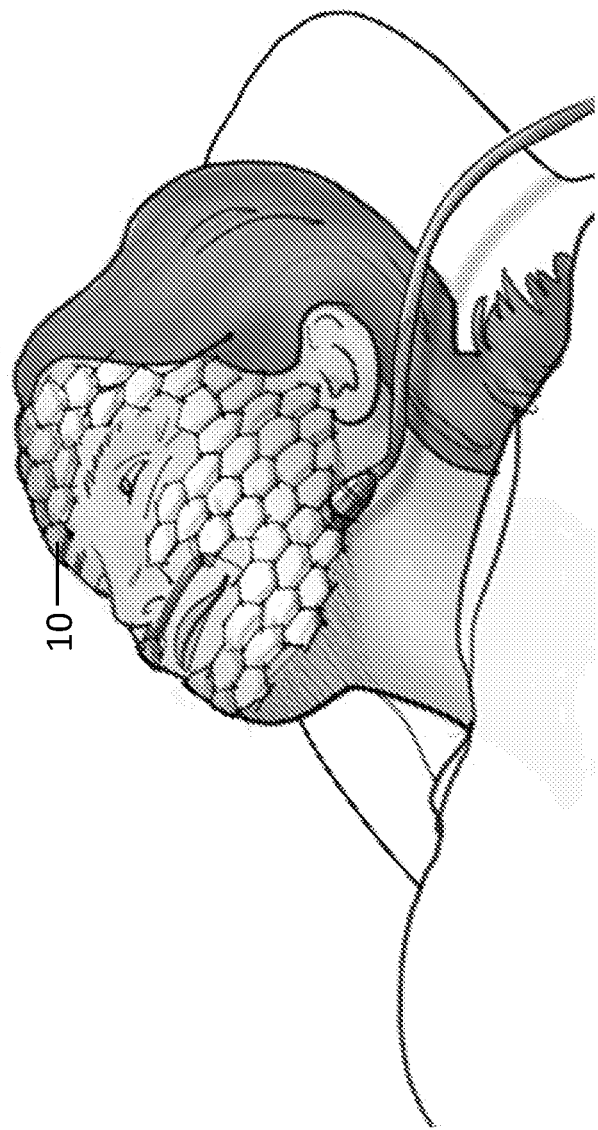
FIG. 1G is a schematic illustration showing multiple hexagon shaped articles 10 that are placed together to cover an entire face of a subject.

Examples of an article and an applicator are shown in FIGS. 1A-1G. FIG. 1A shows article 10 having needles 11 (e.g., hollow needles) affixed between first layer 12 and second layer 13. First layer 12 includes an adhesive material covered by releasable backing 14, which can be peeled off, prior to applying article 10 to the skin. Second layer 13 includes multiple protrusions 15 that indicate the locations of needles 11 within the layers of article 10. As shown in FIG. 1B, tensioner 16 (e.g., a spring) may be used to translate needle 11 from a retracted position to a protracted position and/or from a protracted position to a retracted position. FIG. 1B shows an enlarged view of needle 11 affixed between first layer 12 and second layer 13 and engaged with tensioner 16 (e.g., a spring). As shown in FIG. 1B, tensioner 16 (e.g., a spring) in compressed configuration 17 is disposed within article 10 to engage with needle 11 in the retracted position (e.g., tip 18 of needle 11 does not extend through opening 19 in first layer 12). Applicator 20 having concave tip 21 is used to apply pressure on protrusion 15 to translate needle 11 from the retracted position (e.g., tip 18 of needle 11 does not extend through opening 19 in first layer 12) to a protracted position (e.g., tip 18 of needle 11 extends through opening 19 in first layer 12), as shown in FIG. 1C. FIG. 1C also shows that as hollow need 11 is translated to the protracted position, tensioner 16 (e.g., a spring) is changed to uncompressed configuration 22, thereby facilitating insertion of needle 11 into skin tissue. FIG. 1D shows applicator 20 configured for handheld operation, which can be used to press down onto protrusion 15 in second layer 13 of article 10. Visualization window 23 that allows a user to view the status of protrusion 15 can be installed at tip 21 of applicator 20 (see FIG. 1E). FIG. 1F shows an enlarged view of protrusions 15 in second layer 13 of the article 10, some of which are pressed into the second layer, indicating that the needles underneath the protrusions are inserted into the skin tissue (e.g., in the protracted position), while others are raised, indicating that the needles are not yet inserted into the skin tissue (e.g., in the retracted position). FIG. 1G shows multiple hexagon shaped articles 10 that are placed together to cover an entire face of a subject.

Systems Configured to Accept Needles

In some embodiments, technologies, devices and/or methods described herein comprise systems including one or more components that are configured to function together to debulk skin tissue (e.g., removing tissue portions from the skin) and/or trigger biological responses that can contribute to tissue resurfacing and remodeling. One of the components of a system may be a template that is configured to accept or accommodate needles (e.g., hollow needles). A template may serve as a guide or a mold that facilitates positioning of needles over skin to be treated. A template may comprise one or more holes or openings that provide a pre-set pattern (described further herein) for needles to follow. A template may be used alone or in combination with a position detection mechanism that provides an indication to a user of the system regarding the positioning of needles (e.g., hollow needles). Needles may be configured to fit into holes or openings in a template, thereby following a pattern set by a template. Needles used in a system including one or more components may be attached to a support, e.g., a strip, which may be configured to engage with a template in a system.

Needle Strip/Trough Configuration

In some embodiments, technologies, devices and/or methods described herein comprise a template having at least one trough and a strip having a plurality of needles (e.g., hollow needles), wherein a strip is configured to fit within a trough of a template. A trough of a template may include a plurality of holes or openings for needles to extend through when they are inserted into skin tissue. A template may be configured with different sizes and/or shapes that are adapted for treatment of different skin areas. For example, a template may be modified, e.g., cut to shape with, e.g., scissors, to fit the shape of a treatment area. A user may receive a large sized template and be able to easily cut a template to apply it to a target treatment area. In another example, a user may be supplied with multiple small sized templates having a specific shape that may be attached together to cover a large treatment area. Accordingly, a strip, or other shape, may be cut to fit within a trough of a template. A template may have multiple troughs, which may be arranged in different configurations. For example, a template may include multiple rows of troughs configured for a needles to generate a pattern of holes in multiple rows.

A template may be constructed from, e.g., a rubber-based material (e.g., an elastomer), or any other type of material that is malleable to conform to a desired shape or configuration, yet maintains rigidity of the individual troughs in a template. A template may also be constructed from, e.g., hard plastic, molded plastic, and/or metal.

In some embodiments, a template in a system may be placed on a surface of skin tissue needing treatment. A skin-contacting surface of the template may be coated with an adhesive material that functions to adhere a template onto skin surface, e.g., to prevent or reduce slippage during use. Furthermore, a template may have a releasable backing material covering an adhesive material on a skin-contacting surface of a template that can be removed (e.g., peeled off) prior to use. An adhesive material may be a pressure sensitive adhesive (PSA), a non-reactive adhesive, a contact adhesive, a hot melt adhesive, a reactive adhesive, a one-part adhesive, a natural adhesive, and/or a synthetic adhesive. For example, an adhesive material may be an elastomer, a thermoplastic, an emulsion, and/or a thermoset. In some embodiments, an adhesive material may be acrylic, synthetic and/or natural rubber, ethylene-vinyl acetate (EVA), nitrile, silicone (e.g., a siliconized material), styrene block copolymer, and/or vinyl ether.

In some embodiments, a template may also be configured to adhere to skin by suction (e.g., by the application of a vacuum) or through use of a texture that is configured to reduce movement of a template along skin tissue. In some embodiments, if suction is used, a pressure generating source (e.g., a vacuum pump) may be disposed inside a template or used as a stand-alone device. In some embodiments, an evacuated chamber in fluid communication with a system can be used to communicate negative pressure. Alternatively, a texture that is configured to reduce movement may include hooks, bumps, ridges, and/or grooves, which may be disposed on a skin-contacting surface of a template, which prevents or reduces slippage of a template along skin surface.

In some embodiments, a plurality of needles (e.g., hollow needles) may be affixed onto a strip that is configured to engage with a template. A strip may have any shape or size that fits within a trough of a template and allows needles affixed onto a strip to extend through openings in a template when needles are inserted into skin tissue. The arrangement of needles affixed onto a strip depends on the shapes and sizes of a strip and a template, which can be configured to integrate for coordinated use. For example, a rectangular shaped strip having needles arranged in a row may be used with a template having multiple rows of troughs, such that a rectangular shaped strip can fit within a trough of each row. A strip may have multiple corrugations (see, e.g., FIGS. 2A, 2C, and 2D) with peaks and/or grooves. In this configuration, a strip comprising needles (e.g., hollow needles) can be placed within a groove between two peaks and tips of the needles are placed so as to be in line with holes in a template. Thus, corrugations in a strip allow for translation of one or multiple needles from a first position (e.g., tips of needles do not extend through openings in a trough) to a second position (e.g., tips of needles extend through openings in a trough).

In some embodiments, a system may also be adapted for use with, or to further include, an applicator. An applicator may be used to apply pressure on a strip, thereby inserting needles (e.g., hollow needles) into skin tissue. An applicator may be used to insert one needle into the skin tissue at a time or multiple needles into skin tissue at the same time. Corrugations in a strip, if present, may control movement of one or multiple needles (e.g., promoting translation in a substantially vertical direction and preventing or reducing movement in horizontal direction) when they are pressed down by the applicator. In some embodiments, to ensure smooth insertion of needles into skin tissue and to facilitate ease of use, a tip of an applicator may be coated with a lubricant.

In some embodiments, an applicator may be configured for handheld operation. Pressure from an applicator may be applied by hand (e.g., with hand or finger pressure) or with a mechanical component, which can be integrated into an applicator. To withdraw needles (e.g., hollow needles) from skin tissue, a strip with affixed needles may be disengaged from a template and removed (e.g., peeled off) from skin tissue. In some embodiments, a template and a strip with affixed needles may be removed together.

In some embodiments, each component in the system, e.g., a template, a strip including needles (e.g., hollow needles), and/or an applicator may be discarded and/or replaced, e.g., with new components after each use. Alternatively, in other embodiments, each component, or only a subset of the components, in a system, e.g., a template, a strip including needles, and/or an applicator may be sterilized for repeated use. For example, a strip with needles may be discarded, while a template and an applicator may be sterilized and reused.

Figure 2A:
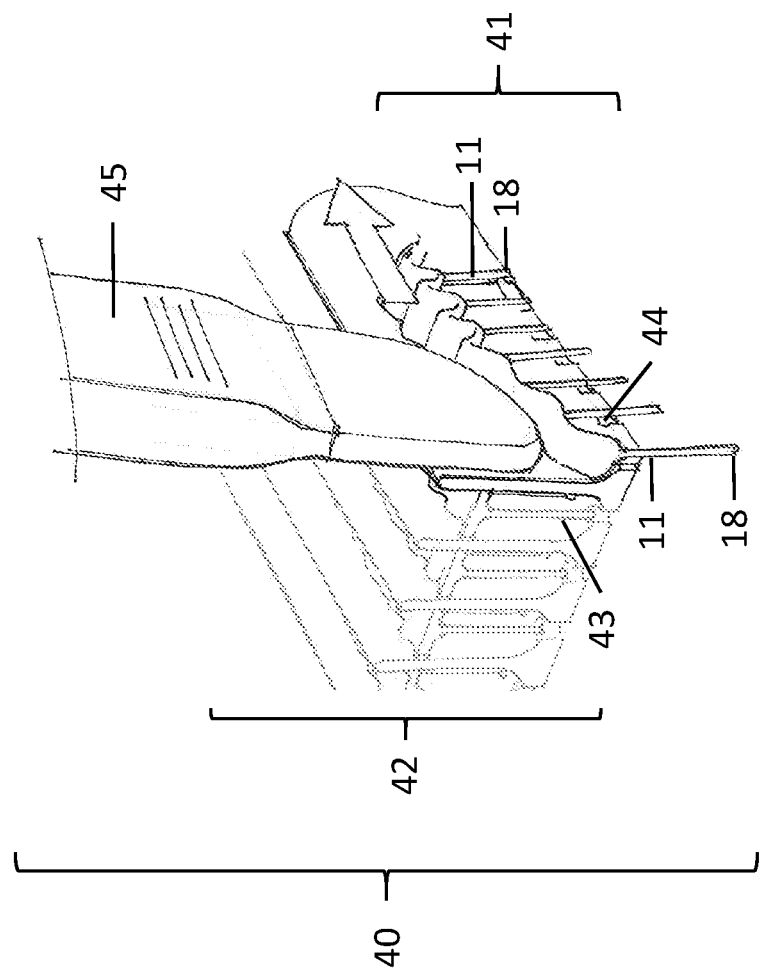
FIG. 2A is a schematic illustration showing system 40 including strip 41, template 42, and applicator 45.

An example of a system including a template having at least one trough, a strip having a plurality of needles (e.g., hollow needles), and an applicator is shown in FIGS. 2A-2E. FIG. 2A shows system 40, in which strip 41 includes needles 11 (e.g., hollow needles). Strip 41 is assembled to fit within trough 43 of template 42. Each needle 11 (e.g., hollow needle) is configured to align with opening 44 in trough 43 when strip 41 is placed with trough 43 of template 42. FIG. 2A also shows applicator 45 applying pressure onto at least one needle 11 (e.g., hollow needle) in strip 41 to translate needle 11 from a first position (e.g., tip 18 of needle 11 does not extend through opening 44) to a second position (e.g., tip 18 of needle 11 extends through opening 44). FIG. 2B further shows template 42 in a folded form before it is applied onto the skin surface. Skin-contacting surface 46 of template 42 is covered with releasable backing material 47, which may be removed (e.g., peeled off) to apply template 42 onto a skin surface. Skin-contacting surface 46 may have an adhesive material that facilitates adhesion of template 42 to a skin surface. FIG. 2C shows strip 41 being assembled into trough 43 such that needles 11 (e.g., hollow needles) are aligned with openings 44 in trough 43. FIG. 2D shows individual strips 41 engaged with individual troughs 43. Finally, FIG. 2E shows applicator 45 configured for hand-held operation with system 40.

Shuttle Guide Configuration

In some embodiments, technologies, devices and/or methods described herein comprise a template that may have any one of several different alternative configurations. For example, a template may be configured to include (a) a first layer including a plurality of openings, (b) a second layer including at least one track, and (c) a receptacle that is disposed inside a track in a second layer. Needles (e.g., hollow needles) may be affixed between first and second layers, in which tips of needles are engaged with a plurality of openings in a first layer. In some embodiments, a plurality of openings in the first layer may provide a pre-set pattern (described further herein). Track(s) in a second layer may be positioned such that track(s) overlay openings in a first layer. For example, a plurality of openings in a first layer and track(s) in a second layer may both be arranged in multiple rows (e.g., one to ten rows) to function together to insert needles into skin tissue. Moreover, a receptacle may be disposed inside a track to engage with both track and an applicator used to insert needles into skin tissue. In some embodiments, a receptacle may be positioned above one needle (e.g., a hollow needle) at a time. An applicator may be inserted into a receptacle to (1) push a needle into skin tissue and, subsequently, (2) to advance a receptacle to a position above an adjacent hollow needle.

In some embodiments, a template in a system may be configured to contact a surface of skin tissue by a first layer. A template in a system may be placed onto a surface of skin tissue needing treatment. A first layer of a template may be coated with an adhesive material that functions to adhere a template onto skin surface. Furthermore, an adhesive material on a first layer of a template may be covered with a releasable backing material when the template is not in use. Releasable backing material may be removed (e.g., peeled off) to expose an adhesive material prior to placing a template onto a surface of skin. In some embodiments, an adhesive material may be a pressure sensitive adhesive (PSA), a non-reactive adhesive, a contact adhesive, a hot melt adhesive, a reactive adhesive, a one-part adhesive, a natural adhesive, and/or a synthetic adhesive. For example, an adhesive material may be an elastomer, a thermoplastic, an emulsion, and/or a thermoset. In some embodiments, an adhesive material may be acrylic, synthetic or natural rubber, ethylene-vinyl acetate (EVA), nitrile, silicone (e.g., a siliconized material), styrene block copolymer, and/or vinyl ether.

In some embodiments, a template may also be configured to adhere to skin by suction (e.g., by application of a vacuum) or through use of a texture that is configured to reduce movement of a template along a skin tissue. If suction is used, a pressure generating source (e.g., a vacuum pump) may be disposed inside a template or used as a stand-alone device. In some embodiments, an evacuated chamber in fluid communication with a system can be used to communicate negative pressure. Alternatively, a texture that is configured to reduce movement may include hooks, bumps, ridges, and/or grooves, which may be disposed on a skin-contacting surface of a template, which prevents or reduces slippage of a template along a skin surface.

In some embodiments, once a template is placed onto a surface of skin needing treatment, an applicator may be used to engage with the receptacle disposed inside a track in a second layer of a template. An applicator may be configured for hand-held positioning and/or operation. An applicator may include an end effector that is used to push a needle (e.g., a hollow needle) into skin tissue. In some embodiments, an end effector may be long and rigid so as to fit through a receptacle. An applicator may be inserted into a receptacle in order to contact an end of a hollow needle. A needle can be pushed down by an applicator in order to extend a needle (e.g., a hollow needle) from a first position, in which a tip of a needle is aligned with an opening in a first layer, to a second position, in which a tip of a needle extends through an opening to insert into skin tissue. Once a needle is inserted into skin tissue, an applicator may be used to translate a receptacle along a track to position a receptacle above an adjacent hollow needle. Needles (e.g., hollow needles) in a system may be withdrawn from skin tissue by, e.g., removing an entire template from skin surface.

In some embodiments, each component in a system, e.g., template (a first layer, a second layer, and a receptacle), needles (e.g., hollow needles) affixed between first and second layers, and/or an applicator may be discarded and replaced with a new component after each use. Alternatively, each component, or only a subset of the components, in a system, e.g., a template (a first layer, a second layer, and a receptacle), needles affixed between first and second layers, and/or an applicator may be sterilized for repeated use. For example, needles (e.g., hollow needles) may be discarded, while template and applicator may be sterilized and reused.

Figure 3A:
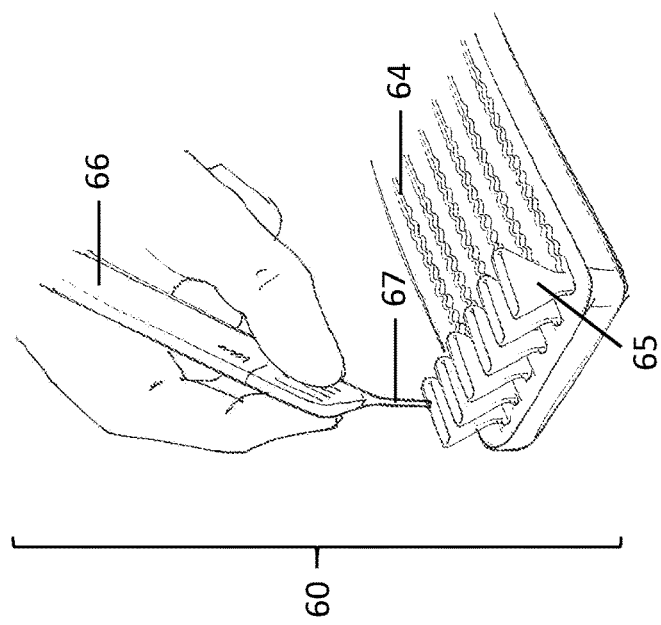
FIGS. 3A, 3B, and 3C are schematic illustrations showing system 60 including first layer 61, second layer 62, receptacle 65, applicator 66, and needles 11 (e.g., hollow needles) in different stages of operation.
Figure 3B:
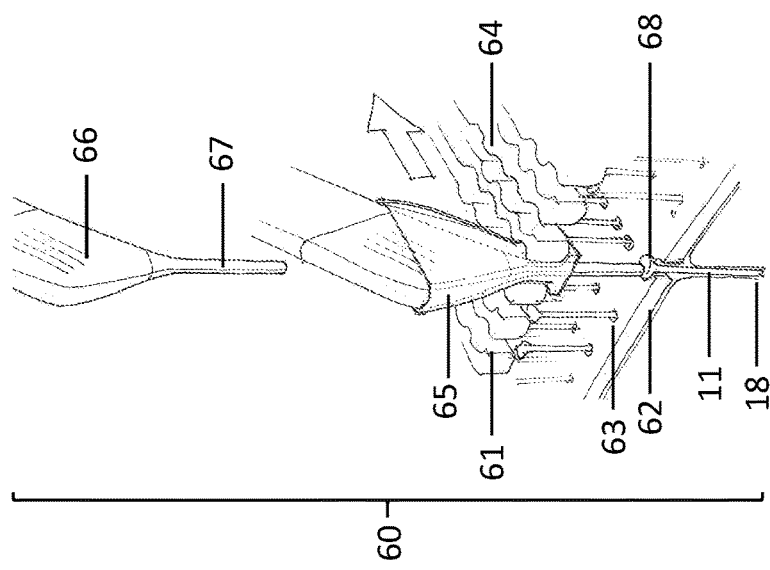
Figure 3C:
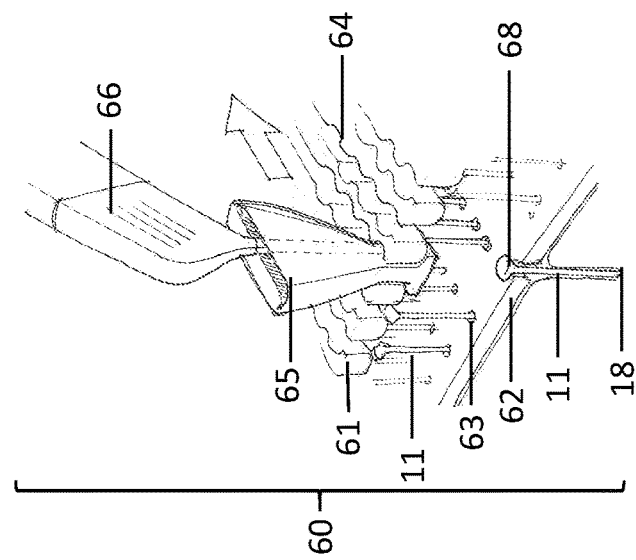

An example of a system including a template having a first layer, a second layer, and a receptacle disposed in the first layer, needles (e.g., hollow needles) affixed within the template, and an applicator is shown in FIGS. 3A-3C. FIGS. 3A-3C show system 60, in which needles 11 (e.g., hollow needles) are affixed between first layer 61 and second layer 62. First layer 61 includes plurality of openings 63 (FIG. 3B). Each opening 63 can be engaged with tip 18 of needle 11 (e.g., a hollow needle). First layer 61 includes tracks 64. Receptacle 65 is disposed in track 64 in first layer 61. Applicator 66 with end effector 67 may be inserted into receptacle 65 to push on end 68 of needle 11 (e.g., a hollow needle) to translate needle 11 from a first position, in which tip 18 is aligned with opening 63, to a second position, in which tip 18 extends through opening 63 to insert into skin tissue (see FIGS. 3B and 3C). Subsequently, end effector 67 of applicator 66 may be used to advance receptacle 65 along track 64 to position receptacle 65 above an adjacent needle that has not yet been inserted into skin tissue (FIG. 3C).

Pen-Click Configuration

In some embodiments, technologies, devices and/or methods described herein comprise a a template that may include a plurality of sleeves. Each sleeve may include two openings at opposite ends of the sleeve. A first opening of the sleeve can be configured to be in contact with a surface of skin tissue. A needle (e.g., a hollow needle) may be slidably mounted inside a sleeve, in which a tip of a needle is aligned with a first opening of a sleeve when a needle is not inserted into skin tissue. In some embodiments, a tensioner (e.g., a spring) may be further mounted inside a sleeve to engage with a hollow needle. A tensioner may be in an uncompressed configuration (e.g., an uncompressed spring) when a needle is not inserted in skin tissue and in a compressed configuration (e.g., a compressed spring) when a needle is pushed down toward skin (e.g., using an applicator), causing a needle (e.g., a hollow needle) to penetrate skin tissue. Release of a needle can result in a needle popping out of skin as a tensioner moves back to an uncompressed configuration.

In some embodiments, a spring may also be in a compressed configuration (e.g., a compressed spring) when a needle (e.g., a hollow needle) is not inserted in skin tissue and in an uncompressed configuration (e.g., an uncompressed spring) when a needle is pushed down toward skin (e.g., using an applicator or by hand (e.g., with hand or finger pressure)), causing a needle (e.g., a hollow needle) to penetrate skin tissue.

In some embodiments, a system may include an applicator used to push a needle inside a sleeve from a retracted position, in which a tip of a needle is aligned with a first opening of a sleeve, to a protracted position, in which a tip of a needle extends through a first opening of a sleeve and inserts into skin tissue. An applicator may be configured to fit inside a sleeve such that an applicator may engage with an end of a needle when a needle is inserted into skin tissue. Alternatively, a user may push a needle inside a sleeve from a retracted position to a protracted position by hand (e.g., with hand or finger pressure).

In some embodiments, inner and/or outer diameter of a sleeve in a template may vary across a length of a sleeve, such that a diameter of one region of a sleeve may be different from an outer and/or inner diameter of another region of the same sleeve. The change in a diameter across a sleeve may or may not be continuous. A sleeve may or may not be entirely cylindrical. In some embodiments, a sleeve may be substantially cylindrical across its entire length.

For example, as shown in FIGS. 4A and 4B, an upper portion of a sleeve, e.g., the portion proximal to an end of a needle (e.g., a hollow needle) and a second opening of the sleeve, may have a larger diameter than that of a lower portion of a sleeve, e.g., the portion proximal to a tip of a needle and a first opening of a sleeve. In some embodiments, the large diameter of an upper portion of a sleeve may allow a sleeve to accommodate a tensioner (e.g., a spring) mounted inside a sleeve. In some embodiments, the large diameter of an upper portion of a sleeve may also allow a sleeve to accommodate an applicator, which may be inserted into an upper portion of a sleeve. A sleeve may have an inner diameter from about 1 mm to about 3 mm (e.g., 1, 1.2, 1.4, 1.6, 1.8, 2, 2.2, 2.4, 2.6, 2.8, or 3 mm) and a length from about 3 mm to about 10 mm (e.g., 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 mm).

In some embodiments, a tensioner mounted inside a sleeve to engage with a needle (e.g., a hollow needle) may be a mechanical component that is configured to translate a needle from a retracted position to a protracted position and/or from a protracted position to a retracted position. A tensioner may be made from an elastic, flexible, and/or stretchable material. A tensioner may be a spring, an elastic band (e.g., a rubber band), and/or a snap dome. For example, a tensioner may be a spring that is configured to wrap around a needle in a sleeve. In one example, a needle in a retracted position in a sleeve may be engaged with a spring in an uncompressed configuration (e.g., an uncompressed spring). In a retracted position, a tip of the needle is aligned with a first opening of a sleeve and a needle is not inserted into skin tissue. As a needle is pushed down by an applicator to insert into skin tissue, a needle is translated from a retracted position to a protracted position, in which a tip of a needle extends through a first opening of a sleeve to insert into skin tissue. Concurrently, a spring engaging with a needle is changed from an uncompressed configuration to a compressed configuration (e.g., a compressed spring). To withdraw a needle from skin tissue, an applicator may be removed and a compressed spring may translate a needle from a protracted position back to a retracted position as a spring naturally goes back to its uncompressed configuration.

In some embodiments, an applicator may be configured to fit inside a sleeve, such that it may engage with a needle and a tensioner mounted inside a sleeve. A diameter of an applicator may vary across its length, such that a diameter of one region of an applicator may be different from a diameter of another region of the applicator. Change in a diameter across the applicator may or may not be continuous. In some embodiments, an applicator may have a tapered end, e.g., as shown in FIGS. 4A and 4B.

An example of a system including a template having a plurality of sleeves, needles (e.g., hollow needles) each mounted within a sleeve, and an applicator is shown in FIGS. 4A and 4B. FIGS. 4A and 4B show system 70, in which needle 11 (e.g., a hollow needle) is mounted within sleeve 71 having first opening 72 and second opening 73. Tensioner 74 (e.g., a spring) is also mounted within sleeve 71. FIG. 4B shows schematic illustrations of sequential events depicting needle 11 (e.g., a hollow needle) being inserted into the skin tissue. First, needle 11 (e.g., a hollow needle) is in a retracted position, in which tip 18 of needle 11 (e.g., a hollow needle) is aligned with first opening 72 of sleeve 71 and tensioner 74 (e.g., a spring) is in uncompressed configuration 75. As applicator 76 having tapered end 77 is inserted into sleeve 71 to engage with needle 11 (e.g., a hollow needle) and tensioner 74 (e.g., a spring), needle 11 (e.g., a hollow needle) is translated from the retracted position to a protracted position, in which tip 18 of needle 11 extends through first opening 72 and tensioner 74 (e.g., a spring) is in compressed configuration 78. As applicator 76 is removed from sleeve 71 and disengaged from needle 11 and tensioner 74 (e.g., a spring), tensioner 74 (e.g., a spring) naturally releases back to uncompressed configuration 75 and, at the same time, translates needle 11 from the protracted position back to the retracted position.

Systems Including Needle Guides

In some embodiments, technologies, devices and/or methods described herein comprise guide rails that function to provide tracks for a needle (e.g., a hollow needle) to follow and to help define a pre-determined treatment pattern. A system can include a guide rail and a main body including a needle mounted inside a main body. In some embodiments, a tensioner (e.g., a spring) may also be mounted inside a main body to engage with a hollow needle. In some embodiments, structures of guide rail and main body may be designed such that a main body may be configured to follow a backbone or a groove in a guide rail.

Main Body

In some embodiments, technologies, devices and/or methods described herein comprise a main body that includes a needle (e.g., a hollow needle) mounted inside the main body. A main body may be configured for handheld operation and a needle inside a main body may be detachably attached to a main body. In some embodiments, a main body may feature a contoured design, e.g., to permit comfortable, ergonomic operation. Such a design may also permit treatment of multiple areas of a subject without requiring a subject to move during treatment of multiple areas, in contrast to other, larger medical treatment systems. A main body may be readily disassembled, cleaned, and sterilized (e.g., by steam, heat, chemical, or UV light sterilization).

In some embodiments, a main body may be configured to couple with a needle (e.g., a hollow needle). A main body may have a locking mechanism to secure a needle in place during operation. A locking mechanism may allow for a mechanical and/or electrical connection with additional components (e.g., one or more actuators that can be used to operate a needle). Locking a main body and a needle may be used to establish a fluidic connection between, e.g., a hollow needle, a reservoir, and/or a pressure generating source, e.g., a negative or positive pressure generating source. A main body-needle locking mechanism may be engaged and disengaged repeatably. A main body-needle locking mechanism may include one or more of adhesive, magnetic, electrical, and/or mechanical components (e.g., one or more gaskets, o-rings, septa, springs, clasps, and other engagement members).

In some embodiments, a main body may include a groove or depression for placement of an o-ring (e.g., a viton o-ring, a nitrile rubber o-ring, and a thermoplastic polyurethane o-ring) that will allow for a seal to form between a main body and a needle. A portion of a needle engineered to engage with a main body may include a corresponding groove or depression. A locking mechanism may include, e.g., mated pieces made of molded plastic. A main body may also feature a mechanism to activate detachment of a needle from a main body. Such a mechanism may include one or more of a button, key, switch, toggle, spin-wheel, touch screen, and/or sliding lock. A detachment mechanism may be a quick-release mechanism. A main body may include a depressible portion that engages a seal when a needle is slidably engaged with a main body. A needle may be disengaged from a main body by depressing a depressible portion in a main body. Disengagement of a needle from a main body may be activated by a sliding lock, so as to eliminate a seal between a needle and a main body to allow their separation.

In some embodiments, a main body may include additional components, such as a tensioner (e.g., a spring), a position sensor, a reservoir for collecting waste materials (e.g., tissue, blood, and/or interstitial fluids), a positive or negative pressure generating source (e.g., a vacuum pump, suction source, evacuated chamber, and/or high pressure fluid jet), tubing and/or cables to couple various components, device control electronics and/or activation mechanisms, a power supply (e.g., an alternator and/or battery component), and/or a user interface. Components of a main body may be provided to an operator (e.g., a doctor or surgeon) in sterile condition prior to use on a patient and many, if not all, of the components can be re-sterilized or replaced with sterile components prior to a subsequent use.

In some embodiments, a main body may include a trough at a first end of a main body. A main body having a trough may be used together with a guide rail that has a raised backbone, such that a trough at a first end of a main body may be configured to fit on top of a raised backbone of a guide rail. Alternatively, a guide rail may include a trough, such that a first end of a main body may be configured to fit within a trough in a guide rail. A first end of a main body may include protrusions (e.g., protrusion 96, see FIGS. 6B-6D) that fit within openings or indentations in a guide rail. A position sensor may be disposed inside a main body and configured to detect openings and/or indentations in a guide rail.

Guide Rail

In some embodiments, technologies, devices and/or methods described herein comprise a system comprising for cosmetic resurfacing comprising a guide rail as a component. A guide rail provides a template or track for a main body and a hollow needle. A guide rail may be placed onto a surface of skin tissue prior to engagement of a main body. A guide rail may include multiple openings and/or indentations. Openings and/or indentations in a guide rail mark positions for a needle to insert into skin tissue.

In some embodiments, a guide rail may have a flat surface and a raised backbone. A guide rail having a flat surface and a raised backbone may be used with a main body having a trough at a first end of the main body, as described previously. A raised backbone may have multiple indentations. Each indentation may mark a position for needle (e.g., a hollow needle) insertion and may be detected by a position sensor disposed inside a first end of a main body, if present. Once a trough at a first end of the needle is mounted onto a raised backbone of a guide rail, a main body may advance along a raised backbone of a guide rail by following indentations. Each indentation can be aligned with an opening on a flat surface of a guide rail. A needle may be mechanically released from a main body whenever a main body detects an indentation, such that a needle extends through an opening and inserts into skin tissue.

In some embodiments, a guide rail may have a trough that includes multiple indentations and openings. A main body may be configured such that a first end of a main body fits within a trough. A first end of a main body may also include a protrusion, which may be configured to fit within each indentation in a trough of a guide rail. Indentations in a trough may be configured to have different geometries to accommodate protrusion and/or a first end of a main body. In some embodiments, once a main body including a needle is mounted within a trough of a guide rail, a position sensor within the main body may detect the indentations and openings in a trough. As a first end of a main body engages with each indentation, a main body may mechanically release a needle to extend through an opening in the trough of a guide rail and insert into skin tissue.

In some embodiments, a tensioner (e.g., a spring) may be disposed inside a main body and may be used to withdraw a needle (e.g., a hollow needle) from skin tissue before a main body is advanced to the next indentation in the guide rail. A guide rail may remain stationary as a main body travels along its length. In some embodiments, a main body may use every indentation and opening in a guide rail to insert and withdraw a needle in an area of skin that a guide rail covers. In some embodiments, only a subset of indentations and openings in a guide rail may be used. A guide rail may be placed at different parts of skin to provide a track for a main body and hollow needle.

Figure 5B:
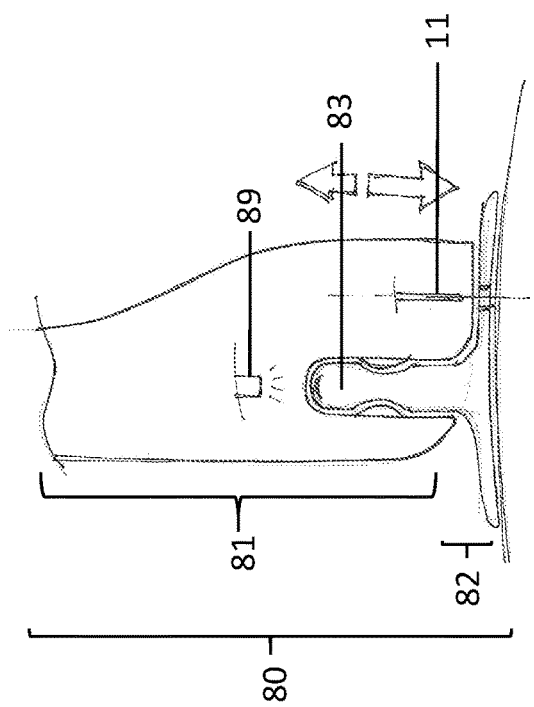
FIG. 5B is a schematic illustration showing a cross-sectional view of system 80 of FIG. 5A.
Figure 5A:
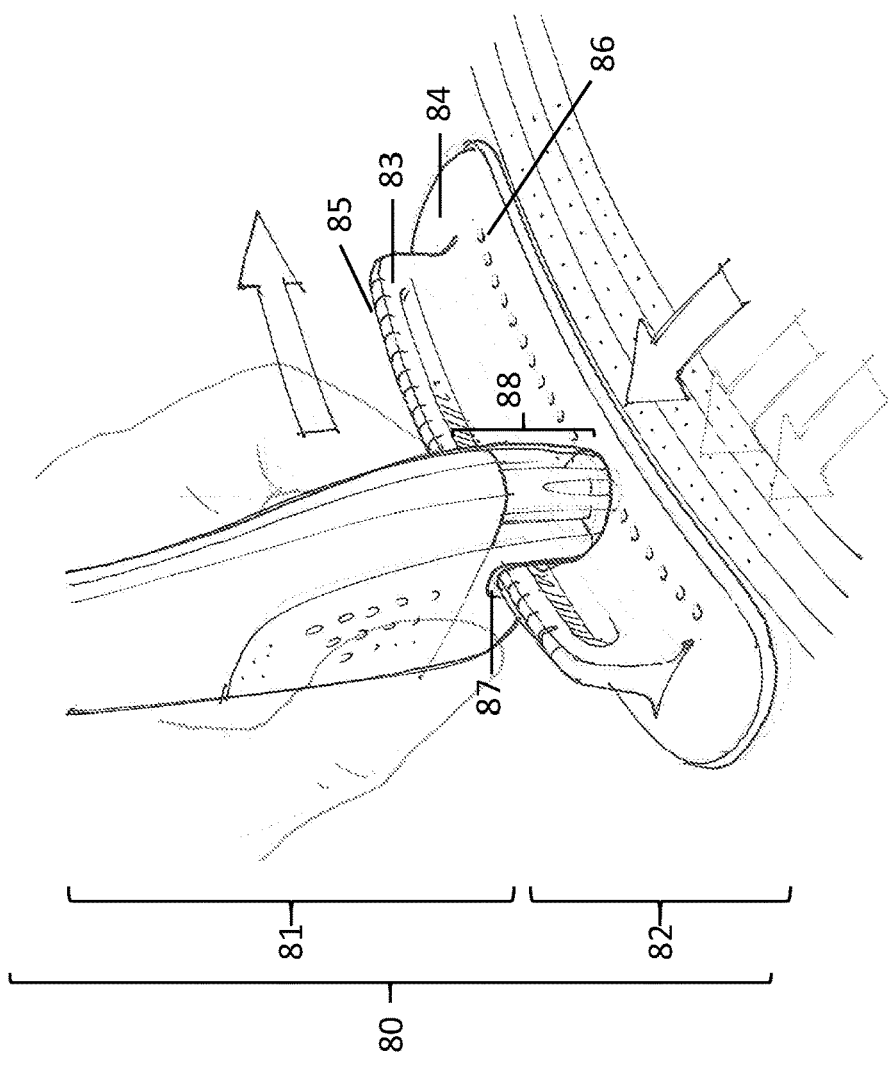
FIG. 5A is a schematic illustration showing system 80 including main body 81 and guide rail 82 featuring raised backbone 83.

Two examples of systems including a guide rail and a main body having a needle (e.g., a hollow needle) mounted inside the main body are illustrated in FIGS. 5A, 5B, and 6A-6D. FIGS. 5A and 5B show system 80, which includes needle 11 (e.g., a hollow needle) mounted within main body 81 and guide rail 82 having raised backbone 83 and flat surface 84. Raised backbone 83 includes multiple indentations 85. Flat surface 84 includes multiple openings 86. Main body 81 includes trough 87 at first end 88 and position sensor 89 mounted within main body 81.

Figure 6D:
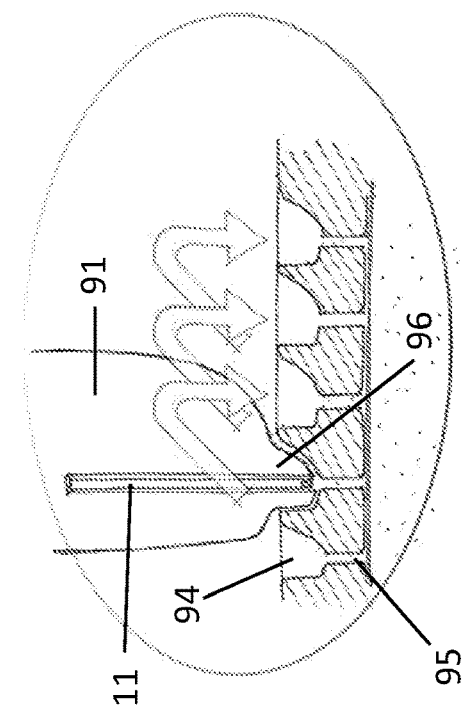
FIG. 6D is a schematic illustration showing an enlarged view of main body 91 featuring protrusion 96 that is configured to fit into indentation 94.
Figure 6C:
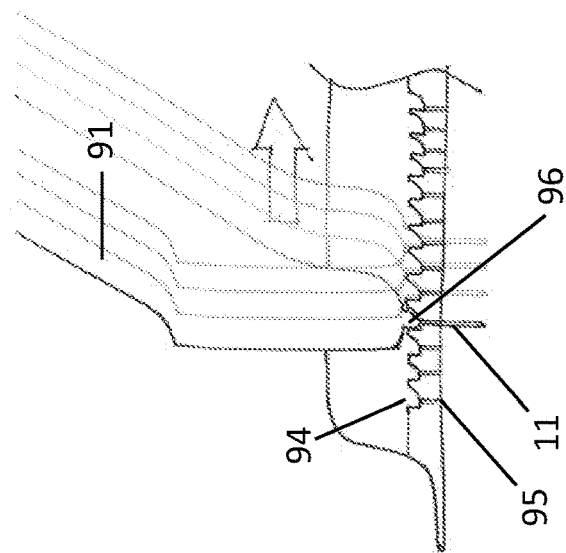
FIGS. 6B and 6C are schematic illustrations showing cross-sectional views of system 90 of FIG. 6A.
Figure 6B:
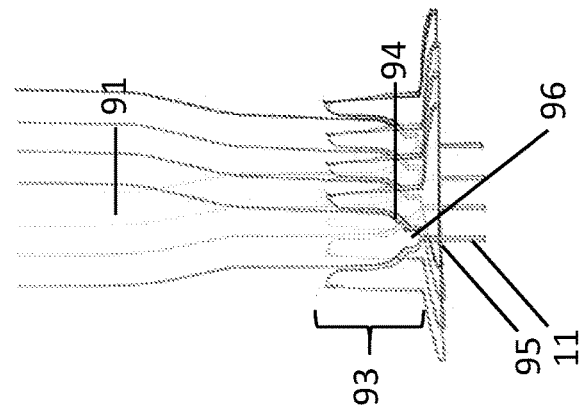

FIGS. 6A-6D show system 90, which includes needle 11 mounted within main body 91 and guide rail 92 having trough 93. Trough 93 includes multiple indentations 94 and openings 95. Main body 91 has protrusion 96, which is configured to fit within indentation 94 (FIG. 6D).

Devices Including Needles and/or Staples

In some embodiments, technologies, devices and/or methods described herein comprise devices that use needles (e.g., hollow needles) or staples (e.g., hollow staples) to debulk skin tissue (e.g., removing tissue portions from the skin) and/or to trigger biological responses that contribute to tissue resurfacing and remodeling. In some embodiments, needles (e.g., hollow needles) and/or staples (e.g., hollow staples) may be mounted onto a support base, which may be configured to fit within a main body. A main body may be configured to include mechanisms and components that function together to engage a support base, thereby ejecting a support base comprising a plurality of needles and/or staples, and wherein needles or staples insert into skin tissue when in contact therewith.

Bladder Configuration

In some embodiments, technologies, devices and/or methods described herein comprise a support base that is at least one inflatable bladder. An inflatable bladder may be connected to an external device or devices that supply fluid (e.g., air, gas, and/or liquid) pressure (e.g., positive and/or negative pressure) to an inflatable bladder in order to inflate and/or deflate a bladder. An inflatable bladder may have a first surface and a second surface. A first surface of the inflatable bladder may be configured to engage with needles (e.g., hollow needles) and/or staples (e.g., hollow staples) and a second surface of an inflatable bladder may be configured to contact skin tissue. An inflatable bladder may be placed in a cartridge in a main body of a device. Alternatively, an inflatable bladder may be incorporated into, or act as, a template or a guide rail that functions to provide tracks for a needle (e.g., a hollow needle) and/or staple (e.g., a hollow staple) to follow. An inflatable bladder may be configured to adhere to skin tissue once it is in contact with skin tissue. For example, the exterior of a second surface of an inflatable bladder may further include an adhesive material on one or more portions of a second surface (e.g., the surface that is in contact with the skin tissue). An inflatable bladder may further include a releasable backing material that covers an adhesive material on a second surface that can be removed (e.g., peeled off) to expose adhesive material prior to applying a bladder to skin tissue. An adhesive material may be a pressure sensitive adhesive (PSA), a non-reactive adhesive, a contact adhesive, a hot melt adhesive, a reactive adhesive, a one-part adhesive, a natural adhesive, and/or a synthetic adhesive. For example, an adhesive material may be an elastomer, a thermoplastic, an emulsion, and/or a thermoset, such as acrylic, synthetic or natural rubber, ethylene-vinyl acetate (EVA), nitrile, silicone (e.g., a siliconized material), styrene block copolymer, and/or vinyl ether.

In some embodiments, an inflatable bladder may also include openings that indicate positions for needles (e.g., hollow needles) and/or staples (e.g., hollow staples) to insert into skin tissue. Prior to insertion of needles and/or staples, an inflatable bladder is in a collapsed form. Needles and/or staples may be mounted onto an inflatable bladder, which may be contained, e.g., in a cartridge within a main body of a device configured for handheld operation. A main body may further include mechanisms and components (e.g., a tensioner) that function together to release needles and/or staples from a main body.

A main body may be configured to release an inflatable bladder comprising needles and/or staples on skin tissue. For example, two ends (e.g., two legs) of a staple may insert into skin tissue through openings in an inflatable bladder (see FIGS. 7A-7D). Legs of a staple may have the same or different diameters and/or lengths. A main body may further include a position sensor that detects openings in an inflatable bladder.

In some embodiments, an inflatable bladder may be inflated to withdraw needles (e.g., hollow needles) and/or staples (e.g., hollow staples) from skin tissue. An inflatable bladder may be connected to an external device that supplies fluid (e.g., air, gas, or liquid) pressure (e.g., positive and/or negative pressure) to an inflatable bladder in order to inflate and/or deflate a bladder. As a bladder inflates, it may push needles and/or staples out from skin tissue to be removed. Needles and/or staples may be removed while a bladder still remains on a skin surface. In some embodiments, an entire bladder, either in collapsed or inflated form, together with needles and/or staples, may be removed (e.g., peeled off) from a skin surface. An inflatable bladder may be disposable or may be sterilized for subsequent use. Placement of an inflatable bladder on a skin surface may be arranged to achieve a desired hole pattern and/or density. For example, as shown in FIG. 7E, subsequent placements of an inflatable bladder may overlap each other to achieve a high density of holes, in which the distance between adjacent holes is smaller than the distance between the two ends of a staple (e.g., a hollow staple).

In one configuration, a device may include a main body that comprises a cartridge comprising two or more (e.g., two) inflatable bladders placed in close proximity to each other. Needles (e.g., hollow needles) may be placed between adjacent inflatable bladders. A device may be configured to eject bladders and needles onto skin tissue, in which bladders can adhere to skin tissue and needles can insert into skin tissue. Bladders on skin tissue may be inflated at the same time, thereby withdrawing needles, which are placed between bladders, from skin tissue.

Figure 7B:
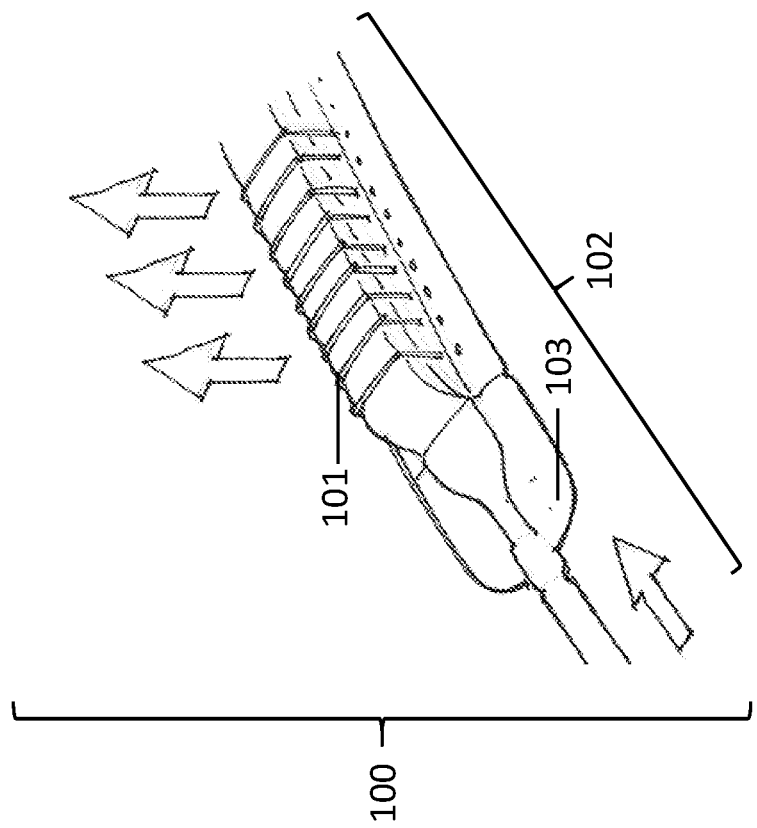
FIGS. 7A and 7B are schematic illustrations showing device 100 including staples 101 (e.g., hollow staples) and inflatable bladder 102 in collapsed (FIG. 7A) and inflated (FIG. 7B) forms.
Figure 7A:
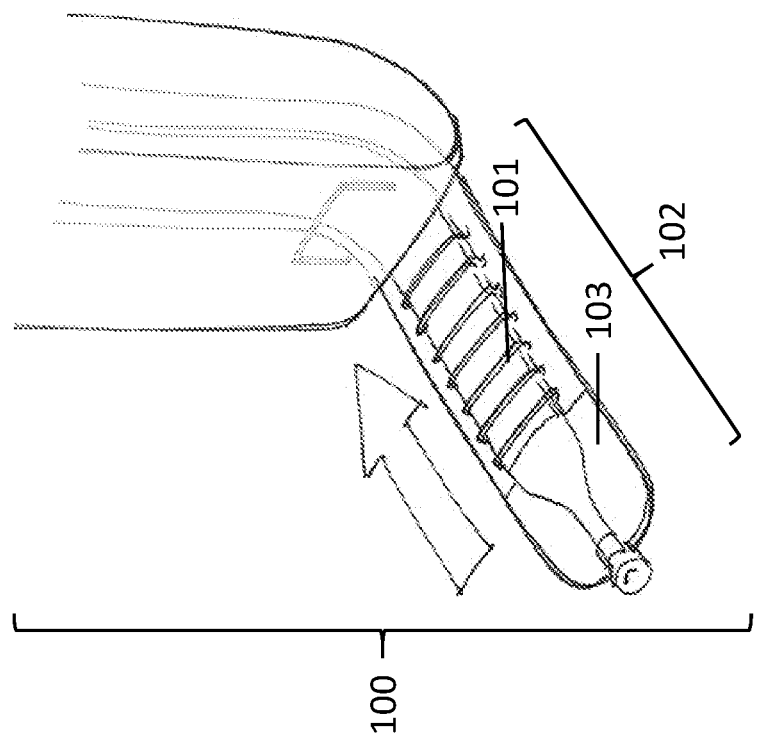
Figure 7E:
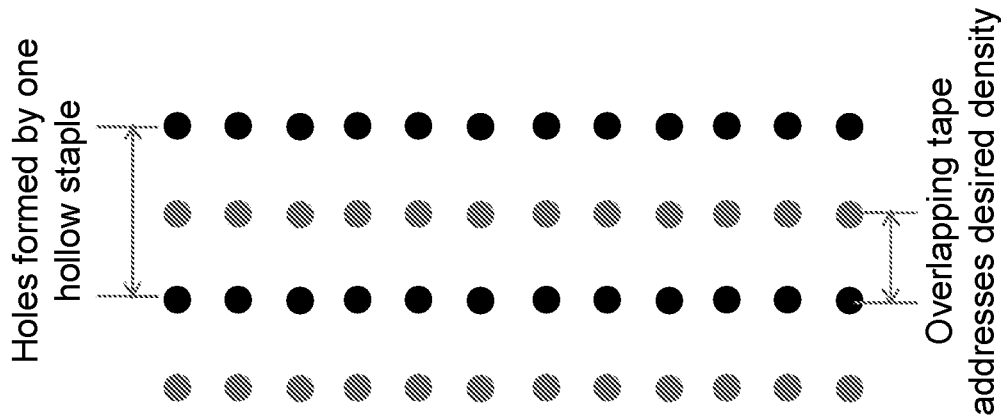
FIG. 7E is a schematic illustration showing holes formed by staples 101 (e.g., hollow staples) of device 100 following protraction and retraction of staples 101, in which the distance between adjacent holes may be smaller than the distance between the two legs of a staple (e.g., if the positions of inflatable bladder 102 overlap each other).
Figure 7D:
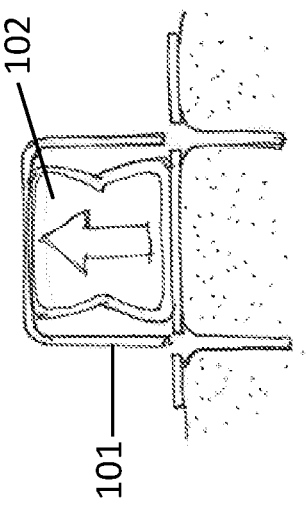
FIGS. 7C and 7D are schematic illustrations showing enlarged, cross-sectional views of device 100 featuring inflatable bladder 102 in collapsed (FIG. 7C) and inflated (FIG. 7D) forms.
Figure 7C:
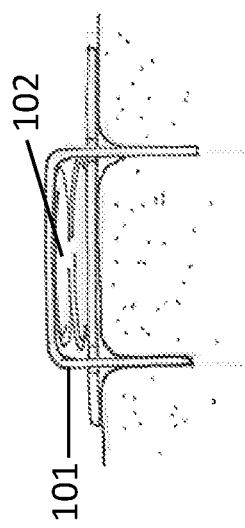
Figure 8A:
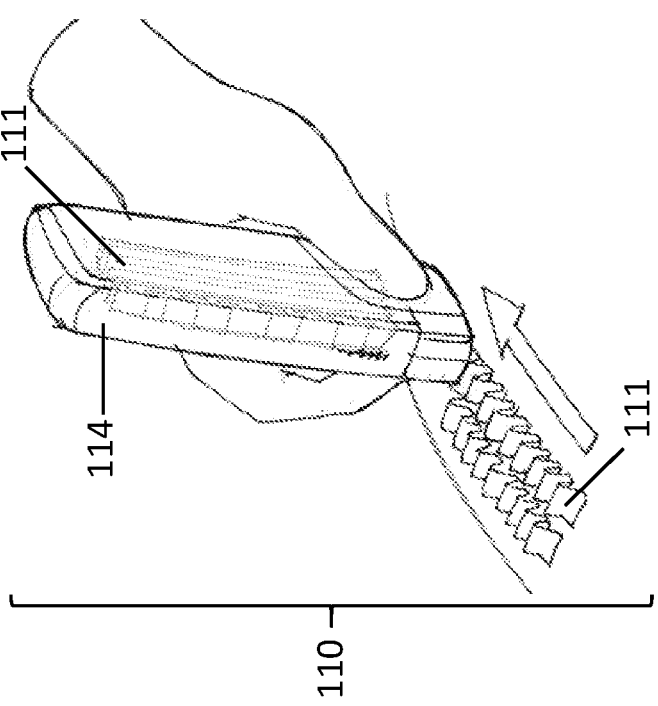
FIG. 8A is a schematic illustration showing device 110 including folded tape 111 and main body 114.
Figure 8B:
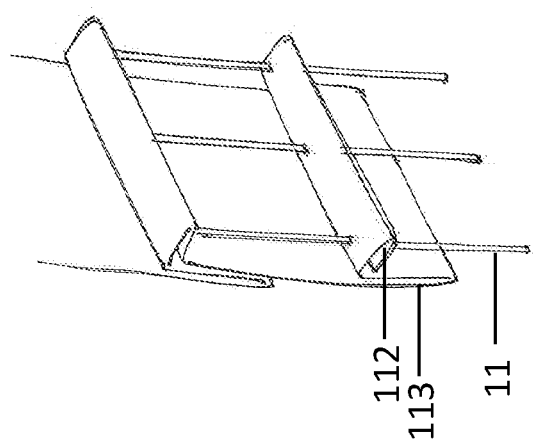

In another configuration, a device having a bladder and staples (e.g., hollow staples) is shown in FIGS. 7A-7D. Device 100 includes staples 101 (e.g., hollow staples) that are configured to insert into the skin tissue over first surface 103 of inflatable bladder 102, which is in a collapsed form (FIG. 7A). Staples 101 may be inserted or "stapled" into the skin tissue by a main body. Inflatable bladder 102 may be connected to an external device, which can supply air to inflate the bladder (FIG. 7B). As shown in FIG. 7B, staples 101 are pushed out of the skin tissue once the bladder is inflated. FIGS. 7C and 7D further illustrate cross-section views of inflatable bladder 102 in collapsed and inflated forms, respectively, and staple 101 on top of inflatable bladder 102.

Tape Configuration

In some embodiments, technologies, devices and/or methods described herein comprise needles (e.g., hollow needles) that are affixed onto a support base. Needles and a support base may be disposed inside a main body configured for handheld operation. A support base may be, e.g., a folded tape. Multiple needles may be attached to a first surface of a folded tape. Ends of needles may be attached to a first surface of a folded tape. A tape may be folded such that multiple folded ledges and/or service loops may be formed. Ends of needles may be attached to folded ledges of a tape, such that the length of a needle may be parallel to a first surface of a tape. A folded tape and needles may be configured to fit inside a main body of an applicator device, which may further include mechanisms and/or components that function together to release a portion of a folded tape to insert one or more of needles into skin tissue.

In some embodiments, needles (e.g., hollow needles) may be withdrawn from skin tissue by removing (e.g., peeling off) a tape. In some embodiments, a tape and/or the needles may be disposable or sterilized for subsequent use. In some embodiments, new tape and/or needles may be mounted into a main body of an applicator device. The number of needles that may fit onto a ledge of a folded tape may depend on the size of needles, length of tape, width of the tape, and/or desired density of the generated holes. For example, 1-100 needles (e.g., hollow needles) (e.g., 1-95, 1-90, 1-85, 1-80, 1-75, 1-70, 1-65, 1-60, 1-55, 1-50, 1-45, 1-40, 1-35, 1-30, 1-25, 1-20, 1-15, 1-10, 1-5, or 1-3 needles) may fit onto a ledge of a folded tape. For example, if a high density of holes is desired, more needles may be affixed onto each ledge of a folded tape.

FIGS. 8A-8D illustrate device 110 including folded tape 111 and needles 11 (e.g., hollow needles) attached to folded tape 111. Folded tape 111 may include folded ledge 112 and service loop 113. One or more of needles 11 may be attached to each ledge 112. Folded tape 111 and attached needles 11 may be mounted inside main body 114 of an applicator device configured for handheld operation.

Apparatuses Including Paddles

In some embodiments, technologies, devices and/or methods described herein comprise an apparatus that is configured to debulk skin tissue (e.g., removing tissue portions from skin) and/or trigger biological responses that contribute to tissue resurfacing and/or remodeling by contacting skin tissue within an apparatus. In some embodiments, an apparatus may include a first paddle including a distal end and a proximal end, wherein a distal end includes an inner surface and an outer surface and a plurality of needles embedded therebetween, a second paddle including a distal end and a proximal end, wherein a distal end includes an inner surface and an outer surface, and a handle connecting proximal ends of the first and second paddles, in which distal ends of the first and second paddles are configured to press together to contact skin tissue. Skin tissue may be contacted between an inner surface of a first paddle and an inner surface of a second paddle. A handle may include one or more switches that activate needles to extend through an inner surface of a first paddle to insert into skin tissue.

In some embodiments, for example, a plurality of needles (e.g., hollow needles) may be embedded within a first paddle, e.g., between inner and outer surfaces of a first paddle. An inner surface of a first paddle may include multiple openings for needles (e.g., hollow needles) to extend through. In some embodiments, needles may be directly attached to an inner surface of a first paddle. In some embodiments, needles may be arranged in different clusters, in which each cluster has a different density of needles, or needles may be uniformly placed along a surface of a first paddle. Needles may be in a first position, in which tips of needles are aligned with openings on an inner surface of a first paddle. When first and second paddles are pressed together to contact a skin tissue, needles may be activated by, e.g., through a switch on a handle, to translate from a first position to a second position, in which tips of needles extend through openings on an inner surface of a first paddle to insert into skin tissue.

In some embodiments, a handle of an apparatus may include a mechanism for choosing and/or activating a needle (e.g., a hollow needle) cluster with a desired needle density. A handle may include one or more of a lever, button, key, switch, toggle, spin-wheel, touch screen, and/or sliding lock that is used to activate needles. For example, prior to contacting skin tissue between first and second paddles, a needle cluster with the desired density may be chosen using, e.g., a lever, on a handle of an apparatus. Once a needle cluster is chosen and skin tissue is contacted between first and second paddles, an activation button may be used to activate translation of needles (e.g., hollow needles) from a first position to a second position, thereby inserting needles into skin tissue.

Figure 9B:
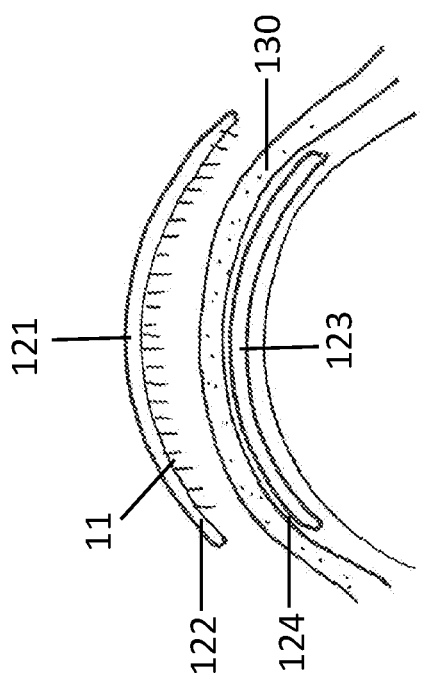
FIG. 9B is a schematic illustration showing an enlarged, cross-sectional view of eyelid 130 contacted between first paddle 121 and second paddle 123 of apparatus 120.
Figure 9A:
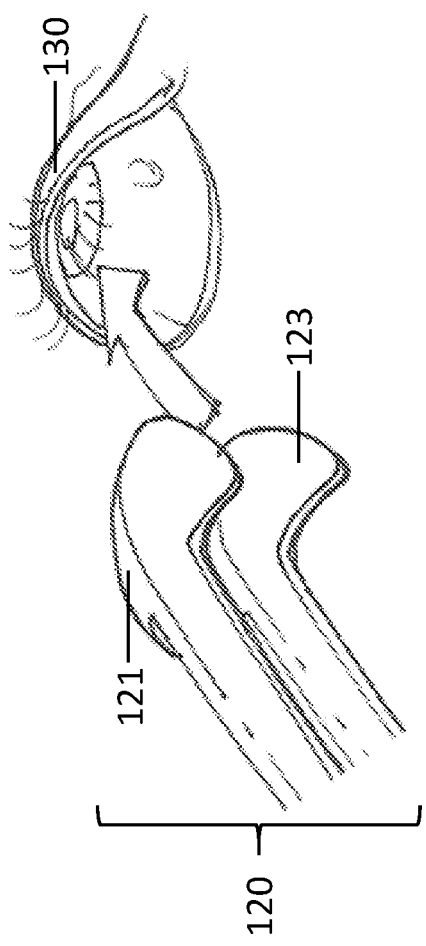
FIG. 9A is a schematic illustration showing apparatus 120 including first paddle 121 and second paddle 123.
Figure 9E:
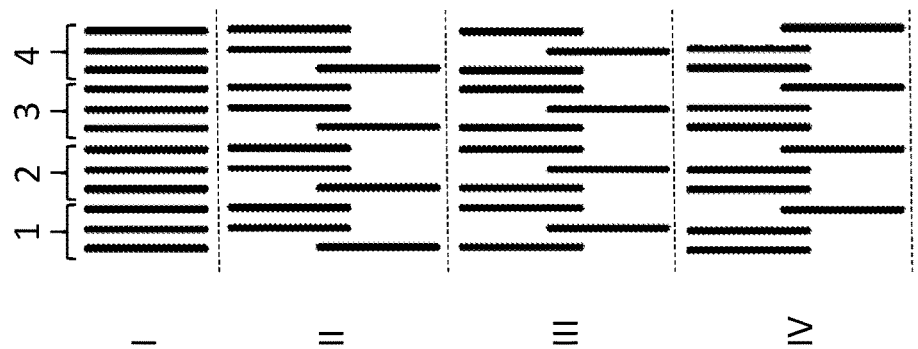
FIG. 9E is a schematic illustration showing multiple needles including three needle clusters shown in four separate zones. The needles in the different zones may be chosen and activated using handle 125, lever 126, and activation button 128 of apparatus 120 to achieve different insertion patterns I-IV.
Figure 9D:
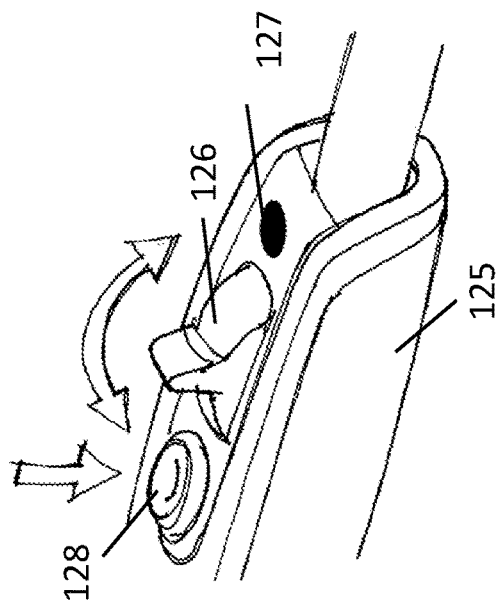
FIGS. 9C and 9D are schematic illustrations showing handle 125 of apparatus 120 featuring lever 126, indicator 127, and activation button 128.
Figure 9C:
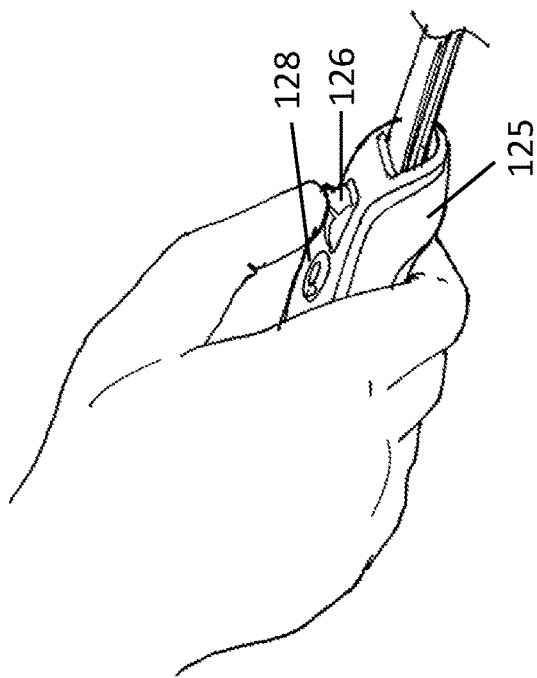

In some embodiments, an apparatus may be used to generate holes on an eyelid, a lip (e.g., an upper lip), or other skin regions that can be placed between paddles. For example, skin (e.g., skin of an eyelid or a lip (e.g., an upper lip)) could be puckered and/or placed between first and second paddles. In this configuration, needles may be embedded within both first and second paddles. As shown in FIGS. 9A and 9B, eyelid 130 may be contacted between inner surface 122 of first paddle 121 and inner surface 124 of second paddle 123 of apparatus 120. Needles 11 (e.g., hollow needles) may be embedded within first paddle 121 and extend from inner surface 122 to insert into eyelid 130. FIGS. 9C and 9D illustrate handle 125 including lever 126, which may be used to choose a needle cluster with desired density, indicator 127, which shows the chosen needle cluster, and activation button 128, which may be used to translate needles 11 from the first position, in which the needles are aligned with the openings on inner surface 122, to the second position, in which the needles are extended from inner surface 122 to insert into eyelid 130. FIG. 9E shows multiple needles including three needle clusters, each of which can be chosen using lever 126 and activated using activation button 128. Different needle clusters may be used sequentially to achieve a high density of holes.

Needles and Staples

In some embodiments, technologies, devices and/or methods described herein comprise needles (e.g., hollow needles) and/or staples (e.g., hollow staples). Needles and/or staples may include and/or be formed of a variety of materials. For example, needles and/or staples may be made of molded plastic, metal, glass, or a combination thereof. Needles and/or staples may also have coatings including chemical coatings. Such coatings may include therapeutic agents as described herein.

In some embodiments, a needle is a solid needle. In some embodiments, a needle is a hollow needle. In some embodiments, a needle comprises one opening. In some embodiments, a needle comprises more than one opening, e.g., a vent and/or a valve.

In some embodiments, a staple is a solid rod or hollow tube comprising at least one bend, kink, elbow, and/or curve. In some embodiments, a staple may include two or more ends or legs (e.g., two, three, four, five, six, seven, eight, nine, or ten ends or legs), in which each end may insert into skin tissue.

In some embodiments, a staple is a solid staple. In some embodiments, a staple is a hollow staple. A hollow staple refers to a staple having at least one end or leg that is hollow. In some embodiments, legs of a staple are parallel to each other, i.e., at an angle that is substantially zero degrees. In some embodiments, legs of a staple are aligned with each other, i.e., at an angle that is substantially 180 degrees. In some embodiments, legs of a staple are at one or more angels to each other, e.g., 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, or over 180 degrees. In some embodiments, legs of a staple have one or more connecting elements between legs. In some embodiments, legs of a staple are connected directly to each other, e.g., in a V-shape. In some embodiments, a staple comprises a vent or a valve that allows for discharge of gas (e.g., air) from a staple. In some embodiments, a staple may have any cross-sectional shape, e.g., round, oval, square, diamond, triangular, hexagonal etc. In some embodiments, a leg of a staple may be substantially straight or may have a bent, curled, saw-tooth, corkscrew, or other configuration. In some embodiments, a leg of a staple may have a position relative to another staple that is different after deployment compared to before deployment. In some embodiments, a leg of a staple may have a position relative to another staple that is the same after deployment compared to before deployment.

All technologies, devices and/or methods described herein may be applied and/or performed using one or more solid needles, one or more hollow needles, one or more solid staples, one or more hollow staples, or any combination thereof.

Gauges, Diameters, and Lengths

In some embodiments, needles (e.g., hollow needles) and/or staples (e.g., hollow staples) may be of varying sizes and geometries. Gauge, diameter (e.g., inner diameter fora hollow staple), and length of a staple are used to describe one or more legs of a staple. A staple may include two or more legs (e.g., two, three, four, five, six, seven, eight, nine, or ten legs), in which each leg may insert into skin tissue. A hollow staple refers to a staple having at least one leg that is hollow. Legs of a hollow staple may have the same or different gauges, inner diameters, and/or lengths. A needle (e.g., a hollow needle) and/or a staple (e.g., a hollow staple) may be of any gauge, including gauges of from 18 to 30 (e.g., 18, 19, 20, 21, 22, 23, 24, 25, 26, 27, 28, 29, or 30 gauge). The gauges of a needle or staple may be from 20 to 26 (e.g., 20, 21, 22, 23, 24, 25, or 26 gauge). A needle (e.g., a hollow needle) or staple (e.g., a hollow staple) may have a diameter (e.g., inner diameter for a hollow needle or a hollow staple) of from about 0.14 mm to about 0.84 mm (e.g., 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, or 0.84 mm). The inner diameter of a hollow needle refers to the diameter of the inner lumen of the hollow needle. The inner diameter of a hollow staple refers to the diameter of the inner lumen of one or more legs of the hollow staple. The inner diameter of a hollow needle or hollow staple may be from about 0.24 mm to about 0.40 mm (e.g., 0.24, 0.25, 0.26, 0.27, 0.28, 0.29, 0.3, 0.31, 0.32, 0.33, 0.34, 0.35, 0.36, 0.37, 0.38, 0.39, or 0.4 mm). Accordingly, the diameter of a portion of skin tissue removed by a hollow needle or hollow staple (e.g., a cored tissue portion) generally corresponds to the inner diameter of the hollow needle or hollow staple.

In some embodiments, a diameter of a needle (e.g., a hollow needle) may vary across its lengths, such that the diameter of one region of the needle may be different from the outer and/or inner diameter of another region of the same needle. A change in a diameter across a needle may or may not be continuous. A needle may or may not be entirely cylindrical. For example, one or more needles (e.g., hollow needles) may be rectangular, serrated, scalloped, and/or irregular in one or more dimensions and along some or all of their lengths. In some embodiments, an inner lumen diameter may vary along a length of a hollow needle. In some embodiments, a needle (e.g., a hollow needle) is a swaged needle having a bevel angle α of between about 5 and 40 degrees (e.g., between about 6 and about 40 degrees (e.g., 8, 10, 12, 14, 16, 18, 20, 22, 24, 26, 28, 30, 32, 34, 36, 38, or 40 degrees)) and a variable inner lumen diameter over its length. A needle (e.g., a hollow needle) may also have a bevel angle α of at least about 20 degrees (e.g., between about 20 and about 40 degrees (e.g., 20, 22, 24, 26, 28, 30, 32, 34, 36, 38, or 40 degrees). In other embodiments, a diameter may be wider at the proximal end of a needle (e.g., away from the tip that penetrates the skin). This may facilitate the removal of the cored tissue portion from the hollow needle, may limit the need for clearing of the hollow needle, and may reduce the occurrence of needle clogging.

In some embodiments, a needle (e.g., a hollow needle) or staple (e.g., a hollow staple) may be of varying lengths and may have varying active lengths (e.g., a length of a needle configured to penetrate skin tissue). A length or active length of a staple refers to a length of one or more legs of a staple. In some embodiments, legs of a staple may have the same or different lengths. Active lengths may vary from about 0.3 mm to about 10 mm (e.g., 0.3, 0.4, 0.5, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10 mm) and may be selectable with manual or automatic controls (e.g., a scroll wheel or an actuation mechanism, such as an electromagnetic actuator). Active lengths of a needle or staple may be adjusted and selected depending on the skin area needing treatment. For example, needles or staples with active lengths from about 0.3 mm to about 2 mm (e.g., 0.3, 0.4, 0.5, 0.6, 0.8, 1, 1.2, 1.4, 1.6, 1.8, or 2 mm) may be used to treat thin skin, e.g., skin of an eyelid. Thickness of the epidermal and/or dermal layers of the skin of an eyelid may be from about 0.3 mm to about 1 mm (e.g., 0.3, 0.4, 0.5, 0.6, 0.8, or 1 mm). Needles (e.g., hollow needles) or staples (e.g., hollow staples) with active lengths from about 5 mm to about 10 mm (e.g., 5, 6, 7, 8, 9, and 10 mm) may be used to treat thick skin, e.g., skin of the back or scar tissue, which can be thicker than healthy skin tissue. Thickness of an epidermal layer of skin may be from about 0.05 to about 2 mm (e.g., 0.05 to 2, 0.05 to 1.95, 0.05 to 1.9, 0.05 to 1.85, 0.05 to 1.8, 0.05 to 1.75, 0.05 to 1.7, 0.05 to 1.65, 0.05 to 1.6, 0.05 to 1.55, 0.05 to 1.5, 0.05 to 1.45, 0.05 to 1.4, 0.05 to 1.35, 0.05 to 1.3, 0.05 to 1.25, 0.05 to 1.2, 0.05 to 1.15, 0.05 to 1.1, 0.05 to 1.05, 0.05 to 1, 0.05 to 0.95, 0.05 to 0.9, 0.05 to 0.85, 0.05 to 0.8, 0.05 to 0.75, 0.05 to 0.7, 0.05 to 0.65, 0.05 to 0.6, 0.05 to 0.55, 0.05 to 0.5, 0.05 to 0.45, 0.05 to 0.4, 0.05 to 0.35, 0.05 to 0.3, 0.05 to 0.25, 0.05 to 0.2, 0.05 to 0.15, 0.05 to 0.1, 0.1 to 2, 0.15 to 2, 0.2 to 2, 0.25 to 2, 0.3 to 2, 0.35 to 2, 0.4 to 2, 0.45 to 2, 0.5 to 2, 0.55 to 2, 0.6 to 2, 0.65 to 2, 0.7 to 2, 0.75 to 2, 0.8 to 2, 0.85 to 2, 0.9 to 2, 0.95 to 2, 1 to 2, 1.05 to 2, 1.15 to 2, 1.2 to 2, 1.25 to 2, 1.3 to 2, 1.35 to 2, 1.4 to 2, 1.45 to 2, 1.5 to 2, 1.55 to 2, 1.6 to 2, 1.65 to 2, 1.7 to 2, 1.75 to 2, 1.8 to 2, 1.85 to 2, 1.9 to 2, and 1.95 to 2 mm). The thickness of a dermal layer of skin may be from 2 to 8 mm (e.g., 2 to 8, 2 to 7.5, 2 to 7, 2 to 6.5, 2 to 6, 2 to 5.5, 2 to 5, 2 to 4.5, 2 to 4, 2 to 3.5, 2 to 3, 2 to 2.5, 2.5 to 8, 3 to 8, 3.5 to 8, 4 to 8, 4.5 to 8, 5 to 8, 5.5 to 8, 6 to 8, 6.5 to 8, 7 to 8, or 7.5 to 8 mm). Active lengths of a needle (e.g., a hollow needle) or staple (e.g., a hollow staple) may be adjusted and selected to penetrate an epidermal and/or dermal layer of skin.

In some embodiments, a staple may include two or more legs or ends (e.g., two, three, four, five, six, seven, eight, nine, or ten ends or legs), in which each leg or end may insert into the skin tissue. A hollow staple refers a staple having at least one leg or end that is hollow. For example, a leg of a staple (e.g., a hollow staple) may have an active length from about 1 mm to about 10 mm (e.g., 1, 2, 3, 4, 5, 6, 7, 8, 9, or 10 mm). A leg of a hollow staple may have a gauge that is from 20 to 26 (e.g., 20, 21, 22, 23, 24, 25, or 26 gauge). Distance between two legs of a staple (e.g., a hollow staple may be between about 0.1 mm and about 3 mm (e.g., 0.1, 0.2, 0.4, 0.6, 0.8, 1, 1.2, 1.4, 1.6, 1.8, 2, 2.2, 2.4, 2.6, 2.8, or 3 mm).

In some embodiments, parameters of a needle (e.g., a hollow needle) or a staple (e.g., a hollow staple) for use in the technologies, articles, apparatuses, systems, kits, and methods described herein may be selected based on an area of skin and a condition to be treated. For example, treatment of thin, lax skin on the cheeks may benefit from a needle (e.g., a hollow needle) or a staple (e.g., a hollow staple) having an active length of about 2 mm and medium gauge (e.g., 25 gauge), while treatment of thick skin, e.g., on the back, or treatment of scar tissue may benefit from a needle or staple having an active length closer to 5 mm and a thicker gauge (e.g., 22 gauge). A needle (e.g., a hollow needle) or staple (e.g., a hollow staple) may be configured to extend to varying depths of skin tissue. Depth of penetration of a needle or staple may be determined by the active length (e.g., from about 2 mm to about 5 mm) of a needle or staple. A needle (e.g., a hollow needle) or staple (e.g., a hollow staple) may be configured to extend (i) into a dermal layer, (ii) through an entire dermal layer to a junction of a dermal layer and a subcutaneous fat layer, and/or (iii) into a subcutaneous fat layer.

Prongs

In some embodiments, technologies, devices and/or methods described herein comprise one or more needles and/or staples, wherein a distal end of a needle (e.g., a hollow needle) or a staple (e.g., a hollow staple) may include one or more prongs. A distal end of a staple refers to the distal end of one or more legs of a staple. In some embodiments, a needle includes at least a first prong. In some embodiments, one or more legs of a staple include at least a first prong. A longitudinal axis of a staple refers to the longitudinal axis of a leg of a staple.

The geometry of a prong at a distal end of a needle (e.g., a hollow needle) or staple (e.g., a hollow staple) can be characterized by a bevel angle. A bevel angle refers to an angle between a lateral side of a prong and a longitudinal axis of a needle or staple. An angle of "2α" refers to an angle between two lateral sides of a prong of a needle or staple. In some embodiments, a bevel angle α between a lateral side of a prong and a longitudinal axis of a needle or staple may be between about 5 and 40 degrees (e.g., between about 6 and about 40 degrees (e.g., 8, 10, 12, 14, 16, 18, 20, 22, 24, 26, 28, 30, 32, 34, 36, 38, or 40 degrees)). In some embodiments, a bevel angle α may also be at least about 20 degrees (e.g., between about 20 and about 40 degrees (e.g., 20, 22, 24, 26, 28, 30, 32, 34, 36, 38, or 40 degrees)). In some embodiments, an angle between a lateral side of a prong and a longitudinal axis of the needle or staple may be about 30 degrees. For needles (e.g., hollow needles) or staples (e.g., hollow staples) having two or more prongs, each prong may have the same bevel angle or different bevel angles. In one embodiment, for a needle having two prongs, e.g., a first prong and a second prong, an angle between a lateral side of a first prong and a longitudinal axis of a needle may be between about 20 and about 30 degrees (e.g., 20, 22, 24, 26, 28, or 30 degrees) and an angle between a lateral side of a second prong and a longitudinal axis of a needle may be between about 30 and about 40 degrees (e.g., 30, 32, 34, 36, 38, or 30 degrees). For example, a first prong may have a bevel angle α of 20 degrees and a second prong may have a bevel angle α of 30 degrees.

In some embodiments, a tip of a prong of a needle (e.g., a hollow needle) or staple (e.g., a hollow staple) may have an edge. In some embodiments, a tip of a prong of a needle or staple is a flat tip having at least two dimensions. In some embodiments, a prong of a needle or staple includes a tip micro-feature. In some embodiments, needles (e.g., hollow needles) and/or staples (e.g., hollow staples) are constructed to prevent frequent needle damage during use, such as needle tip curling and wear (e.g., becoming dull), needle heel degradation, and needle bending.

In some embodiments, needles (e.g., hollow needles) and/or staples (e.g., hollow staples) may be designed to maintain mechanical integrity and durability over a large number of actuation cycles (e.g., actuation cycles greater than 1,000, 2,000, 3,000, 4,000, 5,000, 6,000, 7,000, 8,000, 9,000, 10,000, 11,000, 12,000, 13,000, 14,000, 15,000, or 20,000) if needles and/or staples are designed to be used for repeated insertions. In some embodiments, hollow needles and/or hollow staples may also effectively remove tissue portions from the skin with high coring rate. To produce a cosmetic effect in the skin tissue, a hollow needle and/or hollow staple is inserted into the skin tissue, preferably to a pre-determined depth using a pre-determined force, such that a hollow needle or hollow staple removes a portion of skin tissue by capturing a portion of skin tissue in a lumen of a hollow needle and/or hollow staple.

In some embodiments, hollow needles and/or hollow staples are designed to maximize coring rate and minimize hollow needle and/or hollow staple actuations that do not result in cored tissue removal. A tissue portion detaches from skin when a coring force exceeds a tissue resistance force. A tissue resistance force is determined by a connection of a tissue portion to its surrounding tissue. For example, when a hollow needle is fully inserted through the dermal layer of skin, a tissue resistance force is determined by a connection between a tissue portion in a lumen of a needle and a subcutaneous fat layer. Coring rate is determined by, e.g., a coring force of a hollow needle, friction between a lumen wall of a hollow needle and a tissue portion, and tissue resistance force. Coring rate may also be affected by applying a pressure differential across a hollow needle or hollow staple. For example, a vacuum applied at the proximal end of a hollow needle may aspirate a cored tissue portion from a hollow needle, thereby, increasing coring rate.

In some embodiments, needles (e.g., hollow needles) or staples (e.g., hollow staples) may be designed for single insertion in skin tissue. A hollow needle or a hollow staple may retain a cored tissue portion in a lumen and be discarded after a single use. A hollow needle or hollow staple designed for single use may include one or more micro-features (described in detailed further herein) that function to help a needle or staple to capture or "grab" and retain a tissue portion to be removed. A lumen of a hollow needle or hollow staple may be coated with a material that increases the roughness of a lumen surface, thus, increasing friction between a lumen surface and a cored tissue portion to help retain a cored tissue portion inside a lumen. Needles or staples may also be coated with a material, e.g., a lubricant, that minimizes insertion force.

In some embodiments, a needle (e.g., a hollow needle) or staple (e.g., a hollow staple) may have one prong at a distal end, two prongs, or more than two prongs (e.g., three, four, five, or six prongs). A needle or staple having one prong may be formed by grinding one side of a distal end of a needle or staple at an angle relative to a longitudinal axis of a needle or staple. A needle or staple having two prongs may be formed by grinding opposite sides of a distal end of a needle or staple at an angle relative to a longitudinal axis of a needle or staple.

In some embodiments, a tip of a prong of a needle (e.g., a hollow needle) or staple (e.g., a hollow staple) may be of varying geometries. For example, a tip of a prong may have a sharp point or an edge (e.g., a one-dimensional edge). For a prong having an edge at a tip, each of the bevel angles of a prong may be between about 5 and 40 degrees (e.g., between about 6 and about 40 degrees (e.g., 8, 10, 12, 14, 16, 18, 20, 22, 24, 26, 28, 30, 32, 34, 36, 38, or 40 degrees)). In some embodiments, each of the bevel angles of a prong may also be at least about 20 degrees (e.g., from about 20 to about 40 degrees (e.g., about 30 degrees)). For a needle or staple having two or more prongs, e.g., two prongs, prongs may have different bevel angles (e.g., a bevel angle α of about 20 degrees at a first prong and a bevel angle α of about 30 degrees at a second prong). A tip of a prong may be a flat tip (e.g., a flat tip having two dimensions). In some embodiments, a flat tip has a length and a width. A surface (length/width) of a flat tip of a prong may be at an angle relative to a longitudinal axis of a needle or staple. For example, a surface of a flat tip may be perpendicular to a longitudinal axis of a needle or staple (e.g., at a 90 degree angle relative to a longitudinal axis of a needle or staple) or a surface of a flat tip may be at a non-90 degree angle relative to a longitudinal axis of a needle or staple (e.g., between about 3 to about 89 degrees, such as 3 to 89 degrees, e.g., 3, 6, 9, 12, 15, 18, 21, 24, 27, 30, 33, 36, 39, 42, 45, 48, 51, 54, 57, 60, 63, 66, 69, 72, 75, 78, 81, 84, 87, or 89 degrees). A surface of a flat tip may be level or may have different geometry, e.g., arc, groove, or non-level. For a prong having a two-dimensional flat tip, each of the bevel angles of a prong may be between about 5 degrees to about 40 degrees (e.g., 6, 8, 10, 12, 14, 16, 18, 20, 22, 24, 26, 28, 30, 32, 34, 36, 38, or 40 degrees). A needle or staple may have one or two prongs each with a two-dimensional flat tip in which one or both prongs have a bevel angle α of between about 5 to about 40 degrees (e.g., at least about 20 degrees (e.g., from about 20 to about 40 degrees (e.g., about 30 degrees))). Needles or staples having a one-dimensional edge or a two-dimensional flat tip may exhibit a reduced likelihood of needle tip curling.

Micro-Features

In some embodiments, technologies, devices and/or methods described herein comprise a hollow needle or hollow staple that may include one or more micro-features. In some embodiments, a micro-feature is an element of a hollow needle or hollow staple that functions to help a hollow needle or hollow staple to capture or "grab" a tissue portion to be removed. In some embodiments, a micro-feature may increase a coring rate of a hollow needle or hollow staple. In some embodiments, a micro-feature may be located anywhere along an active length of a hollow needle or hollow staple. In some embodiments, for a hollow needle, a micro-feature may be located near a tip of a hollow needle. In some embodiments, for a hollow staple, a micro-feature may be located near a tip of one or more legs of a hollow staple. In some embodiments, a distance between a tip of a prong of a hollow needle or hollow staple and a start of a micro-feature is from about 100 μm to about 5 mm (e.g., from 100 μm to 5 mm, 200 μm to 5 mm, 300 μm to 5 mm, 400 μm to 5 mm, 500 μm to 5 mm, 600 μm to 5 mm, 700 μm to 5 mm, 800 μm to 5 mm, 900 μm to 5 mm, 1 mm to 5 mm, 1.1 mm to 5 mm, 1.2 mm to 5 mm, 1.3 mm to 5 mm, 1.4 mm to 5 mm, 1.5 mm to 5 mm, 1.6 mm to 5 mm, 1.7 mm to 5 mm, 1.8 mm to 5 mm, 1.9 mm to 5 mm, 2 mm to 5 mm, 2.1 mm to 5 mm, 2.2 mm to 5 mm, 2.3 mm to 5 mm, 2.4 mm to 5 mm, 2.5 mm to 5 mm, 2.6 mm to 5 mm, 2.7 mm to 5 mm, 2.8 mm to 5 mm, 2.9 mm to 5 mm, 3 mm to 5 mm, 3.1 mm to 5 mm, 3.2 mm to 5 mm, 3.3 mm to 5 mm, 3.4 mm to 5 mm, 3.5 mm to 5 mm, 3.6 mm to 5 mm, 3.7 mm to 5 mm, 3.8 mm to 5 mm, 3.9 mm to 5 mm, 4 mm to 5 mm, 4.1 mm to 5 mm, 4.2 mm to 5 mm, 4.3 mm to 5 mm, 4.4 mm to 5 mm, 4.5 mm to 5 mm, 4.6 mm to 5 mm, 4.7 mm to 5 mm, 4.8 mm to 5 mm, 4.9 mm to 5 mm, 100 μm to 4.9 mm, 100 μm to 4.8 mm, 100 μm to 4.7 mm, 100 μm to 4.6 mm, 100 μm to 4.5 mm, 100 μm to 4.4 mm, 100 μm to 4.3 mm, 100 μm to 4.2 mm, 100 μm to 4.1 mm, 100 μm to 4 mm, 100 μm to 3.9 mm, 100 μm to 3.8 mm, 100 μm to 3.7 mm, 100 μm to 3.6 mm, 100 μm to 3.5 mm, 100 μm to 3.4 mm, 100 μm to 3.3 mm, 100 μm to 3.2 mm, 100 μm to 3.1 mm, 100 μm to 3 mm, 100 μm to 2.9 mm, 100 μm to 2.8 mm, 100 μm to 2.7 mm, 100 μm to 2.6 mm, 100 μm to 2.5 mm, 100 μm to 2.4 mm, 100 μm to 2.3 mm, 100 μm to 2.2 mm, 100 μm to 2.1 mm, 100 μm to 2 mm, 100 μm to 1.9 mm, 100 μm to 5 mm, 100 μm to 1.8 mm, 100 μm to 1.7 mm, 100 μm to 1.6 mm, 100 μm to 1.5 mm, 100 μm to 1.4 mm, 100 μm to 1.3 mm, 100 μm to 1.2 mm, 100 μm to 1.1 mm, 100 μm to 1 mm, 100 μm to 900 μm, 100 μm to 800 μm, 100 μm to 700 μm, 100 μm to 600 μm, 100 μm to 500 μm, 100 μm to 400 μm, 100 μm to 300 μm, or 100 μm to 200 μm).

In some embodiments, micro-features may be of varying geometries. A micro-feature may be a hole (e.g., a circular hole or an oval-shaped hole) or a slit. A slit may be a rectangular-shaped slit, a square-shaped slit, a U-shaped slit, or a T-shaped slit. Shapes and dimensions of a micro-feature can be optimized, e.g., to maximize the ability of a hollow needle or hollow staple to capture a portion of skin tissue, while minimizing an impact on mechanical robustness and integrity of a hollow needle or hollow staple. In some embodiments, a micro-feature may be a circular hole having a diameter of from about 10 μm to about 1 mm (e.g., from 10 μm to 1 mm, 10 μm to 900 μm, 10 μm to 880 μm, 10 μm to 860 μm, 10 μm to 840 μm, 10 μm to 820 μm, 10 μm to 800 μm, 10 μm to 780 μm, 10 μm to 760 μm, 10 μm to 740 μm, 10 μm to 720 μm, 10 82 m to 700 μm, 10 μm to 680 μm, 10 μm to 660 μm, 10 μm to 640 μm, 10 μm to 620 μm, 10 μm to 600 μm, 10 μm to 580 μm, 10 μm to 560 μm, 10 μm to 540 μm, 10 μm to 520 μm, 10 μm to 500 μm, 10 μm to 480 μm, 10 μm to 460 μm, 10 μm to 440 μm, 10 μm to 420 μm, 10 μm to 400 μm, 10 μm to 380 μm, 10 μm to 360 μm, 10 μm to 340 μm, 10 μm to 320 μm, 10 μm to 300 μm, 10 μm to 280 μm, 10 μm to 260 μm, 10 μm to 240 μm, 10 μm to 220 μm, 10 μm to 200 μm, 10 μm to 180 μm, 10 μm to 160 μm, 10 μm to 140 μm, 10 μm to 120 μm, 10 μm to 100 μm, 10 μm to 80 μm, 10 μm to 60 μm, 10 μm to 40 μm, 10 μm to 20 μm, 20 μm to 1 mm, 40 μm to 1 mm, 60 μm to 1 mm, 80 μm to 1 mm, 100 μm to 1 mm, 120 μm to 1 mm, 140 μm to 1 mm, 160 μm to 1 mm, 180 μm to 1 mm, 200 μm to 1 mm, 220 μm to 1 mm, 240 μm to 1 mm, 260 μm to 1 mm, 280 μm to 1 mm, 300 μm to 1 mm, 320 μm to 1 mm, 340 μm to 1 mm, 360 μm to 1 mm, 380 μm to 1 mm, 400 μm to 1 mm, 420 μm to 1 mm, 440 μm to 1 mm, 460 μm to 1 mm, 480 μm to 1 mm, 500 μm to 1 mm, 520 μm to 1 mm, 540 μm to 1 mm, 560 μm to 1 mm, 580 μm to 1 mm, 600 μm to 1 mm, 620 μm to 1 mm, 640 μm to 1 mm, 660 μm to 1 mm, 680 μm to 1 mm, 700 μm to 1 mm, 720 μm to 1 mm, 740 μm to 1 mm, 760 μm to 1 mm, 780 μm to 1 mm, 800 μm to 1 mm, 820 μm to 1 mm, 840 μm to 1 mm, 860 μm to 1 mm, 880 µm to 1 mm, 900 µm to 1 mm, 920 µm to 1 mm, 940 µm to 1 mm, 960 µm to 1 mm, or 980 µm to 1 mm).

In some embodiments, a micro-feature may be a slit having a length and a width (e.g., a rectangular-shaped slit, a square-shaped slit, a U-shaped slit, or a T-shaped slit), in which a length or width may be from about 10 µm to about 1 mm (e.g., from 10 µm to 1 mm, 10 µm to 900 µm, 10 µm to 880 µm, 10 µm to 860 µm, 10 µm to 840 µm, 10 µm to 820 µm, 10 µm to 800 µm, 10 µm to 780 µm, 10 µm to 760 µm, 10 µµm to 740 µm, 10 µm to 720 µm, 10 µm to 700 µm, 10 µm to 680 µm, 10 µm to 660 µm, 10 µm to 640 µm, 10 µm to 620 µm, 10 µm to 600 µm, 10 µm to 580 µm, 10 µm to 560 µm, 10 µm to 540 µm, 10 µm to 520 µm, 10 µm to 500 µm, 10 µm to 480 µm, 10 µm to 460 µm, 10 µm to 440 µm, 10 µm to 420 µm, 10 µm to 400 µm, 10 µm to 380 µm, 10 µm to 360 µm, 10 µm to 340 µm, 10 µm to 320 µm, 10 µm to 300 µm, 10 µm to 280 µm, 10 µm to 260 µm, 10 µm to 240 µm, 10 µm to 220 µm, 10 µm to 200 µm, 10 µm to 180 µm, 10 µm to 160 µm, 10 µm to 140 µm, 10 µm to 120 µm, 10 µm to 100 µm, 10 µm to 80 µm, 10 µm to 60 µm, 10 µm to 40 µm, 10 µm to 20 µm, 20 µm to 1 mm, 40 µm to 1 mm, 60 µm to 1 mm, 80 µm to 1 mm, 100 µm to 1 mm, 120 µm to 1 mm, 140 µm to 1 mm, 160 µm to 1 mm, 180 µm to 1 mm, 200 µm to 1 mm, 220 µm to 1 mm, 240 µm to 1 mm, 260 µm to 1 mm, 280 µm to 1 mm, 300 µm to 1 mm, 320 µm to 1 mm, 340 µm to 1 mm, 360 µm to 1 mm, 380 µm to 1 mm, 400 µm to 1 mm, 420 µm to 1 mm, 440 µm to 1 mm, 460 µm to 1 mm, 480 µm to 1 mm, 500 µm to 1 mm, 520 µm to 1 mm, 540 µm to 1 mm, 560 µm to 1 mm, 580 µm to 1 mm, 600 µm to 1 mm, 620 µm to 1 mm, 640 µm to 1 mm, 660 µm to 1 mm, 680 µm to 1 mm, 700 µm to 1 mm, 720 µm to 1 mm, 740 µm to 1 mm, 760 µm to 1 mm, 780 µm to 1 mm, 800 µm to 1 mm, 820 µm to 1 mm, 840 µm to 1 mm, 860 µm to 1 mm, 880 µm to 1 mm, 900 µm to 1 mm, 920 µm to 1 mm, 940 µm to 1 mm, 960 µm to 1 mm, or 980 µm to 1 mm).

In some embodiments, micro-features may be designed and constructed to have a directional effect on a tissue portion captured inside a lumen of a hollow needle or hollow staple. For example, a shape and orientation of a micro-feature may affect a coring force of a hollow needle or hollow staple. For example, a U-shaped slit may create a hook near a tip of a hollow needle or hollow staple, which may help to retain a tissue portion inside a lumen of a hollow needle or hollow staple upon withdrawal of a needle or staple from skin. In some embodiments, a micro-feature can intersect an inner wall of a hollow needle or hollow staple at a sharp edge, which can directionally affect a coring force of a hollow needle or hollow staple, as well as a resistance force applied by a cored tissue portion inside a lumen of a hollow needle or hollow staple. A micro-feature (e.g., a hole or a slit) drilled or micro-machined into a hollow needle or hollow staple may intersect an inner wall of a hollow needle or hollow staple at a perpendicular angle or at a non-perpendicular angle (e.g., an angle of from about 5 degrees to less than about 90 degrees, such as 5 to 85 degrees, 5 to 80 degrees, 5 to 75 degrees, 5 to 70 degrees, 5 to 65 degrees, 5 to 60 degrees, 5 to 55 degrees, 5 to 50 degrees, 5 to 45 degrees, 5 to 40 degrees, 5 to 35 degrees, 5 to 30 degrees, 5 to 25 degrees, 5 to 20 degrees, 5 to 15 degrees, 5 to 10 degrees, 10 to 85 degrees, 15 to 85 degrees, 20 to 85 degrees, 25 to 85 degrees, 30 to 85 degrees, 35 to 85 degrees, 40 to 85 degrees, 45 to 85 degrees, 50 to 85 degrees, 55 to 85 degrees, 60 to 85 degrees, 65 to 85 degrees, 70 to 85 degrees, 75 to 85 degrees, or 80 to 85 degrees). In some embodiments, a hollow needle comprising a tip micro-feature can intersect an inner wall of a hollow needle at a non-perpendicular angle and create a sharp edge. As a tissue portion enters a hollow needle from a needle tip, a tissue portion is traveling in a direction of lower resistance. As a hollow needle is being withdrawn from skin tissue, as well as once a hollow needle is released from skin tissue, a micro-feature can help to retain a tissue portion inside a lumen of a hollow needle and prevent a tissue portion from being released from a hollow needle. In some embodiments, one or more micro-features may be micro-machined into a hollow needle or hollow staple through available processes and techniques, such as laser drilling or wire electrostatic discharge machining (EDM).

Needle and Staple Coating

In some embodiments, technologies, devices and/or methods described herein comprise a needle (e.g., a hollow needle) or staple (e.g., a hollow staple) coated with a material (e.g., a hard material) that improves or maintains the mechanical integrity, durability, and reliability of a needle or staple. A coating material may help to prevent damage, abrasion, and wear and tear of a needle tip and heel during repeated insertions into and withdrawals from skin tissue. Examples of materials (e.g., a hard material) that may be used to coat a needle or staple include, but are not limited to, TiN, TiCN, TiAlN, ZrN, and diamond-like carbon (DLC). A hard material may be applied as a coating to the outside surface of a hollow needle or hollow staple, an inner surface (e.g., the surface of the inner lumen) of a hollow needle or hollow staple, or both surfaces.

Surface of Hollow Needle and Hollow Staple Lumen

In some embodiments, technologies, devices and/or methods described herein comprise a lumen surface of a hollow needle or hollow staple that may affect coring force, coring rate, and/or insertion force of a hollow needle or hollow staple. A lumen of a hollow staple refers to a lumen of one or more legs of a hollow staple. In particular, friction between the lumen surface and a cored tissue portion may determine coring force, coring rate, and/or insertion force. In some embodiments, hollow needles and hollow staples described herein are designed to maximize coring rate and minimize hollow needle and hollow staple insertions that do not result in cored tissue removal. In some embodiments, a tissue portion detaches from skin when coring force (e.g., the force applied by a hollow needle or hollow staple to a cored tissue portion as a needle is being withdrawn from skin) exceeds tissue resistance force, which can be determined by connection of a tissue portion to its surrounding tissue. For example, when a hollow needle is fully inserted through the dermal layer of skin, a tissue resistance force is determined by the connection between a tissue portion in the lumen of a needle and a subcutaneous fat layer. Accordingly, when a coring force exceeds a tissue resistance force, a cored tissue portion is captured in a lumen of a hollow needle and removed from skin. A rough lumen surface can increase friction between a cored tissue portion and a lumen surface, which may result in increased insertion force, increased coring force, and increased coring rate. In some embodiments, lubrication of a lumen surface reduces friction between a cored tissue portion and a lumen surface, which may result in decreased insertion force, decreased coring force, and/or decreased coring rate. An overly rough and uneven lumen surface may lead to high occurrence of needle degradation (e.g., needle heel and tip degradations), may cause difficulty in removing cored tissue portions from a lumen, and/or may cause needle clogging. The degree of roughness of a lumen surface may be optimized to increase coring force and coring rate without compromising durability of a needle, insertion force, ability to remove tissue from a needle lumen, and resistance of a needle to degradation (e.g., needle heel and tip degradation).

In some embodiments, hollow needles or hollow staples may have a coring rate of at least about 5% (e.g., from about 5% to about 100%, such as 5% to 100%, 5% to 95%, 5% to 90%, 5% to 85%, 5% to 80%, 5% to 75%, 5% to 70%, 5% to 65%, 5% to 60%, 5% to 55%, 5% to 50%, 5% to 45%, 5% to 40%, 5% to 35%, 5% to 30%, 5% to 25%, 5% to 20%, 5% to 15%, 5% to 10%, 10% to 95%, 15% to 95%, 20% to 95%, 25% to 95%, 30% to 95%, 35% to 95%, 40% to 95%, 45% to 95%, 50% to 95%, 55% to 95%, 60% to 95%, 65% to 95%, 70% to 95%, 75% to 95%, 80% to 95%, 85% to 95%, or 90% to 95%).

In some embodiments, hollow needles or hollow staples may have a coring force of about 0.01 N to about 30 N (e.g., 0.01, 0.05, 0.1, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 N). In some embodiments, a two-prong hollow needle having a bevel angle α of 20 degrees may have a coring force of about 0.1 N to about 10 N (e.g., 0.5, 1, 1.5, 2, 2.5, 3, 3.5, 4, 4.5, 5, 5.5, 6, 6.5, 7, 7.5, 8, 8.5, 9, 9.5, or 10 N).

In some embodiments, an insertion force or retraction force required by a needle (e.g., a hollow needle) or staple (e.g., a hollow staple) may be between about 1 N and about 30 N (e.g., 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, or 30 N). An insertion or retraction force required by a staple (e.g., a hollow staple) may depend linearly on the number of ends or legs of the staple. In some embodiments, a staple having two ends may require insertion and retraction forces of 14 N and 8 N, respectively (in which each end of the staple requires insertion and retraction forces of 7 N and 4 N), and a staple having three ends may require insertion and retraction forces of 21 N and 12 N, respectively.

In some embodiments, a coating material and/or a lubricant may affect a degree of roughness of a lumen surface, and thus friction between a lumen surface and a cored tissue portion. A lumen surface of a hollow needle or hollow staple may be polished by running a lubricant or a polishing media though a hollow needle or hollow staple to reduce roughness of a lumen surface. Examples of lubricants include, but are not limited to, salt-based lubricants (e.g., buffered saline solutions (e.g., PBS)), sugar-based lubricants (e.g., sucrose and glucose solutions), and surfactant-based lubricants (e.g., solutions containing Tween 20).

Needle and Staple Manufacture

In some embodiments, technologies, devices and/or methods described herein comprise a needle (e.g., a hollow needle) or staple (e.g., a hollow staple) that may be made using available manufacturing techniques and processes. For example, manufacturing of a hollow needle can start with drawing the needle hypodermic tube, followed by forming a needle tip. A needle hypodermic tube may be drawn using manufacturing processes, e.g., single plug, double plug, and sunk. A needle tip may be formed by grinding. For example, a needle (e.g., a hollow needle) having one prong may be formed by grinding one side of a distal end of a needle at an angle relative to a longitudinal axis of a hollow needle. Similarly, a needle (e.g., a hollow needle) having two prongs may be formed by grinding opposite sides of a distal end of a needle at an angle relative to a longitudinal axis of a hollow needle. A grinding process may be performed at a low temperature to prevent or reduce annealing of a needle material and to prevent a needle material from undergoing phase transitions at high temperatures (e.g., at alloy transition temperature, which is defined by alloy stoichiometry). Annealed material may become ductile and more prone to bending, which may reduce the durability and mechanical integrity of a needle (e.g., a hollow needle) or staple (e.g., a hollow staple). Maintaining a low temperature (e.g., a temperature lower than the alloy transition temperature) during the grinding process may be achieved by, e.g., reducing the grinding speed and/or grinding rate and using a cooling fluid (e.g., periodically submerging the needle material and/or the grinding machinery in a cooling fluid). In some embodiments, a cooling fluid used may be at room temperature. Other non-grinding techniques and processes may also be used to manufacture needles (e.g., hollow needles) and/or staples (e.g., hollow staples), e.g., electrical discharge machining.

Actuation, Translation, and Position Detection Mechanisms

In some embodiments, technologies, devices and/or methods described herein may be configured for hand-held, manual operation or connected to an external device for automated operation. In some embodiments, an article, apparatus, or system described herein may be configured for hand-held, manual operation and at the same time, connected to an external device, which may function to provide additional input and/or to charge an article, apparatus, or system during operation. A technology, device and/or method described herein may include one or more actuation mechanisms to drive a needle (e.g., a hollow needle) and/or staple (e.g., a hollow staple), or an article, apparatus, or system comprising a needle and/or staple, into and/or across skin. In some embodiments, an actuation unit may be disposed within an article, apparatus, or system. In some embodiments, an actuation unit may be an external device that can be attached and detached to an article, apparatus, or system. An actuation unit may include x-, y-, and z-actuators. In some embodiments, an actuation unit may include only x- and y-actuators, and a z-actuator (e.g., a voice coil) may be part of an article, apparatus, or system. In some embodiments, "x," "y," and/or "z" actuators may drive a needle and/or staple into and/or across a large area of skin surface in a relatively short amount of time compared to manual deployment of a needle and/or staple. In other embodiments, "x," "y," and/or "z" actuators may drive a needle and/or staple into and/or across a small area of skin surface (e.g., a small area on the face (e.g., an area between the nose and the upper lip)). In other embodiments, "x," "y," and/or "z" actuators may drive a needle or staple into and/or across multiple large and/or small areas of skin surface. Examples of actuators include, but are not limited to, voice coil (VC) actuators, pneumatic or hydraulic actuators, electromagnetic actuators, motors with cams, motors with lead screws (e.g., stepper motors), and piezoelectric actuators.

A "z" actuator may drive penetration into skin by a needle (e.g., a needle) or staple and/or retraction of a needle or staple after insertion. In some embodiments, a z-actuator (e.g., a voice coil) is part of an article, apparatus, or system described herein (e.g., part of a component of an article, apparatus, or system) and may be detachably attached to an article, apparatus, or system. In some embodiments, a z-actuator is a VC actuator.

In some embodiments, technologies, devices and/or methods described herein comprise a feature or setting that has the ability to control or change depth of penetration of a needle (e.g., a hollow needle) and/or staple (e.g., a hollow staple) into skin. In some embodiments, a scroll wheel on a user interface of a base unit may adjust an allowed depth of penetration by a needle and/or staple by physically retracting a needle and/or staple and/or providing an electrical signal to a z-actuator. In some embodiments, digital controls on a user interface of a base unit may control depth and/or timing of penetration into and retraction out of skin by a needle and/or staple. In some embodiments, an operator may program a computer component of a base unit to require a certain displacement of a needle or staple into skin based upon an area being treated. In some embodiments, a needle or staple may be displaced up to about, e.g., 10 mm into thick skin (e.g., on a patient's back or into scar tissue), or about, e.g., 1 mm into thin skin (e.g., on a patient's cheeks), for instance. In some embodiments, a needle and/or staple may be displaced to extend (i) into the dermal layer, (ii) through an entire dermal layer to a junction of a dermal layer and a subcutaneous fat layer, or (iii) into a subcutaneous fat layer.

In some embodiments, a z-actuator may be installed in an applicator or main body of an article, apparatus, or system described herein. A z-actuator may serve as a component in an applicator or main body that functions to push a needle and/or staple into skin tissue. In this configuration, a z-actuator in an applicator or main body may be able to extend forward or retract backward within an applicator or main body. When a z-actuator is extended forward, a needle and/or staple is pushed into skin tissue. For example, a z-actuator may be disposed inside applicator 20 shown in FIGS. 1D and 1E, applicator 45 shown in FIGS. 2A and 2E, applicator 66 shown in FIGS. 3A-3C, and applicator 76 shown in FIGS. 4A and 4B. A z-actuator may also be disposed inside main body 81 shown in FIGS. 5A and 5B, main body 91 shown in FIGS. 6A-6D, main body 114 shown in FIG. 8A.

In some embodiments, an article, apparatus, or system may include an "x" and/or "y" actuator for translating a needle and/or staple, or an article, apparatus, or system comprising a needle and/or staple, across skin. A x/y-actuator may be used to establish skin treatment coverage. In some embodiments, an x/y-actuator may be characterized by a small displacement range (e.g., less than about 10 mm (e.g., 10, 9, 8, 7, 6, 5, 4, 3, 2, and 1 mm)). In some embodiments, an x/y-actuator may be characterized by a relatively large displacement range (e.g., up to about 30 mm). An x/y-actuator may operate with high positional accuracy. In some embodiments, an x/y-actuator may position a needle and/or staple, or an article, apparatus, or system comprising a needle and/or staple, to penetrate skin within a 30 µm radius (e.g., within 30, 25, 20, 15, 10, or 5 µm) of a selected position. In some embodiments, insertions by staples (e.g., hollow staples) may overlap each other such that a distance between two adjacent holes may be smaller than a distance between two legs of a staple (see FIG. 7E). An x/y-actuator may operate with high position accuracy that allows continuous treatment across a treatment area. A treatment area may be a skin area that comprises multiple treatment sites, e.g., a 3 cm by 3 cm treatment area containing nine 1 cm² treatment sites. An x/y-actuator may facilitate movement of a needle and/or staple, or an article, apparatus, or system comprising a needle and/or staple, from one treatment site to an adjacent treatment site within a treatment area. An x/y-actuator may also facilitate movement of a needle and/or staple, or an article, apparatus, or system containing a needle and/or staple, within a treatment site. An x/y-actuator may operate with high position accuracy that avoid gaps between adjacent treatment sites in a treatment area and/or avoid overlaps between adjacent treatment sites in a treatment area.

In some embodiments, an x/y-actuator may be an external device that can be coupled to a guide rail or a template of an article, apparatus, or system described herein. An x/y-actuator may function to translate a guide rail or template across the skin. For example, an x/y-actuator may be coupled to template 42 shown in FIGS. 2B and 2C, guide rail 82 shown in FIG. 5A, and guide rail 92 shown in FIG. 6A.

In any of the technologies, devices, methods, articles, apparatuses, and/or systems described herein, one or more components may be selected or designed to secure one or more of needles (e.g., hollow needles) and/or staples (e.g., hollow staples) and/or prevent or minimize angular movement (e.g., wobbling) of needles and/or staples. In some embodiments, an x-, y-, and/or z-actuator may be capable of operating without causing any significant angular movement (e.g., wobbling) of needles and/or staples. Needles and/or staples may be secured so as to minimize or reduce angular movement of needles and/or staples during insertion to less than 5 degrees, e.g., less than 4, 3, or 2 degrees. An angular movement of needles and/or staples during insertion of ~1-1.5 degrees is within nominal tolerances, whereas an angular movement of needles and/or staples during insertion of ~4-5 degrees or more is to be avoided, if possible. In some embodiments, components that join needles and/or staples to other components of a technology, device, method, article, apparatus, and/or system may be designed with low mechanical tolerances to firmly secure needles and/or staples. This may reduce the prevalence of or lower the risk of destabilization and/or reduction in the structural integrity of needles and/or staples that may result from repeated use. In some embodiments, firmly securing needles and/or staples may prevent and/or minimize dulling, bending, and curling of needle or staple tips that could reduce the effectiveness of needles or staples. Firmly securing needles and/or staples may also reduce the risk of over-striking (e.g., striking a hole produced by a needle or staple more than once).

In some embodiments, z-, x-, and/or y-actuators may be activated independently or together by one or more buttons, keys, toggles, switches, screws, dials, cursors, spin-wheels, or other components. In some embodiments, each z-, x-, and/or y-actuator can be separately controlled (e.g., using separate activation components, such as a button, or by using separate controls in a user interface).

In some embodiments, a technology, device, method, described herein may also include a position detection mechanism, such as an optical tracking mechanism. In some embodiments, a position detection mechanism may be installed within an article, apparatus, or system. In some embodiments, a position detection system may be attached and detached to an article, apparatus, or system. A position detection mechanism (e.g., a camera, infrared sensor, photodiode, and/or LED and/or detector) may assist in tracking movement of an article, apparatus, or system in relation to a template, a patient, or a treatment area. An optical tracking mechanism may also facilitate placement of a needle (e.g., a hollow needle) or staple (e.g., a hollow staple) on a skin surface in an instance of manual translation of an article, apparatus, or system across skin. Control electronics for a position detection mechanism may be disposed within an article, apparatus, or system or external to an article, apparatus, or system, e.g., in a base unit or separate computer. In some embodiments, a position detection mechanism may monitor a distance between a previous needle insertion and a current apparatus position and send a signal to control electronics to actuate a skin penetration mechanism when an apparatus has reached a desired position (e.g., a position a defined distance from a position where a needle or needles were last inserted). Desired distances and/or positions may be controlled at a user interface. Alternatively, apparatuses and systems described herein may be able to detect treated areas and/or positions of already generated holes on skin surface to prevent overlap of treatment areas and to facilitate alignment of new treatment areas.

Figure 10:
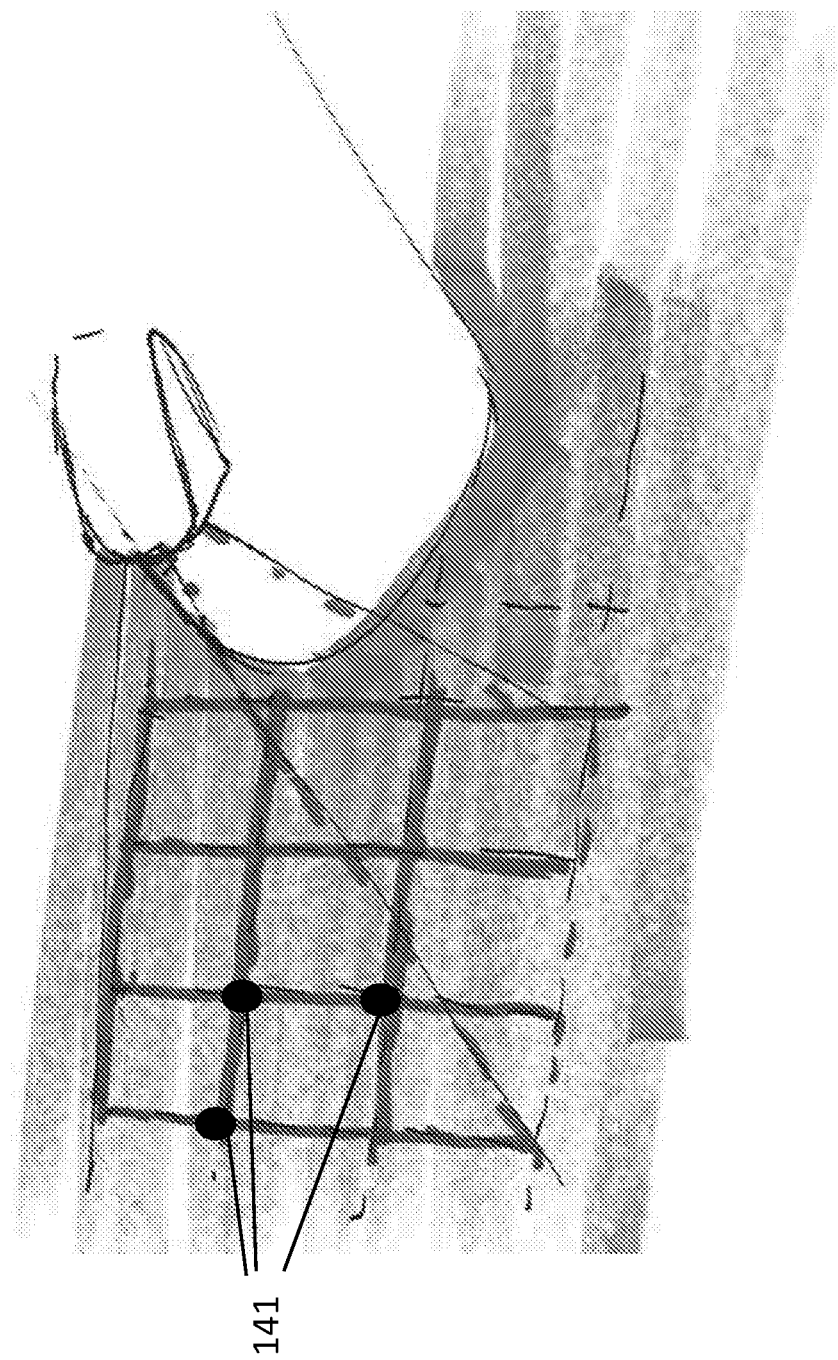
FIG. 10 is a drawing showing a grid pattern projected on the skin tissue by a device (e.g., a laser device).

In some embodiments, a guide rail or template may be used to facilitate positioning of a needle (e.g., a hollow needle) and/or staple (e.g., a hollow staple). A guide rail or template may comprise one or more holes or openings that provide a pre-set pattern (described further herein) for a needle or staple to follow. A guide rail or template may be used alone or in combination with a position detection mechanism and/or an x/y actuator. For example, FIGS. 2A-2D, 3A-3C, 4A, 4B, 5A, 5B, and 6A-6D illustrate different systems including templates or guide rails. As shown in FIGS. 2A-2D, template 42 includes multiple rows, wherein each row contains openings 44 that mark positions for needle insertion. The systems shown in FIGS. 5A, 5B, and 6A-6D provide guide rails (e.g., guide rail 82 or 92) for a main body containing a needle to follow. The guide rails are designed to have a raised backbone or a trough configured for a main body to follow. In other embodiments, a device may project a grid pattern on the skin tissue using light (e.g., a laser device; see FIG. 10). A projected grid pattern may serve as a guide rail or template for a needle or staple to follow.

Position Sensors

In some embodiments, technologies, devices and/or methods described herein comprise apparatuses and systems that may include a position sensor that detects positions at which to insert needle(s) and/or staple(s) into skin tissue. A position sensor may provide signals to other components of an apparatus or system regarding a position for needle or staple insertion. As shown in FIGS. 5A, 5B, and 6B-6D, a position sensor may detect a physical change in a guide rail, e.g., an indentation or groove. In some embodiments, a position sensor may detect a grid drawn or projected onto skin surface. For example, a colored grid may be drawn on the skin surface to serve as a guide rail or template for an apparatus to follow. A position sensor may detect changes in color pigments on skin surface (see FIG. 10), e.g., dark spots 141 may indicate positions for needle or staple insertion. In some embodiments, a position sensor may include a UV light source (e.g., UV light 151 in FIG. 11), which may be used to illuminate positions drawn on skin using a UV-sensitive material (e.g., UV-sensitive material 152).

Arrays of Needles or Staples and Patterns Generated Therefrom

In some embodiments, technologies, devices and/or methods described herein comprise one or more of needles (e.g., hollow needles) or staples (e.g., hollow staples) that may be assembled to form an array, which can refer to a collection of multiple needles and/or staples. An array of needles and/or staples may have any specific size or shape that is configured to fit a skin area to be treated. In some embodiments, a ring shaped array of needles and/or staples may be used for treatment of a skin area around an eye. When using hollow needles and/or hollow staples, a pattern of holes may be formed upon removal of portions of skin tissue. A pattern may include any geometric shape. Spacing between needles and/or staples may exhibit any spacing variation (e.g., a spacing pattern and/or spacing gradient). A pattern may include holes in one or more rows or in a semi-random spatial distribution. Size and geometry of a pattern may be generated based on an area of skin and condition being treated. In some embodiments, a small pattern may be generated for treatment of a peri-oral area, while a large pattern may be suitable for treatment of an abdomen. A pattern may be generated using different numbers and/or arrangements of a plurality of needles (e.g., hollow needles) an/or staples (e.g., hollow staples). A pattern may also be generated using one needle and/or staple, which can undergo multiple actuation cycles and be translated across a surface of a skin region by an x-actuator and/or y-actuator to generate a pattern. In some embodiments, some or all needles and/or staples can be deployed in a temporal pattern. In some embodiments, some or all needles and/or staples are deployed at the same time. In some embodiments, some or all needles and/or staples are deployed in sequence. In some embodiments, one or more needles and/or staples are deployed in a temporal pattern (e.g., slow, fast, at increasing or decreasing speed, at the same time). In some embodiments, a time interval between deployment of a first needle and/or staple and a second needle and/or staple is about 1 ms, 2 ms, 3 ms, 4 ms, 5 ms, 6, ms, 7 ms, 8 ms, 9 ms, 10 ms, 20 ms, 30 ms, 40 ms, 50 ms, 60, ms, 70 ms, 80 ms, 90 ms, 100 ms, 200 ms, 300 ms, 400 ms, 500 ms, 600, ms, 700 ms, 800 ms, 900 ms, or 1000 ms. Without wishing to be bound by theory, needles and/or staples can be deployed in a pattern to control pain and/or bleeding, modify procedure time, and/or for ease of manufacture.

In some embodiments, a pattern may be generated using a plurality of needles (e.g., hollow needles) and/or staples (e.g., hollow staples), which can undergo one or more actuation cycles to generate a pattern. A number of actuation cycles needed to generate a pattern of holes in skin tissue is determined by a size of a pattern, a gauge or inner diameter of a hollow needle or hollow staple, a number of hollow needles and/or hollow staples, and an amount of skin tissue to be removed, e.g., an areal fraction of skin tissue removed. An "areal fraction" of tissue removed refers to a fraction of skin tissue surface covered by holes generated by hollow needle(s) and/or hollow staple(s). In other words, an areal fraction of tissue removed refers to a ratio of an area covered by a total amount of cored tissue portions to a total skin treatment area. In one embodiment, one or more hollow needles and/or hollow staples may be configured to remove an areal fraction of about 0.01 to about 0.65 (e.g., 0.01, 0.02, 0.03, 0.04, 0.05, 0.10, 0.15, 0.20, 0.25, 0.30, 0.35, 0.40, 0.45, 0.50, 0.55, 0.60, or 0.65) of tissue within a treatment area. In another embodiment, one or more hollow needles and/or hollow staples may be configured to remove an areal fraction of less than about 0.1, such as about 0.01 to about 0.05 (e.g., 0.01, 0.015, 0.02, 0.025, 0.03, 0.035, 0.04, 0.045, or 0.05) of tissue within a treatment area. In another embodiment, one or more hollow needles and/or hollow staples may be configured to remove an areal fraction of about 0.02 to about 0.03 (e.g., 0.02, 0.021, 0.022, 0.023, 0.024, 0.025, 0.026, 0.027, 0.028, 0.029, or 0.03, e.g., 0.025) of tissue within a treatment area. In some embodiments, an areal fraction of about 0.01 to about 0.65 (e.g., 0.01, 0.02, 0.03, 0.04, 0.05, 0.10, 0.15, 0.20, 0.25, 0.30, 0.35, 0.40, 0.45, 0.50, 0.55, 0.60, or 0.65) of tissue may be removed within a treatment area for wrinkle reduction. In some embodiments, an areal fraction of about 0.02 to about 0.03 (e.g., 0.02, 0.021, 0.022, 0.023, 0.024, 0.025, 0.026, 0.027, 0.028, 0.029, or 0.03, e.g., 0.025) of tissue may be removed within a treatment area for wrinkle reduction. In some embodiments, an article, apparatus, or system described herein may be configured for detachable attachment to one or more of needles (e.g., hollow needles) and/or staples (e.g., hollow staples) having the same or different configurations. In some embodiments, technologies, devices and/or methods described herein may comprise as few as 1 or as many as hundreds of needles or staples. In some embodiments, 1-10,000 needles or staples may be present (e.g., 1-10, 1-20, 1-30, 1-40, 1-50, 1-60, 1-70, 1-80, 1-90, 1-100, 1-200, 1-300, 1-400, 1-500, 1-600, 1-700, 1-800, 1-900, 1-1,000, 1-1,100, 1-1,200, 1-1,300, 1-1,400, 1-1,500, 1-1,600, 1-1,700, 1-1,800, 1-1,900, 1-2,000, 1-2,200, 1-2,400, 1-2,600, 1-2,800, 1-3,000, 1-3,200, 1-3,400, 1-3,600, 1-3,800, 1-4,000, 1-4,200, 1-4,400, 1-4,600, 1-4,800, 1-5,000, 1-5,200, 1-5,400, 1-5,600, 1-5,800, 1-6,000, 1-6,200, 1-6,400, 1-6,600, 1-6,800, 1-7,000, 1-7,200, 1-7,400, 1-7,600, 1-7,800, 1-8,000, 1-8,200, 1-8,400, 1-8,600, 1-8,800, 1-9,000, 1-9,200, 1-9,400, 1-9,600, 1-9,800, or 1-10,000 needles or staples). The use of an array of a plurality of needles (e.g., hollow needles) and/or staples (e.g., hollow staples) to generate a pattern may facilitate skin treatment over larger areas and in less time.

In some embodiments, a minimum distance between two needles (e.g., hollow needles) in an array of needles may be between about 0.1 mm to about 50 mm (e.g., from 0.1 mm to 0.2 mm, 0.1 mm to 0.5 mm, 0.1 mm to 1 mm, 0.1 mm to 2 mm, 0.1 mm to 5 mm, 0.1 mm to 10 mm, 0.1 mm to 15 mm, 0.1 mm to 20 mm, 0.1 mm to 30 mm, 0.1 mm to 40 mm, 0.1 mm to 50 mm, 0.2 mm to 0.5 mm, 0.2 mm to 1 mm, 0.2 mm to 2 mm, 0.2 mm to 5 mm, 0.2 mm to 10 mm, 0.2 mm to 15 mm, 0.2 mm to 20 mm, 0.2 mm to 30 mm, 0.2 mm to 40 mm, 0.2 mm to 50 mm, 0.5 mm to 1 mm, 0.5 mm to 2 mm, 0.5 mm to 5 mm, 0.5 mm to 10 mm, 0.5 mm to 15 mm, 0.5 mm to 20 mm, 0.5 mm to 30 mm, 0.5 mm to 40 mm, 0.5 mm to 50 mm, 1 mm to 2 mm, 1 mm to 5 mm, 1 mm to 10 mm, 1 mm to 15 mm, 1 mm to 20 mm, 1 mm to 30 mm, 1 mm to 40 mm, 1 mm to 50 mm, 2 mm to 5 mm, 2 mm to 10 mm, 2 mm to 15 mm, 2 mm to 20 mm, 2 mm to 30 mm, 2 mm to 40 mm, 2 mm to 50 mm, 5 mm to 10 mm, 5 mm to 15 mm, 5 mm to 20 mm, 5 mm to 30 mm, 5 mm to 40 mm, 5 mm to 50 mm, 10 mm to 15 mm, 10 mm to 20 mm, 10 mm to 30 mm, 10 mm to 40 mm, 10 mm to 50 mm, 15 mm to 20 mm, 15 mm to 30 mm, 15 mm to 40 mm, 15 mm to 50 mm, 20 mm to 30 mm, 20 mm to 40 mm, 20 mm to 50 mm, 30 mm to 40 mm, 30 mm to 50 mm, or 40 mm to 50 mm). In some embodiments, a distance between two needles (e.g., hollow needles) in an array of needles is less than about 15 mm. A minimum distance may correspond to the minimal size of a pattern, while a maximum distance may correspond to the maximum size of a pattern.

In some embodiments, a minimum distance between two legs of a staple (e.g., a hollow staple) may be between about 0.1 mm and about 3 mm (e.g., 0.1, 0.2, 0.4, 0.6, 0.8, 1, 1.2, 1.4, 1.6, 1.8, 2, 2.2, 2.4, 2.6, 2.8, or 3 mm). In some embodiments, holes in skin tissue generated by one or more hollow staples may overlap each other such that a distance between adjacent holes may be smaller than a distance between two legs of a hollow staple (see, e.g., FIG. 7E).

In some embodiments, patterns of different sizes and geometries may be generated based on an area of treatment and/or skin condition being treated. Patterns may also be generated for compatibility with actuation mechanisms and control electronics of a given article, apparatus, or system. Alternatively, actuation mechanisms and control electronics of a technology, device, and/or method as described herein may be selected for compatibility with a desired pattern size and/or geometry. In some embodiments, a long, linear pattern may be generated using a translating mechanism with driving wheels, while a large, rectangular array may be generated using an x- and/or y-actuator to drive hollow needle(s) and/or hollow staple(s) across skin.

In some embodiments, technologies, devices and/or methods described herein comprise one or more hollow needles or hollow staples that may be configured to provide from about 10 to about 10000 cored tissue portions or more per $cm^2$ area (e.g., 10 to 50, 10 to 100, 10 to 200, 10 to 300, 10 to 400, 10 to 500, 10 to 600, 10 to 700, 10 to 800, 10 to 900, 10 to 1000, 10 to 2000, 10 to 4000, 10 to 6000, 10 to 8000, 10 to 10000, 50 to 100, 50 to 200, 50 to 300, 50 to 400, 50 to 500, 50 to 600, 50 to 700, 50 to 800, 50 to 900, 50 to 1000, 50 to 2000, 50 to 4000, 510 to 6000, 50 to 8000, 50 to 10000, 100 to 200, 100 to 300, 100 to 400, 100 to 500, 100 to 600, 100 to 700, 100 to 800, 100 to 900, 100 to 1000, 100 to 2000, 100 to 4000, 100 to 6000, 100 to 8000, 100 to 10000, 200 to 300, 200 to 400, 200 to 500, 200 to 600, 200 to 700, 200 to 800, 200 to 900, 200 to 1000, 200 to 2000, 200 to 4000, 200 to 6000, 200 to 8000, 200 to 10000, 300 to 400, 300 to 500, 300 to 600, 300 to 700, 300 to 800, 300 to 900, 300 to 1000, 300 to 2000, 300 to 4000, 300 to 6000, 300 to 8000, 300 to 10000, 400 to 500, 400 to 600, 400 to 700, 400 to 800, 400 to 900, 400 to 1000, 400 to 2000, 400 to 4000, 400 to 6000, 400 to 8000, 400 to 10000, 500 to 600, 500 to 700, 500 to 800, 500 to 900, 500 to 1000, 500 to 2000, 500 to 4000, 500 to 6000, 500 to 8000, 500 to 10000, 600 to 700, 600 to 800, 600 to 900, 600 to 1000, 600 to 2000, 600 to 4000, 600 to 6000, 600 to 8000, 600 to 10000, 700 to 800, 700 to 900, 700 to 1000, 700 to 2000, 700 to 4000, 700 to 6000, 700 to 8000, 700 to 10000, 800 to 900, 800 to 1000, 800 to 2000, 800 to 4000, 800 to 6000, 800 to 8000, 800 to 10000, 900 to 1000, 900 to 2000, 900 to 4000, 900 to 6000, 900 to 8000, 900 to 10000, 1000 to 2000, 1000 to 4000, 1000 to 6000, 1000 to 8000, 1000 to 10000, 2000 to 4000, 2000 to 6000, 2000 to 8000, 2000 to 10000, 4000 to 6000, 4000 to 8000, 4000 to 10000, 6000 to 8000, 6000 to 10000, or 8000 to 10000 tissue portions per $cm^2$ area) of a skin region to which a technology, device and/or method described herein is applied (e.g., the treatment area).

Base Unit and User Interface

In some embodiments, technologies, devices and/or methods described herein comprise an article, apparatus, or system that may be in communication with a base unit, which may include, e.g., a user interface, a power supply, control electronics, a vacuum pump, and/or other components. A base unit may feature a computer, which may be programmed to operate and/or control any or all aspects of a technology, device, and/or method as described herein.

In some embodiments, a user interface in a base unit may include buttons, keys, switches, toggles, spin-wheels, screens, touch screens, keyboards, cursors, dials, indicators, displays, and/or other components. A user interface may be configured to indicate proper couplings and attachments of components to form an article, apparatus, or system, charged and/or powered status of an article, apparatus, or system, a mode and/or position of needle(s) or staple(s), actuation of components, and/or other useful indication. A user interface may be configured to provide information about number and/or kind of needle(s) and/or staple(s), treatment area, treatment coverage (e.g., areal fraction of skin surface area removed), arrangement of the needle(s) or staple(s), potential depth of penetration by needle(s) and/or staple(s), use count of the needle(s) and/or staple(s), and/or other useful information. A user interface may also be configured to transmit and/or receive information from another unit. For example, user actions at a user interface on an apparatus may be reflected by a user interface of a base unit, or vice versa.

In some embodiments, a base unit may further include electronics to control operation of an apparatus, pressure generating source, and/or other components couple to an apparatus. In some embodiments, a base unit may include one or more microcontrollers, programmable logic, discrete elements, and/or other components. A base unit may further have one or more power supplies. Power supplies may include batteries, alternators, generators, and/or other components. A base unit may be configured to allow conversion of main power to DC for system operation, for example. In some embodiments, a base unit has a battery charging station for use with a battery-powered apparatus (e.g., a main body of a device or system described herein).

In some embodiments, a base unit may be external and/or coupled to a main body (e.g., main body 82 or 92) of a system as described herein. In this exemplary configuration, a base unit may provide indications that, e.g., a needle (e.g., a hollow needle) is properly installed in a main body, a main body is properly coupled to a guide rail, a system is charged or otherwise powered (e.g., an amount of battery life remaining), a needle is in a protracted or retracted position, a fill level of a trap for collecting cored tissue portions, and/or other useful information.

Additional Components

In some embodiments, technologies, devices and/or methods described herein comprise one or more additional components, such as a camera and/or viewing station that may be coupled to an article, apparatus, or system described herein. In some embodiments, a camera may be used to image a treatment area before, during, or after treatment. In some embodiments, a camera may be disposed in or on an apparatus. A camera may transmit signal to a viewing station, such as a computer, that may be disposed in the line of sight of a device operator. An image or images transmitted by a camera to a viewing station (e.g., a computer) may be processed by a visualization software. A visualization software may be capable of calculating a hole density within a treatment area (e.g., a number of holes generated per unit area). An image or images transmitted by a camera to a viewing station (e.g., a computer) may assist an operator in treating skin. In some embodiments, a fluid system may be coupled to an apparatus to facilitate cleaning of skin, e.g., with saline or a sterilizing solution.

In some embodiments, devices (e.g., needles (e.g., hollow needles), staples (e.g., hollow staples), articles, apparatuses, and systems), kits, and methods described herein may be used in combination with a medical record system, e.g., a Computerized Patient Record System (CPRS), and/or a graphic user interface (GUI). A graphic user interface may provide information regarding various parameters of a treatment site of the patient, such as size of a pattern and number of holes to be selected in each treatment site.

In some embodiments, a camera and/or viewing station may also be used for planning a treatment. In some embodiments, an image of a target anatomical area may be taken by a camera and transmitted to a viewing station. A user may select treatment areas (different areas may require different coverage). A viewing station may allow visualization of a simulated treatment outcome that may be predicted using, e.g., certain algorithms that can take into account, for example, effects of skin tightening at parameters selected by a user. Parameters are adjusted by a user until a predicted outcome is optimized. Parameters are then transmitted to a device for treatment of a target area.

In some embodiments, a thermal device, e.g., a cooling device and/or system may be used to cool skin prior, during, and/or after a coring procedure, e.g., to achieve an analgesic effect, and/or to control bleeding through vasoconstriction of blood vessels at or near a treatment site.

In some embodiments, a system or device comprises a window, e.g., a part of a system or device that is, e.g., open, transparent, and/or translucent. In some embodiments, a window allows a user to view, e.g., unaided, a treatment area before, during, and/or after treatment, Materials In some embodiments, technologies, devices and/or methods described herein may comprise or may be manufactured using any useful material. In some embodiments, a component of an article, apparatus, or system may include and/or be formed from any useful polymer or plastic. Such materials may include alginate, benzyl hyaluronate, carboxymethylcellulose, cellulose acetate, chitosan, collagen, dextran, epoxy, gelatin, hyaluronic acid, hydrocolloids, nylon (e.g., nylon 6 or PA6), pectin, poly (3-hydroxyl butyrate-co-poly (3-hydroxyl valerate), polyalkanes, polyalkene, polyalkynes, polyacrylate (PA), polyacrylonitrile (PAN), polybenzimidazole (PBI), polycarbonate (PC), polycaprolactone (PCL), polyester (PE), polyethylene glycol (PEG), polyethylene oxide (PEO), PEO/polycarbonate/polyurethane (PEO/PC/PU), poly(ethylene-co-vinyl acetate) (PEVA), PEVA/polylactic acid (PEVA/PLA), polyethylene, polypropylene, poly (ethylene terephthalate) (PET), PET/poly (ethylene naphthalate) (PET/PEN) polyglactin, polyglycolic acid (PGA), polyglycolic acid/polylactic acid (PGA/PLA), polyimide (PI), polylactic acid (PLA), poly-L-lactide (PLLA), PLLA/PC/polyvinylcarbazole (PLLA/PC/PVCB), poly (β-malic acid)-copolymers (PMLA), polymethacrylate (PMA), poly (methyl methacrylate) (PMMA), polystyrene (PS), polyurethane (PU), poly (vinyl alcohol) (PVA), polyvinylcarbazole (PVCB), polyvinyl chloride (PVC), polyvinylidenedifluoride (PVDF), polyvinylpyrrolidone (PVP), silicone, rayon, polytetrafluoroethylene (PTFE), polyether ether ketone (PEEK), or combinations thereof. Polymers and/or plastics of technologies, devices and/or methods described herein may be composite materials in which additives to polymers and/or plastics, such as ceramics or particles, alter mechanical properties.

In some embodiments, components of an article, apparatus, technology, device, or system may include and/or be formed from any useful metal or metal alloy. In some embodiments, a needle (e.g., a hollow needle) or staple (e.g., a hollow staple) may be a metallic needle or staple. Metals and alloys featured in technologies, devices and/or methods described herein can include stainless steel; titanium; a nickel-titanium (NiTi) alloy; a nickel-titanium-niobium (NiTiNb) alloy; a nickel-iron-gallium (NiFeGa) alloy; a nickel-manganese-gallium (NiMnGa) alloy; a copper-aluminum-nickel (CuAlNi) allow; a copper-zinc (CuZn) alloy; a copper-tin (CuSn) alloy; a copper-zinc-aluminum (CuZnAl) alloy; a copper-zinc-silicon (CuZnSi) alloy; a copper-zinc-tin (CuZnSn) alloy; a copper-manganese alloy; a gold-cadmium (AuCd) alloy; a silver-cadmium (AgCd) alloy; an iron-platinum (FePt) alloy; an iron-manganese-silicon (FeMnSi) alloy; a cobalt-nickel-aluminum (CoNiAl) alloy; a cobalt-nickel-gallium (CoNiGa) alloy; or a titanium-palladium (TiPd) alloy. In some embodiments, components of an article, apparatus, technology, device, or system may also include and/or be formed from glass. In some embodiments, an apparatus may include one or more glass needles (e.g., hollow needles).

In some embodiments, technologies, devices (e.g., needles (e.g., hollow needles), staples (e.g., hollow staples), articles, apparatuses, and systems), methods and/or kits described herein may comprise one or more adhesives. An adhesive may be located on a surface, between components, or otherwise adhered to a component. For example, first layer 12 of article 10 illustrated in FIG. 1A may be covered with an adhesive material. Templates illustrated in FIGS. 2A-2D and 3A-3C and guide rails illustrated in FIGS. 5A, 5B, and 6A-6D may also be coated with an adhesive on a surface of a template or guide rail that contacts skin tissue. Useful adhesives include a biocompatible matrix (e.g., those including at least one of collagen (e.g., a collagen sponge), low melting agarose (LMA), polylactic acid (PLA), and/or hyaluronic acid (e.g., hyaluranon); a photosensitizer (e.g., Rose Bengal, riboflavin-5-phosphate (R-5-P), methylene blue (MB), N-hydroxypyridine-2-(1 H)-thione (N-HTP), a porphyrin, or a chlorin, as well as precursors thereof); a photochemical agent (e.g., 1,8 naphthalimide); a synthetic glue (e.g., a cyanoacrylate adhesive, a polyethylene glycol adhesive, or a gelatin-resorcinol-formaldehyde adhesive); a biologic sealant (e.g., a mixture of riboflavin-5-phosphate and fibrinogen, a fibrin-based sealant, an albumin-based sealant, or a starch-based sealant); or a hook or loop and eye system (e.g., as used for Velcro®). In some embodiments, an adhesive is biodegradable.

In some embodiments, an adhesive may be a pressure-sensitive adhesive (PSA). Properties of pressure sensitive adhesives are governed by three parameters: tack (initial adhesion), peel strength (adhesion), and shear strength (cohesion). Pressure-sensitive adhesives can be synthesized in several ways, including solvent-borne, water-borne, and hot-melt methods. Tack is initial adhesion under slight pressure and short dwell time, and depends on an adhesive's ability to wet a contact surface. Peel strength is force required to remove a PSA from a contact surface. Peel adhesion depends on many factors, including tack, bonding history (e.g. force, dwell time), and adhesive composition. Shear strength is a measure of an adhesive's resistance to continuous stress. Shear strength is influenced by several parameters, including internal adhesion, cross-linking, and viscoelastic properties of an adhesive. Permanent adhesives are generally resistant to debonding and possess very high peel and shear strength. Pressure-sensitive adhesives may include natural rubber, synthetic rubber (e.g., styrene-butadiene and styrene-ethylene copolymers), polyvinyl ether, polyurethane, acrylic, silicones, and ethylene-vinyl acetate copolymers. A copolymer's adhesive properties can be altered by varying the composition (via monomer components) changing the glass transition temperature (Tg) or degree of cross-linking. In general, a copolymer with a lower Tg is less rigid and a copolymer with a higher Tg is more rigid. Tack of PSAs can be altered by addition of components to alter the viscosity or mechanical properties. Pressure sensitive adhesives are further described in Czech et al., "Pressure-Sensitive Adhesives for Medical Applications," in Wide Spectra of Quality Control, Dr. Isin Akyar (Ed., published by InTech), Chapter 17 (2011), which is hereby incorporated by reference in its entirety.

In some embodiments, devices and/or methods described herein comprise or are configured to deliver one or more useful therapeutic agents. In some embodiments, needles or staples, e.g., hollow needles or hollow staples, may be configured to administer one or more therapeutic agents to skin. Needles or staples, e.g., hollow needles or hollow staples may be capable of creating direct channels or holes to local blood supply and/or local perfusion by removing cored tissue portions. Direct channels or holes may be used to deliver useful therapeutic agents. Depending on size (e.g., diameter and/or active length) of hollow needles or hollow staples, holes having different diameters and/or penetration depths may be created. In some embodiments, hollow needles having a large diameter (e.g., 18 gauge) and/or a long active length may be used to create large and deep holes that may be used as delivery channels to deliver a large volume dose of therapeutic agents. In some embodiments, the holes may be plugged. In some embodiments, holes may be covered with a dressing (e.g., a compressive or occlusive dressing) and/or a closure (e.g., bandage, hemostats, sutures, or adhesives) to prevent delivered therapeutic agents from leaking out of skin and/or to maintain moisture of a treated skin area. Delivery of useful therapeutic agents through holes created by hollow needles or hollow staples may provide precise control of dosing of therapeutic agents.

Examples of useful therapeutic agents include one or more growth factors (e.g., vascular endothelial growth factor (VEGF), platelet-derived growth factor (PDGF), transforming growth factor beta (TGF-β), fibroblast growth factor (FGF), epidermal growth factor (EGF), and keratinocyte growth factor); one or more stem cells (e.g., adipose tissue-derived stem cells and/or bone marrow-derived mesenchymal stem cells); one or more skin whitening agents (e.g., hydroquinone); one or more vitamin A derivatives (e.g., tretinoin), one or more analgesics (e.g., paracetamol/acetaminophen, aspirin, a non-steroidal antiinflammatory drug, as described herein, a cyclooxygenase-2-specific inhibitor, as described herein, dextropropoxyphene, co-codamol, an opioid (e.g., morphine, codeine, oxycodone, hydrocodone, dihydromorphine, pethidine, buprenorphine, tramadol, or methadone), fentanyl, procaine, lidocaine, tetracaine, dibucaine, benzocaine, p-butylaminobenzoic acid 2-(diethylamino) ethyl ester HCl, mepivacaine, piperocaine, dyclonine, or venlafaxine); one or more antibiotics (e.g., cephalosporin, bactitracin, polymyxin B sulfate, neomycin, bismuth tribromophenate, or polysporin); one or more antifungals (e.g., nystatin); one or more antiinflammatory agents (e.g., a non-steroidal antiinflammatory drug (NSAID, e.g., ibuprofen, ketoprofen, flurbiprofen, piroxicam, indomethacin, diclofenac, sulindac, naproxen, aspirin, ketorolac, or tacrolimus), a cyclooxygenase-2-specific inhibitor (COX-2 inhibitor, e.g., rofecoxib (Vioxx®), etoricoxib, and celecoxib (Celebrex®)), a glucocorticoid agent, a specific cytokine directed at T lymphocyte function), a steroid (e.g., a corticosteroid, such as a glucocorticoid (e.g., aldosterone, beclometasone, betamethasone, cortisone, deoxycorticosterone acetate, dexamethasone, fludrocortisone acetate, hydrocortisone, methylprednisolone, prednisone, prednisolone, or triamcinolone) or a mineralocorticoid agent (e.g., aldosterone, corticosterone, or deoxycorticosterone)), or an immune selective antiinflammatory derivative (e.g., phenylalanine-glutamine-glycine (FEG) and its D-isomeric form (feG))); one or more antimicrobials (e.g., chlorhexidine gluconate, iodine (e.g., tincture of iodine, povidone-iodine, or Lugol's iodine), or silver, such as silver nitrate (e.g., as a 0.5% solution), silver sulfadiazine (e.g., as a cream), or $Ag^+$ in one or more useful carriers (e.g., an alginate, such as Acticoat® including nanocrystalline silver coating in high density polyethylene, available from Smith & Nephew, London, U.K., or Silvercel® including a mixture of alginate, carboxymethylcellulose, and silver coated nylon fibers, available from Systagenix, Gatwick, U.K.; a foam (e.g., Contreet® Foam including a soft hydrophilic polyurethane foam and silver, available from Coloplast A/S, Humlebk, Denmark); a hydrocolloid (e.g., Aquacel® Ag including ionic silver and a hydrocolloid, available from Conva Tec Inc., Skillman, N.J.); or a hydrogel (e.g., Silvasorb® including ionic silver, available from Medline Industries Inc., Mansfield, Mass.)); one or more antiseptics (e.g., an alcohol, such as ethanol (e.g., 60-90%), 1-propanol (e.g., 60-70%), as well as mixtures of 2-propanol/isopropanol; boric acid; calcium hypochlorite; hydrogen peroxide; manuka honey and/or methylglyoxal; a phenol (carbolic acid) compound, e.g., sodium 3,5-dibromo-4-hydroxybenzene sulfonate, trichlorophenylmethyl iodosalicyl, or triclosan; a polyhexanide compound, e.g., polyhexamethylene biguanide (PHMB); a quaternary ammonium compound, such as benzalkonium chloride (BAC), benzethonium chloride (BZT), cetyl trimethylammonium bromide (CTMB), cetylpyridinium chloride (CPC), chlorhexidine (e.g., chlorhexidine gluconate), or octenidine (e.g., octenidine dihydrochloride); sodium bicarbonate; sodium chloride; sodium hypochlorite (e.g., optionally in combination with boric acid in Dakin's solution); or a triarylmethane dye (e.g., Brilliant Green)); one or more antiproliferative agents (e.g., sirolimus, tacrolimus, zotarolimus, biolimus, or paclitaxel); one or more emollients; one or more hemostatic agents (e.g., collagen, such as microfibrillar collagen, chitosan, calcium-loaded zeolite, cellulose, anhydrous aluminum sulfate, silver nitrate, potassium alum, titanium oxide, fibrinogen, epinephrine, calcium alginate, poly-N-acetyl glucosamine, thrombin, coagulation factor(s) (e.g., II, V, VII, VIII, IX, X, XI, XIII, or Von Willebrand factor, as well as activated forms thereof), a procoagulant (e.g., propyl gallate), an anti-fibrinolytic agent (e.g., epsilon aminocaproic acid or tranexamic acid), and the like); one or more procoagulative agents (e.g., any hemostatic agent described herein, desmopressin, coagulation factor(s) (e.g., II, V, VII, VIII, IX, X, XI, XIII, or Von Willebrand factor, as well as activated forms thereof), procoagulants (e.g., propyl gallate), antifibrinolytics (e.g., epsilon aminocaproic acid), and the like); one or more anticoagulative agents (e.g., heparin or derivatives thereof, such as low molecular weight heparin, fondaparinux, or idraparinux; an anti-platelet agent, such as aspirin, dipyridamole, ticlopidine, clopidogrel, or prasugrel; a factor Xa inhibitor, such as a direct factor Xa inhibitor, e.g., apixaban or rivaroxaban; a thrombin inhibitor, such as a direct thrombin inhibitor, e.g., argatroban, bivalirudin, dabigatran, hirudin, lepirudin, or ximelagatran; ora coumarin derivative or vitamin K antagonist, such as warfarin (coumadin), acenocoumarol, atromentin, phenindione, or phenprocoumon); one or more immune modulators, including corticosteroids and non-steroidal immune modulators (e.g., NSAIDS, such as any described herein); one or more proteins; and/or one or more vitamins (e.g., vitamin A, C, and/or E). One or more of botulinum toxin, fat (e.g. autologous), hyaluronic acid, a collagen-based filler, or other filler may also be administered to skin. Platelet rich plasma may also be administered to skin. One or more therapeutic agents described herein may be formulated as a depot preparation. In general, depot preparations are typically longer acting than non-depot preparations. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

In some embodiments, a therapeutic agent may include anticoagulative and/or procoagulative agents. Without wishing to be bound by theory, in some embodiments, by controlling the extent of bleeding and/or clotting in treated skin regions, a skin tightening effect may be more effectively controlled. In some embodiments, technologies, devices and/or methods described herein include or can be used to administer one or more anticoagulative agents, one or more procoagulative agents, one or more hemostatic agents, one or more fillers, or combinations thereof. In particular embodiments, a therapeutic agent controls the extent of bleeding and/or clotting in a treated skin region, including use of one or more anticoagulative agents (e.g., to inhibit clot formation prior to skin healing or slit/hole closure) and/or one or more hemostatic or procoagulative agents.

Kits

In some embodiments, technologies, devices and/or methods described herein comprise kits for cosmetic resurfacing of skin tissue. In some embodiments, kits may include one or more of needles (e.g., hollow needles) and/or staples (e.g., hollow staples), such as in a cartridge for placement into a main body of a device or system. Needles, staples, or cartridges may be placed in sterile packaging. In some embodiments, kits may also include, either alone or with the one or more of needles (e.g., hollow needles) or staples (e.g., hollow staples), other components of an article, apparatus, or system described herein.

In some embodiments, a kit may include one or more applicators (e.g., applicator 20 shown in FIGS. 1D and 1E, applicator 45 shown in FIGS. 2A and 2E, applicator 66 shown in FIGS. 3A-3C, or applicator 76 shown in FIGS. 4A and 4B), strips (e.g., strip 41 including needles 11 (e.g., hollow needles) as shown in FIGS. 2A-2C), templates (e.g., template 42 shown in FIGS. 2B and 2C), or sleeves (e.g., sleeve 71 shown in FIGS. 4A and 4B). In some embodiments, a kit may also include one or more guide rails (e.g., guide rail 82 shown in FIG. 5A or guide rail 92 shown in FIG. 6A), inflatable bladders (e.g., inflatable bladder 102 shown in FIGS. 7A-7D), folded tape alone or containing needles (e.g., folded tape 111 including needles 11 (e.g., hollow needles)), or paddles (e.g., first paddle 121 and second paddle 123 shown in FIGS. 9A and 9B). In some embodiments, a kit may also include a cartridge comprising at least one inflatable bladder (e.g., inflatable bladder 102 shown in FIGS. 7A-7D) having needles (e.g., hollow needles) and/or staples (e.g., hollow staples) on a first surface of a bladder. In some embodiments, a kit may also include a cartridge comprising a folded tape (e.g., folded tape 111 shown in FIG. 8A) having needles (e.g., hollow needles) and/or staples (e.g., hollow staples) on a first surface of a folded tape. A cartridge in a kit may be configured for installation in a main body of a device described herein. In some embodiments, kits may be packaged with needle(s) and/or staple(s) in sterile form and with instructions for applying and assembling needle(s) and/or staple(s) to an article, apparatus, or system described herein and/or with instructions for applying the article, apparatus, or system to an actuation unit. Kits may also include one or more replacement needles (e.g., hollow needles) or staples (e.g., hollow staples) and/or one or more replacement components of the article, apparatus, or system. In some embodiments, a kit may also include entire articles, apparatuses, or systems as replacement parts. For example, a kit may include already assembled article 10 including needles 11 (e.g., hollow needles) (see FIG. 1A) in its entirety. One or more of the components in a kit described above may be present in the kit in sterile package.

In some embodiments, a kit as described herein may include additional components, such as a trap for collecting waste materials (e.g., cored tissue portions); mechanisms for actuation, translation, and position detection (e.g., one or more voice coil (VC), pneumatic, electromagnetic, and/or piezoelectric actuators; driving wheels; and/or a camera); and a base unit having a user interface. In some embodiments, a kit as described herein may include any other useful components, such as instructions on how to use needle(s) or staples, an actuation unit, one or more therapeutic agents (e.g., any described herein, such as an anticoagulative and/or procoagulative agent, and optionally in combination with a useful dispenser for applying a therapeutic agent, such as a brush, spray, film, ointment, cream, lotion, or gel), one or more wound cleansers (e.g., including any antibiotic, antimicrobial, or antiseptic, such as those described herein, in any useful form, such as a brush, spray, film, ointment, cream, lotion, or gel), one or more dressings (e.g., compressive or occlusive dressings), one or more closures (e.g., bandage, hemostats, sutures, or adhesives), one or more debriding agents, one or more adhesives (e.g., any described herein), and/or one or more cosmetics (e.g., as described herein), and/or other suitable or useful materials.

In some embodiments, a kit as described herein may include any of the components provided herein (e.g., needle(s) (e.g., hollow needle(s)), staples (e.g. hollow staple(s)), a trap, a pressure generating source, a tissue removal tool (e.g., a piston), an aspiration tube, and/or a z-actuator) in any number. Kits may also have or be designed to have any of the configurations described herein.

Methods for Cosmetic Skin Resurfacing

In some embodiments, technologies, devices and/or methods described herein may be used for cosmetic skin resurfacing of skin tissue, e.g., by removing skin tissue portions and/or by triggering biological responses that contribute to tissue resurfacing and remodeling. In some embodiments, technologies, devices and/or methods described herein may be applied to treat one or more skin regions. In particular embodiments, these regions are treated with one or more procedures to improve skin appearance and to rejuvenate skin. In preferred embodiments, technologies, devices and/or methods described herein may be useful for skin tightening, e.g., reducing skin laxity (e.g., loose or sagging skin or other skin irregularities). In other embodiments, technologies, devices and/or methods described herein may be useful for removal of, e.g., pigment, hair follicles, and/or vessels in the skin, and/or for treating acne, allodynia, blemishes, ectopic dermatitis, hyperpigmentation, hyperplasia (e.g., lentigo or keratosis), loss of translucency, loss of elasticity, melasma (e.g., epidermal, dermal, or mixed subtypes), photodamage, rashes (e.g., erythematous, macular, papular, and/or bullous conditions), psoriasis, rhytides (or wrinkles, e.g., lateral canthal lines ("crow's feet"), age-related rhytides, sun-related rhytides, or heredity-related rhytides), sallow color, scar contracture (e.g., relaxation of scar tissue), scarring (e.g., due to acne, surgery, or other trauma), skin aging, skin contraction (e.g., excessive tension in the skin), skin irritation/sensitivity, striae (or stretch marks), tattoo removal, vascular lesions (e.g., angioma, erythema, hemangioma, papule, port wine stain, rosacea, reticular vein, or telangiectasia), or any other unwanted skin irregularities. In some embodiments, technologies, devices and/or methods described herein may also be used to penetrate skin and trigger biological responses that may contribute to new skin tissue formation and tissue resurfacing and remodeling.

In some embodiments, technologies, devices and/or methods described herein may be applied to any part or parts of the body, including face (e.g., eyelid, lips, cheeks, chin, forehead, lips, or nose), neck, chest (e.g., as in a breast lift), arms, hands, legs, abdomen, and/or back. In some embodiments, devices (e.g., needles (e.g., hollow needles), staples (e.g., hollow staples), articles, apparatuses, and systems), kits, and methods may be configured to be useful for treatment of regions of a body with different sizes and geometries. In some embodiments, arrays of needles (e.g., hollow needles) of different sizes, geometries, and arrangements may be included in a kit as described herein to allow for treatment of facial (e.g., with tips having small arrays of regular or irregular geometries) and/or abdominal regions (e.g., with tips having large arrays of regular geometries). In some embodiments, such arrangements and configurations can be in one or more rows or in a semi-random spatial distribution. In some embodiments, an apparatus can include a single needle (e.g., a hollow needle) and an apparatus can be used, e.g., to repeatedly remove skin tissue in a pattern forming one or more rows, random or semi-random patterns, or other patterns.

In some embodiments, treatment methods may involve forming a plurality of holes in skin by contacting one or more needles (e.g., hollow needles) or staples (e.g., hollow staples) to skin of a subject using apparatuses, devices, and systems described herein. Hollow needles or hollow staples may be configured to remove cored tissue portions from skin. Penetration into skin by needles (e.g., hollow needles) and/or staples (e.g., hollow staples) create holes and so effectively reduce tissue volume and/or improve tissue quality upon healing. In some embodiments, forming a series of cored tissue portions (e.g., removal of about 20% of the total skin area) and corresponding holes in a high laxity skin region and optionally subsequent compression of a skin region to close holes may promote growth of new skin (e.g., improved tissue). In some embodiments, healing of tissue under a dressing (e.g., a compressive or occlusive dressing) allows for existing tissue to span a gap introduced by removal of cored tissue portions, thereby reducing skin volume and area (e.g., by tightening the skin). A dressing (e.g., a compressive or occlusive dressing) may also help to maintain moisture of the treated skin area and/or to prevent delivered therapeutic agents from leaking out of skin.

In some embodiments, any beneficial area or volumetric fraction of a skin region can be removed. In some embodiments, between about 1% to about 65% (e.g., an areal fraction between about 0.01 to about 0.65, such as 0.01 to 0.65, 0.01 to 0.6, 0.01 to 0.55, 0.01 to 0.5, 0.01 to 0.45, 0.01 to 0.4, 0.01 to 0.35, 0.01 to 0.3, 0.01 to 0.25, 0.01 to 0.2, 0.01 to 0.15, 0.01 to 0.1, 0.01 to 0.05, 0.03 to 0.65, 0.05 to 0.65, 0.07 to 0.65, 0.09 to 0.65, 0.1 to 0.65, 0.15 to 0.65, 0.2 to 0.65, 0.25 to 0.65, 0.3 to 0.65, 0.35 to 0.65, 0.4 to 0.65, 0.45 to 0.65, 0.5 to 0.65, 0.55 to 0.65, or 0.6 to 0.65) of tissue in a treatment area may be removed. In some embodiments, between about 1% to about 5% (e.g., an areal fraction between about 0.01 to about 0.05, such as 0.01 to 0.05, 0.01 to 0.045, 0.01 to 0.04, 0.01 to 0.035, 0.01 to 0.03, 0.01 to 0.025, 0.01 to 0.02, 0.01 to 0.015, 0.015 to 0.05, 0.02 to 0.05, 0.025 to 0.05, 0.03 to 0.05, 0.035 to 0.05, 0.04 to 0.05, or 0.045 to 0.05) of tissue in the treatment area may be removed. In some embodiments, between about 2% to about 3% (e.g., an areal fraction between about 0.02 to about 0.03, such as 0.02 to 0.03, 0.02 to 0.028, 0.02 to 0.026, 0.02 to 0.024, 0.02 to 0.022, 0.022 to 0.03, 0.024 to 0.03, 0.026 to 0.03, 0.028 to 0.03; e.g., 0.025) of tissue in the treatment area may be removed.

In some embodiments, tissue can be removed from a treatment region with various hole density (e.g., the number of holes per unit area) corresponding to a number and geometry of needles (e.g., hollow needles) or staples (e.g., hollow staples) used and a number of applications of needles and/or staples to a treatment region. Different hole densities may be desirable for different regions of skin and for different conditions, and may be achieved using different needles (e.g., hollow needles) or staples (e.g., hollow staples). In some embodiments, 15 holes corresponding to a size of a 19 gauge needle and their corresponding cored tissue portions may be created in a given treatment area by actuation of a single 19 gauge needle 15 times, or by actuating an array having five 19 gauge needles three times. Spacing the same number of holes further apart will result in a lower hole density per unit area. In some embodiments, 15 holes may be created within a 0.5 mm by 0.3 mm region or within a 5 mm by 3 mm region. In particular embodiments, devices, kits, and methods may be configured to provide from about 10 to about 10000 cored tissue portions per $cm^2$ area of a skin region (e.g., as described herein). An array of holes created by removal of the skin tissue portions may be created in any beneficial pattern within a skin region. In some embodiments, a higher density and/or smaller spacing of tissue portions and corresponding holes can be ablated in skin in a center of a pattern or in thicker portions of skin. In some embodiments, a pattern may be semi-random or include one or more of staggered rows and/or blocks, parallel rows and/or blocks, a circular pattern, a spiral pattern, a square or rectangular pattern, a triangular pattern, a hexagonal pattern, a radial distribution, or a combination of one or more such patterns. A pattern may arise from use of one or more of needles (e.g., hollow needles) and/or staples (e.g., hollow staples) with one or more configurations and numbers of needles and/or staples applied in any ordered or disordered manner. Modifications to an average length, diameter, shapes, and/or other characteristics of one or more needles (e.g., hollow needles) or staples (e.g., hollow staples) used to treat a skin region may also result in a specific pattern of holes in skin. Such patterns may be optimized to promote unidirectional, non-directional, or multidirectional contraction or expansion of skin (e.g., in the x-direction, y-direction, x-direction, x-y plane, y-z plane, x-z plane, and/or xyz-plane), such as by modifying an average length, depth, diameter, density, orientation, and/or spacing between needles (e.g., hollow needles) and/or staples (e.g., hollow staples).

In some embodiments, any portion of skin can be removed. Tissue portions created by penetration into skin with hollow needle(s) and/or hollow staple(s) may include epidermal tissue, dermal tissue, subcutaneous fat, and/or cells or tissue proximal to a dermal/fatty layer boundary (e.g., stem cells). In some embodiments, a tissue portion may have a length that corresponds to a depth of penetration of a skin layer. In some embodiments, a depth of penetration may be (i) into a dermal layer, (ii) through an entire dermal layer to a junction of a dermal layer and a subcutaneous fat layer, or (iii) into a subcutaneous fat layer. A total depth of the epidermal, dermal, and subcutaneous fat layers may vary based on a region and age of a body being treated. In some instances, a depth of an epidermal layer is between about 0.01 mm to 0.2 mm, and/or a depth of a dermal layer is between about 0.3 mm to 6.0 mm. In some embodiments, a total depth of epidermal and dermal layers may be between about 0.3 mm and 6.2 mm, corresponding to a possible tissue portion having a length between about 0.3 mm and 6.2 mm (e.g., between about 0.3 mm and 0.6 mm, 0.3 mm and 0.9 mm, 0.3 mm and 1.5 mm, 0.3 mm and 2.0 mm, 0.3 mm and 2.5 mm, 0.3 mm and 3.0 mm, 0.3 mm and 3.5 mm, 0.3 mm and 4.0 mm, 0.3 mm and 4.5 mm, 0.3 mm and 5.0 mm, 0.3 mm and 5.5 mm, 0.3 mm and 6.0 mm, 0.3 mm and 6.2 mm, 0.6 mm and 0.9 mm, 0.6 mm and 1.5 mm, 0.6 mm and 2.0 mm, 0.6 mm and 2.5 mm, 0.6 mm and 3.0 mm, 0.6 mm and 3.5 mm, 0.6 mm and 4.0 mm, 0.6 mm and 4.5 mm, 0.6 mm and 5.0 mm, 0.6 mm and 5.5 mm, 0.6 mm and 6.0 mm, 0.6 mm and 6.2 mm, 0.9 mm and 1.5 mm, 0.9 mm and 2.0 mm, 0.9 mm and 2.5 mm, 0.9 mm and 3.0 mm, 0.9 mm and 3.5 mm, 0.9 mm and 4.0 mm, 0.9 mm and 4.5 mm, 0.9 mm and 5.0 mm, 0.9 mm and 5.5 mm, 0.9 mm and 6.0 mm, 0.9 mm and 6.2 mm, 1.5 mm and 2.0 mm, 1.5 mm and 2.5 mm, 1.5 mm and 3.0 mm, 1.5 mm and 3.5 mm, 1.5 mm and 4.0 mm, 1.5 mm and 4.5 mm, 1.5 mm and 5.0 mm, 1.5 mm and 5.5 mm, 1.5 mm and 6.0 mm, 1.5 mm and 6.2 mm, 2.0 mm and 2.5 mm, 2.0 mm and 3.0 mm, 2.0 mm and 3.5 mm, 2.0 mm and 4.0 mm, 2.0 mm and 4.5 mm, 2.0 mm and 5.0 mm, 2.0 mm and 5.5 mm, 2.0 and 6.0 mm, 2.0 mm and 6.2 mm, 2.5 mm and 3.0 mm, 2.5 mm and 3.5 mm, 2.5 mm and 4.0 mm, 2.5 mm and 4.5 mm, 2.5 mm and 5.0 mm, 2.5 mm and 5.5 mm, 2.5 mm and 6.0 mm, 2.5 mm and 6.2 mm, 3.0 mm and 3.5 mm, 3.0 mm and 4.0 mm, 3.0 mm and 4.5 mm, 3.0 mm and 5.0 mm, 3.0 mm and 5.5 mm, 3.0 and 6.0 mm, 3.0 mm and 6.2 mm, 3.5 mm and 4.0 mm, 3.5 mm and 4.5 mm, 3.5 mm and 5.0 mm, 3.5 mm and 5.5 mm, 3.5 and 6.0 mm, 3.5 mm and 6.2 mm, 4.0 mm and 4.5 mm, 4.0 mm and 5.0 mm, 4.0 mm and 5.5 mm, 4.0 and 6.0 mm, 4.0 mm and 6.2 mm, 4.5 mm and 5.0 mm, 4.5 mm and 5.5 mm, 4.5 and 6.0 mm, 4.5 mm and 6.2 mm, 5.0 mm and 5.5 mm, 5.0 mm and 6.0 mm, 5.0 mm and 6.2 mm, 5.5 mm and 6.0 mm, 5.5 mm and 6.2 mm, or 6.0 mm and 6.2 mm).

In some embodiments, technologies, devices and/or methods described herein may be configured, e.g., devices (e.g., needles (e.g., hollow needles), staples (e.g., hollow staples), articles, apparatuses, and systems), kits, and methods, to provide one or more tissue portions that do not include significant amounts of subcutaneous tissue, or, in other instances, to provide tissue portions that do include significant amounts of subcutaneous tissue. In some embodiments, electronic and/or physical mechanisms may be used to control depth of penetration into skin by needles or staples and corresponding size of a cored tissue portion and hole. For example, an apparatus may include one or more scroll wheels, buttons, dials, toggles, or other components to physically retract needles and/or staples; a z-actuation mechanism (e.g., a pneumatic, electromagnetic, or piezo-electric actuator or a motor with a cam); and/or one or more sensors (e.g., force sensors, optical sensors, laser fibers, photodetectors, and/or position sensors) in communication with one or more of needles (e.g., hollow needles) or staples (e.g., hollow staples), actuators, valves, pressure generating sources, and/or user interfaces to detect the position of needle or staples and/or the position of an article, apparatus, or system relative to the treated skin portion.

Methods of using Articles having Integrated Needles

In an exemplary method of cosmetic resurfacing using article 10 (FIG. 1A), article 10 having needles 11 (e.g., hollow needles) may be adhered onto skin by contacting first layer 12, which includes an adhesive material, to skin. The adhesive material may be covered by releasable backing 14, which can be peeled off, prior to applying article 10 to the skin. Once article 10 is securely placed on skin, hand-held applicator 20 having concave tip 21 may be used to press down on protrusion 15 on second layer 13 of article 10 to translate needle 11 (e.g., a hollow needle) from a retracted position (e.g., tip 18 of needle 11 does not extend through opening 19 in first layer 12) to a protracted position (e.g., tip 18 of needle 11 extends through opening 19 in first layer 12) (see in FIG. 1C). Applicator 20 includes visualization window 23, which can be used to view a status of protrusion 15 (see FIG. 1E). A pressed protrusion indicates that a needle underneath a protrusion is inserted into skin tissue (e.g., in the protracted position), while a raised protrusion indicates that a needle is not yet inserted into skin tissue (e.g., in the retracted position) (see FIG. 1F). In some embodiments, depending on the size of the skin area needing treatment, all or a portion of needles 11 in article 10 may be inserted into skin. Article 10 may be removed (e.g., peeled off) from skin to be disposed. Applicator 20 may be sterilized for reuse.

Optionally, a gauze or dressing (e.g., a compressive or occlusive dressing) may be applied to treated skin area to promote healing of skin.

Methods of using Systems Configured to Accept Needles

Needle Strip/Trough Configuration

In an exemplary method of cosmetic resurfacing using system 40 (FIG. 2A), strip 41 including needles 11 (e.g., hollow needles) may be assembled to fit within trough 43 of template 42. Each needle 11 (e.g., a hollow needle) is configured to align with opening 44 in trough 43 when strip 41 is placed with trough 43 of template 42. An assembled template 42 and strip 41 may be adhered onto skin by contacting surface 46 of template 42, which includes an adhesive material, to skin. An adhesive material on surface 46 may be covered by releasable backing material 47, which may be removed (e.g., peeled off), prior to applying template 42 onto skin. In some embodiments, template 42 may be adhered onto skin first, prior to placing strip 41 including needles 11 within trough 43 of template 42.

Once template 42 and strip 41 are securely placed on skin, hand-held applicator 45 may be used to press down on strip 41 to translate needles 11 from a first position (e.g., tip 18 of needle 11 does not extend through opening 44) to a second position (e.g., tip 18 of needle 11 extends through opening 44). Depending on a size of skin area needing treatment, one or more strip 41 including needles 11 may be used. Subsequently, strip 41 may be removed either alone or together with template 42. Used strip 41 may be disposed. Template 42 and applicator 45 may be sterilized for repeated use. Optionally, a gauze or dressing (e.g., a compressive or occlusive dressing) may be applied to a treated skin area to promote healing of skin.

Shuttle Guide Configuration

In an exemplary method of cosmetic resurfacing using system 60 (see FIGS. 3A-3C), a template including first layer 61 and second layer 62 may be adhered onto skin by contacting second layer 62 of a template, which may include an adhesive material, to skin. Needles 11 (e.g., hollow needles) and/or receptacles 65 may be placed between first layer 61 and second layer 62 of a template before or after a template is placed on skin. Each opening 63 in second layer 62 can be engaged with tip 18 of needle 11 (e.g., a hollow needle). Receptacles 65 are disposed in tracks 64 in first layer 61. Once system 60 is assembled and placed securely on skin, hand-held applicator 66 with end effector 67 may be inserted into receptacle 65 to push on end 68 of needle 11 to translate needle 11 from a first position, in which tip 18 is aligned with opening 63, to a second position, in which tip 18 extends through opening 63 to insert into skin tissue (see FIGS. 3B and 3C). Subsequently, end effector 67 of applicator 66 may be used to advance receptacle 65 along track 64 to position receptacle 65 above an adjacent needle that has not yet been inserted into skin tissue (see FIG. 3C).

Depending on the size of the skin area needing treatment, one or more track 64 may be filled with needles 11 (e.g., hollow needles). Subsequently, an entire system 60 may be removed (e.g., peeled off) from skin once treatment is complete. Used needles 11 may be disposed. A template, receptacle 65, and/or applicator 66 may be sterilized for repeated use. Optionally, a gauze or dressing (e.g., a compressive or occlusive dressing) may be applied to the treated skin area to promote healing of the skin.

Pen-Click Configuration

In an exemplary method of cosmetic resurfacing using system 70 (see FIGS. 4A and 4B), sleeve 71 may be assembled with needle 11 (e.g., a hollow needle) and tensioner 74 before or after sleeve 71 is placed onto skin. Needle 11 may be mounted within sleeve 71 having first opening 72 and second opening 73. Tensioner 74 (e.g., a spring) may also mounted within sleeve 71. Applicator 76 having tapered end 77 may be inserted into sleeve 71 to engage with needle 11 and tensioner 74 (e.g., a spring). Applicator 76 may push needle 11 to translate needle 11 from a retracted position, in which tip 18 of needle 11 is aligned with first opening 72 of sleeve 71, to a protracted position, in which tip 18 of needle 11 extends through first opening 72 and tensioner 74 (e.g., a spring) is in compressed configuration 78. As applicator 76 is removed from sleeve 71 and disengaged from needle 11 and tensioner 74 (e.g., a spring), tensioner 74 (e.g., a spring) naturally releases back to uncompressed configuration 75 and, at the same time, translates needle 11 from a protracted position back to a retracted position.

The number of needles 11 and sleeves 71 used in this method may depend on a size of a skin area needing treatment. Once treatment is complete, sleeve 71 containing needle 11 and tensioner 74 may be removed from skin. Needle 11 may be disengaged from sleeve 71 and tensioner 74 to be disposed. Sleeve 71 and tensioner 74 may be sterilized for repeated use. Optionally, a gauze or dressing (e.g., a compressive or occlusive dressing) may be applied to the treated skin area to promote healing of the skin.

Methods of Using Systems Including Needle Guides

In an exemplary method of cosmetic resurfacing using system 80 (see FIGS. 5A, 5B, and 6A-6D), guide rail 82 having raised backbone 83 and flat surface 84 may be placed onto skin. An exterior of flat surface 84 may include an adhesive material that can be used to adhere guide rail 82 onto skin. Needles 11 may be disposed in main body 81. A user may engage trough 87 of main body 81 with raised backbone 83 of guide rail 82 and activate insertion of needle 11 (e.g., a hollow needle) into skin tissue using an activation button on main body 81. Needle 11 may be inserted into skin tissue through opening 86 on flat surface 84 of guide rail 82.

Once treatment is complete, guide rail 82 and needles 11 may be removed from skin together. Needles 11 may be disposed. Guide rail 82 and main body 81 may be sterilized for subsequent use. Optionally, a gauze or dressing (e.g., a compressive or occlusive dressing) may be applied to treated skin area to promote healing of skin.

Methods of Using Systems Including Needles and/or Staples

Bladder Configuration

In an exemplary method of cosmetic resurfacing using device 100 (see FIGS. 7A-7D), inflatable bladder 102 in a collapsed form (see FIG. 7A) may be placed onto skin. A user may insert or "staple" staples 101 (e.g., hollow staples) into skin tissue over first surface 103 of inflatable bladder 102 using a main body that contains staples 101. Once a desired number of staples 101 is inserted into skin tissue, in order to remove staples 101, a user may use an external device to supply air to inflate inflatable bladder 102. Staples 101 are pushed out of skin tissue once a bladder is inflated (see FIG. 7B). Inflatable bladder 102 in its inflated form and staples 101 may be removed from skin together. Alternatively, staples 101 may be removed and disposed, and inflatable bladder 102 may be collapsed for subsequent use in the same skin area. Inflatable bladder 102 may be sterilized and reused. Optionally, a gauze or dressing (e.g., a compressive or occlusive dressing) may be applied to treated skin area to promote healing of skin.

Tape Configuration

In an exemplary method of cosmetic resurfacing using device 110 (see FIGS. 8A-8D), folded tape 111 including needles 11 may be installed in main body 114. A user may use an activation button on main body 114 to release portions of folded tape 111 and to insert needles 11 into skin tissue. Once treatment is complete, portions of folded tape 111 including needles 11 that are inserted into the skin tissue may be detached from main body 114. To remove needles 11, a user may peel folded tape 111 from skin tissue. Used folded tape 111 including needles 11 may be disposed. Main body 114 may be replenished with new folded tape 111 including needles 11, if needed. Main body 114 may be sterilized for subsequent use. Optionally, a gauze or dressing (e.g., a compressive or occlusive dressing) may be applied to treated skin area to promote healing of skin.

Methods of Using Apparatus Including Paddles

In an exemplary method of cosmetic resurfacing using apparatus 120 (see FIGS. 9A and 9B), an eyelid, a lip (e.g., an upper lip), or other skin regions that can be placed between paddles of apparatus 120 may be treated. In treating skin tissue of eyelid 130, a user may lift an eyelid to contact an eyelid between inner surface 122 of first paddle 121 and inner surface 124 of second paddle 123 of apparatus 120. A user may then choose a needle cluster with a desired density using lever 126 on handle 125. A user may push activation button 128 to translate needles 11 (e.g., hollow needles) from a first position, in which needles are aligned with openings on inner surface 122, to a second position, in which needles are extended from inner surface 122 to insert into eyelid 130. Release of activation button 128 may withdraw needles 11 from skin tissue. In this configuration, an entire apparatus 120 including needles 11 may be sterilized for subsequence use. Optionally, a gauze or dressing (e.g., a compressive or occlusive dressing) may be applied to treated skin area to promote healing of skin.

EXAMPLES

Example 1—Treatment of Skin Laxity in the Face Using an Article with Embedded Needles An article of the invention may be used to administer treatment to skin of a subject. Treatment may be performed outside of an operating room environment, thereby minimizing cost of treatment.

For example, an article may be that shown in FIG. 1A (e.g., article 10 including needles 11 (e.g., hollow needles) embedded within first layer 12 and second layer 13). For treatment of skin laxity in the face, e.g., in an area on the cheek, an article of the appropriate size may be made. The needles in the article may be 24 gauge needles. Each needle may have two prongs each having a bevel angle of 30 degrees. The needles in an article may be configured to penetrate about 0.3 mm to about 2 mm (e.g., about 1 mm) into the skin and to remove an areal fraction of about 0.03 of skin tissue.

The skin area may first be anesthetized, sterilized, treated with chemicals, and/or otherwise prepared for treatment. Treatment may proceed by adhering an article onto a sterilized skin area and inserting the needles into skin tissue by pressing on protrusions (e.g., protrusions 15) in the second layer of the article using an applicator (e.g., applicator 20). When a desired number of needles have been inserted into skin tissue, needles may be removed by peeling the entire article off from the cheek. Skin surface and/or holes are cleaned and/or flushed with fluid, and optionally a compressive wound dressing applied to the skin to cause the holes to close. A used article may be discarded or disassembled and/or sterilized for subsequent use.

A treatment may minimize patient downtime, allowing treatment to be carried out as an outpatient procedure. Within days, a reduction in skin laxity and/or rhytides in the treatment area may be observed.

Example 2—Treatment of Skin Laxity in the Abdomen Using a System Configured to Accept Needles A system of the invention may be used to administer treatment to skin of a subject. Treatment may be performed outside of an operating room environment, thereby minimizing the cost of treatment.

For example, the system may be that shown in FIG. 2A (e.g., system article 40 including template 42, strip 41 affixed with needles 11 (e.g., hollow needles), and applicator 45). For treatment of skin laxity, e.g., in the abdomen, needles affixed on the strip may be 22 gauge needles. Each needle may have two prongs each having a bevel angle of 30 degrees. Needles may be configured to penetrate about 0.3 mm to about 2 mm (e.g., about 1 mm) into the skin and to remove an areal fraction of about 0.03 of skin tissue.

The skin area in the abdomen may first be anesthetized, sterilized, treated with chemicals, and/or otherwise prepared for treatment. Treatment may proceed with adhering a template onto the sterilized skin area, placing one or more strips into troughs in the template, and inserting needles into skin tissue by pressing on a strip using the applicator. When the desired number of needles have been inserted into skin tissue, needles may be removed by peeling an entire strip off, or removing the template and the strip from the skin tissue. The skin surface and/or holes are cleaned and/or flushed with fluid, and optionally a compressive wound dressing applied to the skin to cause holes to close. The used article may be discarded or disassembled and/or sterilized for subsequent use.

A treatment may minimize patient downtime, allowing treatment to be carried out as an outpatient procedure. Within days, a reduction in skin laxity and/or rhytides in the treatment area may be observed.

Example 3—Treatment of Skin Laxity in the Eyelid Using an Apparatus

An apparatus of the invention may be used to administer treatment to skin of a subject. Treatment may be performed outside of an operating room environment, thereby minimizing the cost of treatment.

For example, the apparatus may be that shown in FIG. 9A (e.g., apparatus 120 including first paddle 121, second paddle 123, and needles 11 (e.g., hollow needles) embedded within the first paddle). For treatment of skin laxity in an eyelid (e.g., eyelid 130), needles may be 24 gauge needles. Each needle may have two prongs each having a bevel angle of 30 degrees. Needles may be configured to penetrate about 0.2 mm to about 1 mm into the outer surface of the eyelid (e.g., eyelid 130) and to remove an areal fraction of about 0.03 of skin tissue in the eyelid (e.g., eyelid 130).

The outer surface of an eyelid (e.g., eyelid 130) may first be anesthetized, sterilized, treated with chemicals, and/or otherwise prepared for treatment. Depending on the desired areal fraction of skin tissue removal, a needle cluster with a desired number and/or arrangement of needles may be chosen using a lever on a handle of an apparatus (e.g., lever 126 on handle 125). Treatment may proceed with gently contacting the eyelid (e.g., eyelid 130) between paddles of an apparatus and inserting needles into an outer surface of the eyelid by pressing an activation button on a handle (e.g., activation button 128 on handle 125). An activation button may also control the withdrawal of needles from an outer surface of an eyelid (e.g., eyelid 130). Once the apparatus is removed from an eyelid (e.g., eyelid 130), the eyelid may be cleaned and/or flushed with fluid, and optionally a compressive wound dressing applied to the skin to cause the holes to close. The used article may be discarded or disassembled and/or sterilized for subsequent use.

A treatment may minimize patient downtime, allowing treatment to be carried out as an outpatient procedure. Within days, a reduction in skin laxity and/or rhytides in the treatment area may be observed.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety.

Other embodiments are within the following claims.

The invention claimed is:

1. An article for producing a cosmetic effect in a skin tissue, comprising:
   a) a first and a second layer;
   b) a plurality of hollow needles, at least a portion of each one of the plurality of hollow needles positioned between the first and second layers, wherein the article is constructed and arranged so that the needles can adopt at least two positions relative to the layers, wherein the at least two positions include a retracted position and a protracted position;
   c) an applicator configured to contact at least one of the plurality of needles; and
   d) a z-actuator installed in the applicator, whereby pressure from the z-actuator on the at least one of the plurality of needles extends the at least one of the plurality of needles to the protracted position,
   wherein at least a portion of the first layer further comprises an adhesive material.

2. The article of claim 1, wherein the first layer comprises a plurality of openings and tips of the needles are aligned with the openings in the first layer when the needles are in the retracted position.

3. The article of claim 2, wherein when the needles are extended to the protracted position, the tips of the needles are configured to extend through the openings in the first layer and to insert into the skin tissue when the article is in contact with the skin tissue.

4. The article of claim 1, wherein the one or more hollow needles are configured to remove a portion of the skin tissue when extended into and extracted from the skin tissue.

5. The article of claim 1, wherein each of the needles is in contact with a tensioner that is configured to hold the needles in the retracted position.

6. The article of claim 1, wherein each of the needles is in contact with a tensioner that is configured to restore the needles to the retracted position after the needles are extended to the protracted position.

7. The article of claim 1, further comprising a releasable backing material that covers, and can be removed to expose, the adhesive material.

8. The article of claim 1, wherein the adhesive material is a pressure sensitive adhesive (PSA), a non-reactive adhesive, a contact adhesive, a hot melt adhesive, a reactive adhesive, a one-part adhesive, a natural adhesive, or a synthetic adhesive.

9. The article of claim 1, wherein at least a portion of the first layer further comprises a texture configured to reduce movement along the skin tissue.

10. The article of claim 9, wherein the texture comprises hooks, bumps, ridges, or grooves.

11. The article of claim 1, wherein said second layer comprises a plurality of protrusions, wherein each protrusion indicates a location of a single one of the plurality of needles, and wherein the protrusions are configured to be pushed down to extend the needles to the protracted position.

12. A method for producing a cosmetic effect in a skin tissue of a subject, comprising:
    applying the article of claim 1 on the skin tissue,
    translating the needles in the article from the retracted position to the protracted position, thereby inserting the needles into the skin tissue, and
    removing the needles from the skin tissue.

13. The method of claim 12, wherein portions of the skin tissue are removed by the hollow needles.

14. The method of claim 13, wherein the method produces a plurality of holes in the skin tissue.

15. The method of claim 12, wherein the skin tissue is an eyelid, a cheek, a chin, a forehead, a lip, a nose, a neck, a chest, a breast, an arm, a hand, a leg, an abdomen, and/or a back.

16. The method of claim 12, wherein removing the needles from the skin tissue comprises extracting the needles by moving the needles from the protracted position to the retracted position.

17. The method of claim 12, wherein removing the needles from the skin tissue comprises removing the article from the skin tissue.

18. The article of claim 1, wherein the z-actuator is controlled by digital controls in a user interface.

19. The article of claim 18, comprising a position detection mechanism.

20. An article for producing a cosmetic effect in a skin tissue, comprising:
    a) a first and a second layer;
    b) a plurality of hollow needles, at least a portion of each one of the plurality of hollow needles positioned between the first and second layers, wherein the article is constructed and arranged so that the needles can adopt at least two positions relative to the layers, wherein the at least two positions include a retracted position and a protracted position;
    c) an applicator configured to contact at least one of the plurality of needles; and
    d) a z-actuator installed in the applicator, whereby pressure from the z-actuator on the at least one of the plurality of needles extends the at least one of the plurality of needles to the protracted position,
    wherein at least a portion of the first layer further comprises a texture configured to reduce movement along the skin tissue.

21. The article of claim 20, wherein the first layer comprises a plurality of openings and tips of the needles are aligned with the openings in the first layer when the needles are in the retracted position.

22. The article of claim 21, wherein when the needles are extended to the protracted position, the tips of the needles are configured to extend through the openings in the first layer and to insert into the skin tissue when the article is in contact with the skin tissue.

23. The article of claim 20, wherein the one or more hollow needles are configured to remove a portion of the skin tissue when extended into and extracted from the skin tissue.

24. The article of claim 20, wherein each of the needles is in contact with a tensioner that is configured to hold the needles in the retracted position.

25. The article of claim 20, wherein each of the needles is in contact with a tensioner that is configured to restore the needles to the retracted position after the needles are extended to the protracted position.

26. The article of claim 20, wherein at least a portion of the first layer further comprises an adhesive material and the article further comprises a releasable backing material that covers, and can be removed to expose, the adhesive material.

27. The article of claim 20, wherein at least a portion of the first layer further comprises an adhesive material and wherein the adhesive material is a pressure sensitive adhesive (PSA), a non-reactive adhesive, a contact adhesive, a hot melt adhesive, a reactive adhesive, a one-part adhesive, a natural adhesive, or a synthetic adhesive.

28. The article of claim 20, wherein the texture comprises hooks, bumps, ridges, or grooves.

29. The article of claim 20, wherein said second layer comprises a plurality of protrusions, wherein each protrusion indicates a location of a single one of the plurality of needles, and wherein the protrusions are configured to be pushed down to extend the needles to the protracted position.

30. A method for producing a cosmetic effect in a skin tissue of a subject, comprising:
applying the article of claim 20 on the skin tissue,
translating the needles in the article from the retracted position to the protracted position, thereby inserting the needles into the skin tissue, and
removing the needles from the skin tissue.

31. The method of claim 30, wherein portions of the skin tissue are removed by the hollow needles.

32. The method of claim 31, wherein the method produces a plurality of holes in the skin tissue.

33. The method of claim 30, wherein the skin tissue is an eyelid, a cheek, a chin, a forehead, a lip, a nose, a neck, a chest, a breast, an arm, a hand, a leg, an abdomen, and/or a back.

34. The method of claim 30, wherein removing the needles from the skin tissue comprises extracting the needles by moving the needles from the protracted position to the retracted position.

35. The method of claim 30, wherein removing the needles from the skin tissue comprises removing the article from the skin tissue.

36. The article of claim 20, wherein the z-actuator is controlled by digital controls in a user interface.

37. The article of claim 36, comprising a position detection mechanism.

38. An article for producing a cosmetic effect in a skin tissue, comprising:
a) a first and a second layer;
b) a plurality of hollow needles, at least a portion of each one of the plurality of hollow needles positioned between the first and second layers, wherein the article is constructed and arranged so that the needles can adopt at least two positions relative to the layers, wherein the at least two positions include a retracted position and a protracted position;
c) an applicator configured to contact at least one of the plurality of needles; and
d) a z-actuator installed in the applicator, whereby pressure from the z-actuator on the at least one of the plurality of needles extends the at least one of the plurality of needles to the protracted position,
wherein the z-actuator is controlled by digital controls in a user interface.

39. The article of claim 38, wherein the first layer comprises a plurality of openings and tips of the needles are aligned with the openings in the first layer when the needles are in the retracted position.

40. The article of claim 39, wherein when the needles are extended to the protracted position, the tips of the needles are configured to extend through the openings in the first layer and to insert into the skin tissue when the article is in contact with the skin tissue.

41. The article of claim 38, wherein the one or more hollow needles are configured to remove a portion of the skin tissue when extended into and extracted from the skin tissue.

42. The article of claim 38, wherein each of the needles is in contact with a tensioner that is configured to hold the needles in the retracted position.

43. The article of claim 38, wherein each of the needles is in contact with a tensioner that is configured to restore the needles to the retracted position after the needles are extended to the protracted position.

44. The article of claim 38, wherein at least a portion of the first layer further comprises an adhesive material and the article further comprises a releasable backing material that covers, and can be removed to expose, the adhesive material.

45. The article of claim 38, wherein at least a portion of the first layer further comprises an adhesive material and wherein the adhesive material is a pressure sensitive adhesive (PSA), a non-reactive adhesive, a contact adhesive, a hot melt adhesive, a reactive adhesive, a one-part adhesive, a natural adhesive, or a synthetic adhesive.

46. The article of claim 38, wherein at least a portion of the first layer further comprises a texture configured to reduce movement along the skin tissue and the texture comprises hooks, bumps, ridges, or grooves.

47. The article of claim 38, wherein said second layer comprises a plurality of protrusions, wherein each protrusion indicates a location of a single one of the plurality of needles, and wherein the protrusions are configured to be pushed down to extend the needles to the protracted position.

48. A method for producing a cosmetic effect in a skin tissue of a subject, comprising:
applying the article of claim 38 on the skin tissue,
translating the needles in the article from the retracted position to the protracted position, thereby inserting the needles into the skin tissue, and
removing the needles from the skin tissue.

49. The method of claim 48, wherein portions of the skin tissue are removed by the hollow needles.

50. The method of claim 49, wherein the method produces a plurality of holes in the skin tissue.

51. The method of claim 48, wherein the skin tissue is an eyelid, a cheek, a chin, a forehead, a lip, a nose, a neck, a chest, a breast, an arm, a hand, a leg, an abdomen, and/or a back.

52. The method of claim 48, wherein removing the needles from the skin tissue comprises extracting the needles by moving the needles from the protracted position to the retracted position.

53. The method of claim 48, wherein removing the needles from the skin tissue comprises removing the article from the skin tissue.

54. The article of claim 38, comprising a position detection mechanism.

* * * * *